United States Patent [19]

Chen et al.

[11] Patent Number: 5,536,716

[45] Date of Patent: Jul. 16, 1996

[54] SPIRO PIPERIDINES AND HOMOLOGS WHICH PROMOTE RELEASE OF GROWTH HORMONE

[75] Inventors: Meng-Hsin Chen, Westfield; David B. R. Johnston, Warren; Ravi P. Nargund, East Brunswick; Arthur A. Patchett; James R. Tata, both of Westfield; Lihu Yang, Edison, all of N.J.

[73] Assignee: Merck & Co., Inc., Rahway, N.J.

[21] Appl. No.: 147,226

[22] Filed: Nov. 3, 1993

Related U.S. Application Data

[63] Continuation-in-part of Ser. No. 989,322, Dec. 11, 1992, abandoned.
[51] Int. Cl.[6] .......................... A61K 31/55; A61K 31/44; C07D 401/04; C07D 451/00
[52] U.S. Cl. .................. 514/215; 514/224.2; 514/230.5; 514/248; 514/278; 540/521; 540/523; 546/17; 546/18; 544/6; 544/70
[58] Field of Search ..................... 546/17, 18; 514/278, 514/215, 224.2, 230.5, 248; 540/521, 523; 544/6, 70, 23

[56] References Cited

FOREIGN PATENT DOCUMENTS

| | | |
|---|---|---|
| 0144230A3 | 6/1985 | European Pat. Off. . |
| 0431943A2 | 6/1991 | European Pat. Off. . |
| 0513974A1 | 11/1992 | European Pat. Off. . |

*Primary Examiner*—Warren Ivy
*Assistant Examiner*—Raymond Covington
*Attorney, Agent, or Firm*—J. Eric Thies; David L. Rose

[57] ABSTRACT

There are disclosed certain novel compounds identified as spiro piperidines and homologs which promote the release of growth hormone in humans and animals. This property can be utilized to promote the growth of food animals to render the production of edible meat products more efficient, and in humans, to treat physiological or medical conditions characterized by a deficiency in growth hormone secretion, such as short stature in growth hormone deficient children, and to treat medical conditions which are improved by the anabolic effects of growth hormone. Growth hormone releasing compositions containing such spiro compounds as the active ingredient thereof are also disclosed.

19 Claims, No Drawings

1

SPIRO PIPERIDINES AND HOMOLOGS WHICH PROMOTE RELEASE OF GROWTH HORMONE

CROSS REFERENCE TO RELATED APPLICATIONS

This application is a continuation-in-part of our application Ser. No. 07/989,322 filed 11 Dec. 1992 now abandoned.

BACKGROUND OF THE INVENTION

Growth hormone, which is secreted from the pituitary, stimulates growth of all tissues of the body that are capable of growing. In addition, growth hormone is known to have the following basic effects on the metabolic processes of the body:

1. Increased rate of protein synthesis in all cells of the body;

2. Decreased rate of carbohydrate utilization in cells of the body;

3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carded with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. The instant compounds are non-peptide analogs for promoting the release of growth hormone which are stable in a variety of physiological environments and which may be administered parenterally, nasally or by the oral route.

SUMMARY OF THE INVENTION

The instant invention covers certain spiro compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the spiro compounds. It is a further object of this invention to describe procedures for the preparation of such compounds. A still further object is to describe the use of such compounds to increase the secretion of growth hormone in humans and animals. A still further object of this invention is to describe compositions containing the spiro compounds for the use of treating humans and animals so as to increase the level of growth hormone secretions. Further objects will become apparent from a reading of the following description.

DESCRIPTION OF THE INVENTION

The novel spiro compounds of the instant invention are best described in the following structural formulas I and II:

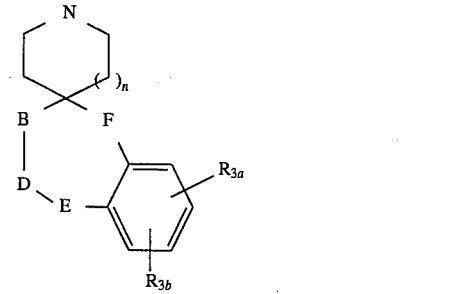

Formula I

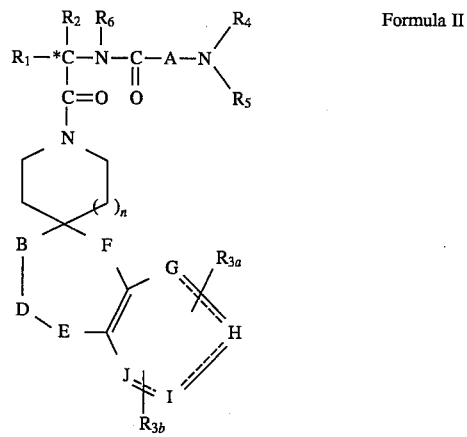

Formula II $R_1$ is $C_1$-$C_{10}$ alkyl, aryl, aryl ($C_1$-$C_6$ alkyl) and $C_3$-$C_7$ cycloalkyl ($C_1$-$C_6$alkyl) or $C_1$-$C_5$alkyl-K-$C_1$-$C_5$ alkyl, aryl($C_0$-$C_5$ alkyl)-K-($C_1$-$C_5$ alkyl), $C_3$-$C_7$ cycloalkyl($C_0$-$C_5$ alkyl)-K-($C_1$-$C_5$ alkyl) where K is O, S(O)m, N($R_2$)C(O), C(O)N($R_2$), OC(O), C(O)O, or —$CR_2$=$CR_2$— or —C≡C— where the aryl groups are defined below and the $R_2$ and alkyl groups may be futher substituted by 1 to 9 halogen, S(O)m$R_{2a}$, 1 to 3 O$R_{2a}$ or C(O)O$R_{2a}$ and the aryl groups may be further substituted by phenyl, phenoxy, halophenyl, 1–3 $C_1$-$C_6$ alkyl, 1 to 3 halogen, 1 to 2 O$R_2$, methylenedioxy, S(O)m$R_2$, 1 to 2 $CF_3$, $OCF_3$, nitro, N($R_2$)($R_2$), N($R_2$)C(O)$R_2$, C(O)O$R_2$, C(O)N($R_2$)($R_2$), $SO_2N(R_2)(R_2)$, N($R_2$)S(O)$_2$ aryl or N($R_2$)$SO_2R_2$;

$R_2$ is hydrogen, $C_1$-$C_6$ alkyl, $C_3$-$C_7$ cycloalkyl, and where two $C_1$-$C_6$ alkyl groups are present on one atom, they may be optionally joined to form a $C_3$-$C_8$ cyclic ring optionally including oxygen, sulfur or $NR_{2a}$;

$R_{2a}$ is hydrogen or $C_1$-$C_6$ alkyl;

$R_{3a}$ and $R_{3b}$ are independently hydrogen, halogen, $C_1$-$C_6$ alkyl, $OR_2$, cyano, $OCF_3$, methylenedioxy, nitro, $S(O)_m^R$, $CF_3$ or $C(O)OR_2$ and when $R_{3a}$ and $R_{3b}$ are in an ortho arrangement, they may be joined to form a $C_5$ to $C_8$ aliphatic or aromatic ring optionally including 1 or 2 heteroatoms selected from oxygen, sulfur or nitrogen;

$R_4$ and $R_5$ are independently hydrogen, $C_1$-$C_6$ alkyl, substituted $C_1$-$C_6$ alkyl where the substituents may be 1 to 5 halo, 1 to 3 hydroxy, 1 to 3 $C_1$-$C_{10}$ alkanoyloxy, 1 to 3 $C_1$-$C_6$ alkoxy, phenyl, phenoxy, 2-furyl, $C_1$-$C_6$ alkoxycarbonyl, $S(O)_m(C_1$-$C_6$ alkyl); or $R_4$ and $R_5$ can be taken together to form —$(CH_2)_rL_a(CH_2)_s$— where $L_a$ is $C(R_2)_2$, O, $S(O)_m$ or $N(R_2)$, r and s are independently 1 to 3 and $R_2$ is as defined above;

$R_6$ is hydrogen or $C_1$-$C_6$ alkyl;

A is:

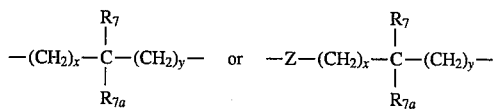

where x and y are independently 0–3;

Z is N—$R_2$ or O;

$R_7$ and $R_{7a}$ are independently hydrogen, $C_1$-$C_6$ alkyl, $OR_2$, trifluoromethyl, phenyl, substituted $C_1$-$C_6$ alkyl where the substituents are imidazolyl, phenyl, indolyl, p-hydroxyphenyl, $OR_2$, 1 to 3 fluoro, $S(O)_mR_2$, $C(O)OR_2$, $C_3$-$C_7$ cycloalkyl, $N(R_2)(R_2)$, $C(O)N(R_2)(R_2)$; or $R_7$ and $R_{7a}$ can independently be joined to one or both of $R_4$ and $R_5$ groups to form alkylene bridges between the terminal nitrogen and the alkyl portion of the $R_7$ or $R_{7a}$ groups, wherein the bridge contains 1 to 5 carbons atoms;

B, D, E, and F are independently $C(R_8)(R_{10})$, O, C=O, $S(O)_m$, or $NR_9$, such that one or two of B,D,E, or F may be optionally missing to provide a 5, 6, or 7 membered ring; and provided that B, D, E and F can be $C(R_8)(R_{10})$ or C=O only when one of the remaining B, D, E and F groups is simultaneously O, $S(O)m$ or $NR_9$; B and D or D and E taken together may be N=$CR_{10}$— or $CR_{10}$=N or B and D or D and E taken together may be $CR_8$=$CR_{10}$ provided one of the other of B and E or F is simultaneously O, $S(O)_m$ or $NR_9$;

$R_8$ and $R_{10}$ are independently hydrogen, $R_2$, $OR_2$, $(CH_2)_q$ aryl, $(CH_2)_q C(O)OR_2$, $(CH_2)_q C(O)O(CH_2)_q$ aryl or $(CH_2)_q$ (1H-tetrazol- 5-yl) and the aryl may be optionally substituted by 1 to 3 halo, 1 to 2 $C_1$-$C_8$ alkyl, 1 to 3 $OR_2$ or 1 to 2 $C(O)OR_2$;

$R_9$ is $R_2$, $(CH_2)_q$ aryl, $C(O)R_2$, $C(O)(CH_2)_q$ aryl, $SO_2R_2$, $SO_2 (CH_2)_q$ aryl, $C(O)N(R_2)(R_2)$, $C(O)N(R_2)(CH_2)_q$ aryl, $C(O)OR_2$, 1-H-tetrazol- 5-yl, $SO_3H$, $SO_2NHC\equiv N$, $SO_2N(R_2)$aryl, $SO_2N(R_2)(R_2)$ and the $(CH_2)_q$ may be optionally substituted by 1 to 2 $C_1$-$C_4$ alkyl, and the $R_2$ and aryl may be optionally further substituted by 1 to 3 $OR2a$, $O(CH_2)_q$ aryl, 1 to 2 $C(O)OR_{2a}$, 1 to 2 $C(O)O(CH_2)_q$ aryl, 1 to 2 $C(O)N(R_{2a})(R_{2a})$, 1 to 2 $C(O)N(R_{2a})(CH_2)_q$ aryl, 1 to 5 halogen, 1 to 3 $C_1$-$C_4$ alkyl, 1,2,4-triazolyl, 1-H-tetrazol- 5-yl, $C(O)NHSO_2R_{2a}$, $S(O)_mR_{2a}$, $C(O)NHSO_2(CH_2)q$ aryl, $SO_2NHC\equiv N$, $SO_2NHC(O)R_{2a}$, $SO_2NHC(O)(CH_2)_q$ aryl, $N(R_2)C(O)N(R_{2a})(R_{2a})$, $N(R_{2a})C(O)N(R_{2a})(CH_2)_q$ aryl, $N(R_{2a})(R_{2a})$, $N(R_{2a})C(O)R_{2a}$, $N(R_{2a})C(O)(CH_2)_q$ aryl, $OC(O)N(R_{2a})(R_{2a})$, $OC(O)N(R_{2a})(CH_2)_q$ aryl; $SO_2(CH_2)_qCONH$—$(CH_2)_wNHC(O)R_{11}$, where w is 2–6 and $R_{11}$ may be biotin, aryl, or aryl substituted by 1 or 2 $OR_2$, 1–2 halogen, azido or nitro;

m is 0, 1 or 2;

n is 1 or 2;

q can optionally be 0, 1, 2, 3, or 4; and

G, H, I and J are carbon, nitrogen, sulfur or oxygen atoms, such that at least one is a heteroatom and one of G, H, I or J may be optionally missing to afford 5 or 6 membered heterocyclic aromatic rings; and pharmaceutically acceptable salts and individual diastereomers thereof.

In the above structural formulas and throughout the instant specification, the following terms have the indicated meanings:

The alkyl groups specified above are intended to include those alkyl groups of the designated length in either a straight or branched configuration which may optionally contain double or triple bonds. Exemplary of such alkyl groups are methyl, ethyl, propyl, ethinyl, isopropyl, butyl, sec-butyl, tertiary butyl, pentyl, isopentyl, hexyl, isohexyl, allyl, propenyl, butenyl, butadienyl and the like.

The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propinyloxy, isobutenyloxy, 2-hexenyloxy, and the like.

The term "halogen" is intended to include the halogen atom fluorine, chlorine, bromine and iodine.

The term "aryl" is intended to include phenyl and naphthyl and aromatic residues of 5- and 6- membered rings with 1 to 3 heteroatoms or fused 5 or 6 membered bicyclic rings with 1 to 3 heteroatoms of nitrogen, sulfur or oxygen. Examples of such heterocyclic aromatic rings are pyridine, thiophene, benzothiophene, tetrazole, indole, N-methylindole, dihydroindole, indazole, N-formylindole, benzimidazole, thiazole, furan, pyrimidine, and thiadiazole.

Certain of the above defined terms may occur more than once in the above formula and upon such occurrence each term shall be defined independently of the other.

Preferred compounds of the instant invention are:

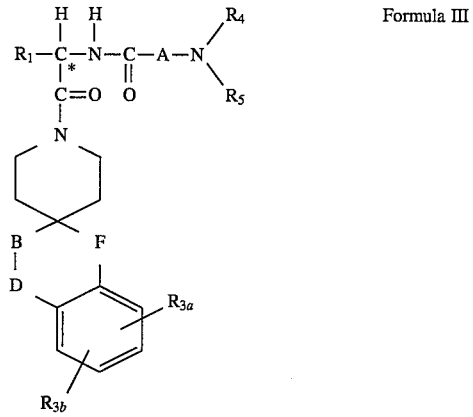

Formula III where $R_1$ is $C_1$-$C_{10}$ alkyl, aryl ($C_1$-$C_4$ alkyl), $C_3$-$C_6$ cycloalkyl ($C_1$-$C_4$ alkyl), ($C_1$-$C_4$ alkyl)—K—($C_1$-$C_4$ alkyl), aryl($C_0$-$C_5$ alkyl)—K—($C_1$-$C_4$ alkyl), ($C_3$-$C_7$cycloalkyl)($C_0$-$C_5$ alkyl)—K—($C_1$-$C_4$alkyl) where K is O, $S(O)_m$, —$CR_2$=$CR_2$—; —C≡C—, or $N(R_2)C(O)$ where $R_2$ and the alkyl groups may be further substituted by 1 to 7 halogen, $S(O)_mC_1$-$C_4$ alkyl, $OR_{2a}$ or $C(O)OR_{2a}$ and the aryl groups may be further substituted by 1–2 $C_1$-$C_4$ alkyl, 1 to 2 halogen, 1 to 2 $OR_2$, $CF_3$, $OCF_3$, methylenedioxy, $S(O)_mR_2$, $SO_2N(R_2)(R_2)$, $N(R_2)SO_2R_2$ or $C(O)OR_2$;

$R_2$ is hydrogen, $C_1$-$C_6$ alkyl, $C_3$-$C_7$cycloalkyl, and, if two $C_1$-$C_6$ alkyl groups are present on one atom, they may be optionally joined to form a $C_4$-$C_6$ cyclic ring optionally including 1 to 2 heteroatoms selected from oxygen, sulfur or $NR_{2a}$;

$R_{2a}$ is hydrogen or $C_1$-$C_6$ alkyl;

R3a and $R_{3b}$ are independently hydrogen, halogen, $C_1$-$C_4$ alkyl, $OR_2$, methylenedioxy, nitro, $S(O)_mC_1$-$C_4$alkyl, $CF_3$ or $C(O)OR_2$;

$R_4$ and $R_5$ are independently hydrogen, $C_1$-$C_6$ alkyl, substituted $C_1$-$C_6$ alkyl where the substituents may be 1 to 5 halo, 1 to 2 hydroxy, 1 to 2 $C_1$-$C_6$ alkanoyloxy, 1 to 2 $C_1$-$C_6$ alkyloxy or $S(O)_m(C_1$-$C_4$ alkyl);

A is:

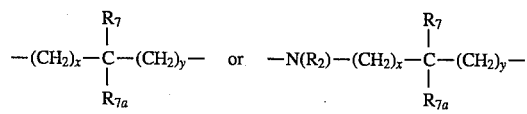

where x and y, are independently 0, 1, or 2;

$R_7$ and $R_{7a}$ are independently hydrogen, $C_1$-$C_4$ alkyl, substituted $C_1$-$C_4$ alkyl where the substituents are from 1 to 3 fluoro or imidazolyl, phenyl, indolyl, $S(O)_mC_1$-$C_4$alkyl, $C(O)OR_2$ or $R_7$ and $R_{7a}$ can independently be joined to one or both of the $R_4$ and $R_5$ groups to form alkylene bridges between the teminal nitrogen and the alkyl portion of the $R_7$ or $R_{7a}$ groups, wherein the bridge contains 1 to 3 carbon atoms;

B, D and F are independently $C(R_8)(R_{10})$, O, C=O, $S(O)_m$ or $NR_9$ such that one of B, D or F may be optionally missing to provide a 5 or 6 membered ring and provided that one of B, D and F is $C(R_8)(R_{10})$ or C=O only when one of the remaining B, D and F groups is simultaneously O, $S(O)_m$ or $NR_9$;

$R_8$ and $R_{10}$ are independently hydrogen, $R_2$, $OR_2$, $(CH_2)_q$ aryl, $(CH_2)_qC(O)OR_2$, $(CH_2)_qC(O)O(CH_2)_q$ aryl, $(CH_2)_q$(1H-tetrazol-5-yl) and the aryl may be optionally substituted by 1 to 3 halo, 1 to 2 $C_1$-$C_4$ alkyl, 1 to 3 $OR_2$ or 1 to 2 $C(O)OR_2$;

$R_9$ is $R_2$, $(CH_2)_q$ aryl, $C(O)R_2$, $C(O)(CH_2)_q$ aryl, $SO_2R_2$, $SO_2(CH_2)_q$ aryl, $C(O)N(R_2)(R_2)$, $C(O)N(R_2)(CH_2)_q$ aryl, 1-H-tetrazolyl-5-yl, $SO_2NHC\equiv N$, $SO_2NR_2$ aryl, $SO_2N(R_2)(R_2)$ and the $(CH_2)_q$ may be optionally substituted by 1 to 2 $C_1$-$C_2$ alkyl and the $R_2$ may be optionally substituted by 1 to 2 $OR_{2a}$, $O(CH_2)_q$ aryl, 1 to 2 $C(O)OR_{2a}$, $C(O)N(R_{2a})(R_{2a})$, $S(O)_mR_{2a}$, 1-H-tetrazol-5-yl, $C(O)NHSO_2R_{2a}$, $C(O)NHSO_2(CH_2)_q$ aryl, $N(R_{2a})C(O)N(R2a)(R_{2a})$ or $N(R_{2a})C(O)N(R_{2a})(CH_2)_q$ aryl and the aryl may be optionally substituted by 1 to 2 $OR_{2a}$, 1 to 2 halogen, 1 to 2 $C_1$-$C_4$ alkyl, $C(O)OR_{2a}$ or 1-H-tetrazol-5-yl; $SO_2(CH_2)_w$ $CONH(CH_2)_w$ $NHC(O)R_{11}$, where w=2–6 and $R_{11}$ may be biotin, aryl, or aryl substituted by 1 or 2 $OR_2$, 1-2 halogen, azido or nitro;

m is 0,1, or 2;

q can optionally be 0, 1, 2 or 3; and the aryl group is phenyl, napthyl, pyridyl, thienyl, indolyl, thiazolyl or pyrimidinyl, and the pharmaceutically acceptable salts and individual diastereomers thereof.

Still further preferred compounds are realized when F is not present in Compound III.

Thus, further preferred compounds of the instant invention are realized in structural formula IV.

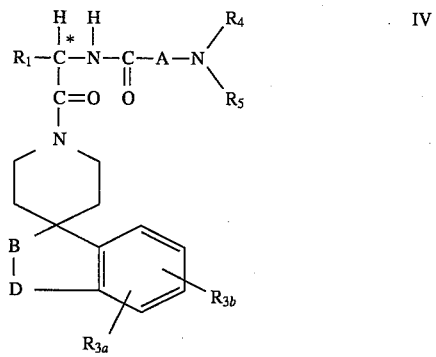

$R_1$ is $C_1$-$C_{10}$ alkyl, aryl ($C_1$-$C_4$ alkyl), $C_5$-$C_6$cycloalkyl ($C_1$-$C_4$ alkyl) or ($C_1$-$C_4$ alkyl)—K—$C_1$-$C_2$alkyl—, aryl($C_0$-$C_2$alkyl)—K—($C_1$-$C_2$ alkyl), $C_3$-$C_6$cycloalkyl ($C_0$-$C_2$alkyl)—K—($C_1$-$C_2$alkyl), where K is O or $S(O)_m$, and the aryl groups may be further substituted by 1 to 2 $C_1$-$C_4$ alkyl, 1 to 2 halogen, $OR_2$, $C(O)OR_2$, $CF_3$ or $S(O)_mR_2$;

$R_2$ is hydrogen, $C_1$-$C_4$ alkyl, cyclo $C_3$-$C_6$alkyl, and, if two $C_1$-$C_4$ alkyls are present on one atom, they may be optionally joined to form a $C_5$-$C_6$ cyclic ring optionally including the heteroatoms oxygen or $NR_{2a}$;

$R_{2a}$ is hydrogen or $C_1$-$C_4$ alkyl;

$R_{3a}$ and $R_{3b}$ are independently hydrogen, halogen, $C_1$-$C_4$ alkyl, $C(O)OR_2$, hydroxy, $C_1$-$C_4$ alkoxy, $S(O)_mC_1$-$C_4$ alkyl or $CF_3$;

$R_4$ and $R_5$ are independently hydrogen, $C_1$-$C_4$ alkyl, substituted $C_1$-$C_4$ alkyl where the substituents may be 1 to 2 hydroxy or $S(O)_m$ ($C_1$-$C_3$alkyl);

A is:

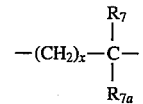

where x is 0 or 1;

$R_7$ and $R_{7a}$ are independently hydrogen, $C_1$-$C_3$ alkyl; or $R_7$ and $R_{7a}$ can independently be joined to one or both of the $R_4$ and $R_5$ groups to form alkylene bridges between the terminal nitrogen and the alkyl portion of the $R_7$ or $R_{7a}$ groups to form 5 or 6 membered rings containing the terminal nitrogen;

B and D are independently $C(R_8)(R_{10})$, C=O, O , $S(O)_m$, $NR_9$ provided that one of B and D can be $C(R_8)(R_{10})$ or C=O only when the other of B and D is O, $S(O)_m$ or $NR_9$;

$R_8$ and $R_{10}$ are independently hydrogen, $R_2$ or $(CH_2)_q$ aryl, and the aryl may be optionally substituted by 1 to 2 of halo, 1 to 2 $C_1$-$C_4$ alkyl, $OR_2$ or 1 to 2 $C(O)OR_2$;

$R_9$ is $C(O)R_2$, $C(O)(CH_2)_q$ aryl, $SO_2R_2$, $SO(CH_2)_q$ aryl, $C(O)N(R_2)(R_2)$, $C(O)N(R_2)(CH_2)_q$ aryl and the $(CH_2)_q$ may be optionally substituted by 1 to 2 $C_1$-$C_2$ alkyl and the $R_2$ may be optionally substituted by 1 to 2 of $OR_{2a}$, $O(CH_2)_q$ aryl, $C(O)OR_{2a}$, $C(O)N(R_{2a}(R_{2a})$, $S(O)mR_{2a}$, 1-H-tetrazol-5-yl, $C(O)NHSO_2R_{2a}$, or $N(R_{2a})C(O)N(R_{2a})(R_{2a})$ and the aryl may optionally be substituted by 1 to 2 $OR_{2a}$, 1 to 2 halogen, 1 to 2 $C_1$-$C_2$ alkyl, $C(O)OR_{2a}$, 1 -H-tetrazol-5-yl or $S(O)_mR_{2a}$; $SO_2(CH_2)_qCONH(CH_2)_wNHC(O)R_{11}$ where w=2–6 and $R_{11}$ may optionally be biotin, aryl, and an aryl be optionally substituted by 1 to 2 $OR_2$, 1–2 halogen, azido, nitro;

m is 0, 1 or 2;

q can optionally be 0, 1, 2 or 3;

aryl is phenyl, napthyl, pyridyl, indolyl, thienyl or tetrazolyl and the pharmaceutically acceptable salts and individual diastereomers thereof.

Most preferred compounds of the instant invention are realized in structural formula V:

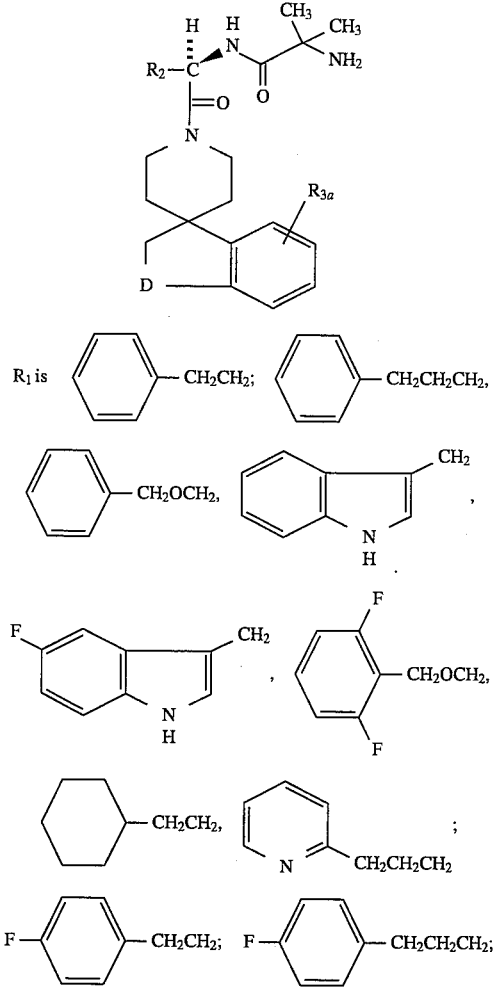

$R_{3a}$ is H, fluoro;
D is O, S, $S(O)_m$, $N(R_2)$, $NSO_2(R_2)$, $NSO_2(CH_2)_t$aryl, $NC(O)(R_2)$, $NSO_2(CH_2)_qOH$, $NSO_2(CH_2)_qCOOR_2$, $N-SO_2(CH_2)_qC(O)-N(R_2)(R_2)$, $N-SO_2(CH_2)_qC(O)-N(R_2)(CH_2)_wOH$,

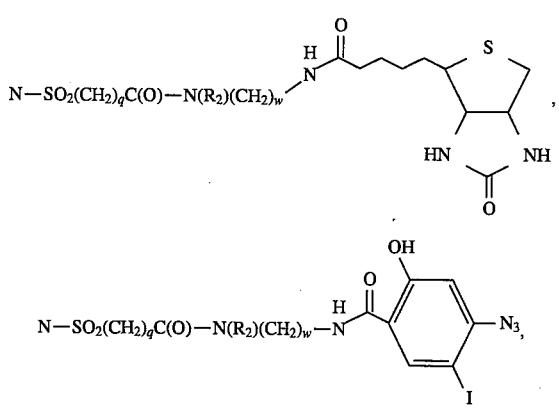

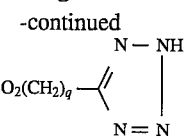

and the aryl is phenyl or pyridyl and the phenyl may be substituted by 1–2 halogen;
$R_2$ is H, $C_1$-$C_4$ alkyl;
m=1, 2;
t is 0, 1, 2;
q is 1,2,3;
w is 2–6;

and the pharmaceutically acceptable salts and individual diastereomers thereof.

Representative most preferred growth hormone releasing compounds of the present invention include the following:

1. N-[1(R)-[(1,2-Dihydro-1-methanesulfonylspiro[3H-indole-3,4'-piperidin]-1'-yl)carbonyl]-2-(1H-indol-3-yl)ethyl] -2-amino-2-methylpropanamide
2. N-[1(R)-[(1,2-Dihydro-1-methanecarbonylspiro[3H-indole-3,4'-piperudub] -1'-yl)carbonyl]-2-(1H-indol-3-yl)ethyl]-2-amino-2-methylpropanamide
3. N-[1(R)-[(1,2-Dihydro-1-benzenesulfonylspiro[3H-indole-3 4'-piperidin]-1'-yl)carbonyl]-2-(1H-indol-3-yl)ethyl] -2-amino-2-methylpropanamide
4. N-[1(R)-[(3,4-Dihydro-spiro[2H-1-benzopyran-2,4'-piperidin]-1'-yl) carbonyl]-2-(1H-indol-3-yl)ethyl]-2-amino-2-methylpropanamide
5. N-[1(R)-[(2-Acetyl-1,2,3,4-tetrahydrospiro[isoquinolin-4,4'-piperidin]-1'-yl)carbonyl]-2-(indol-3-yl)ethyl]-2-amino-2-methylpropanamide
6. N-[1(R)-[(1,2-Dihydro-1-methanesulfonylspiro[3H-indole-3,4'-piperidin]-1'-yl) carbonyl]-2-(phenylmethyloxy)ethyl]-2-amino-2-methylpropanamide
7. N-[1(R)-[(1,2-Dihydro-1-methanesulfonylspiro[3H-indole-3,4'-piperidin]-1'-yl) carbonyl]-2-(phenylmethyloxy)ethyl]-2-amino-2-methylpropanamide mesylate salt
8. N-[1(R)-[(1,2-Dihydro-1-methanesulfonylspiro[3H-indole-3,4'-piperidin]-1'-yl)carbonyl]-2-(2', 6'-difluorophenylmethyloxy)ethyl]-2 -amino-2-methylpropanamide
9. N-[1(R)-[(1,2-Dihydro-1-methanesulfonyl-5-fluorospiro[3H-indole- 3,4'-piperidin]-1'-yl)carbonyl]-2-(phenylmethyloxy)ethyl]-2-amino-2-methylpropanamide
10. N-[1(S)-[(1,2-Dihydro-1-methanesulfonylspiro[3H-indole-3 4'-piperidin]-1'-yl) carbonyl]-2-(phenylmethylthio)ethyl]-2-amino-2-methylpropanamide
11. N-[1(R)-[(1,2-Dihydro-1-methanesulfonylspiro[3H-indole-3,4'-piperidin]-1'-yl) carbonyl]-3-phenylpropyl]-2-amino-2-methylpropanamide
12. N-[1(R)-[(1,2-Dihydro-1-methanesulfonylspiro[3H-indole-3 4'-piperidin]- 1'-yl)carbonyl]-3-cyclohexylpropyl]-2-amino-2-methylpropanamide
13. N-[1(R)-[(1,2-Dihydro-1-methanesulfonylspiro[3H-indole-3,4'-piperidin]-1'-yl) carbonyl]-4-phenylbutyl]-2-amino-2-methylpropanamide
14. N-[1(R)-[(1,2-Dihydro-1-methanesulfonylspiro[3H-indole-3,4'-piperidin]-1'-yl) carbonyl]-2-(5-fluoro-1H-indol-3-yl)ethyl]-2-amino-2-methylpropanamide
15. N-[1(R)-[(1,2-Dihydro-1-methanesulfonyl-5-fluorospiro[3H-indole- 3,4'-piperidin]-1'-yl)carbonyl]-2-(5-fluoro-1H-indol-3-yl)ethyl]-2 -amino-2-methylpropanamide
16. N-[1(R)-[(1,2-Dihydro-1-(2-ethoxycarbonyl)methylsulfonylspiro-[3H-indole-3,4'-piperidin]-1'-yl)carbonyl]-2-(1H-indol-3-yl)ethyl]-2 -amino-2-methylpropanamide
17. N-[1(R)-[(1,2-Dihydro-1,1dioxospiro[3H-benzothiophene-3,4'-piperidin]-1'-yl)carbonyl]-2-(phenylmethyloxy)ethyl]-2-amino-2-methylpropanamide and pharmaceutically acceptable salts thereof.

Representative examples of the nomenclature employed are given below:

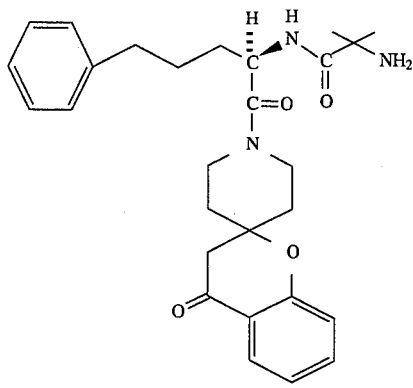

N-[1(R)-[(3,4-Dihydro-4-oxospiro[2H-1-benzopyran-2,4'-piperidin]-1'-yl)carbonyl]-4-phenylbutyl]-2-amino-2-methylpropanamide

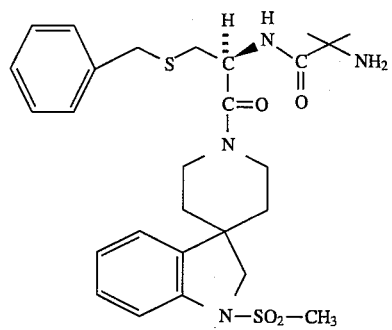

\N-[1(S)-[(1,2-Dihydro-1-methanesulfonylspiro[3H-indole-3,4'-piperidin]-1'-yl)carbonyl]-2-(phenylmethylthio)ethyl]-2-amino-2-methylpropanamide

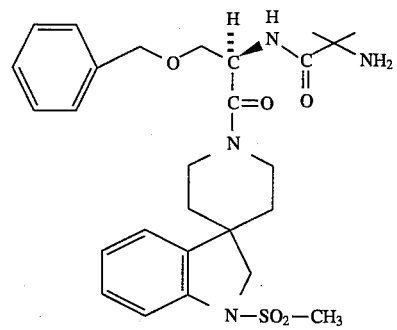

N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide Throughout the instant application, the following abbreviations are used with the following meanings:

| BOC | t-butyloxycarbonyl |
| BOP | Benzotriazol-1-yloxy tris/dimethylamino)-phosphonium hexafluorophosphate |
| CBZ | Benzyloxycarbonyl |
| DCC | Dicyclohexylcarbodiimide |
| DMF | N,N-dimethylformamide |
| EDC | 1-(3-dimethylaminopropyl)-3-ethylcarbodiimide hydrochloride |
| FAB-MS | Fast atom bombardment-mass spectroscopy |
| GHRP | Growth hormone releasing peptide |
| HOBT | Hydroxybenztriazole |
| LAH | Lithium aluminum hydride |
| HPLC | High pressure liquid chromatography |
| MHz | Megahertz |
| MPLC | Medium pressure liquid chromatography |
| NMM | N-Methylmorpholine |
| NMR | Nuclear Magnetic Resonance |
| OXONE | Potassium peroxy monosulfate |
| PLC | Preparative layer chromatography |
| PCC | Pyridinium chlorochromate |
| Ser | Serine |
| TFA | Trifluoroacetic acid |
| THF | Tetrahydrofuran |
| TLC | Thin layer chromatography |
| TMS | Tetramethylsilane |

The compounds of the instant invention all have at least one asymmetric center as noted by the asterisk in the structural Formulas I and II above. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the ambit of the instant invention. In the case of the asymmetric center represented by the asterisk in Formula I and II, it has been found that the absolute stereochemistry of the more active and thus more preferred isomers are as shown in Formula Ia. With the $R_2$ substituent as hydrogen, the special configuration of the asymmetric center corresponds to that in a D-amino acid. In most cases this is also designated an R-configuration although this will vary according to the values of $R_1$ and $R_2$ used in making R- or S stereochemical assignments.

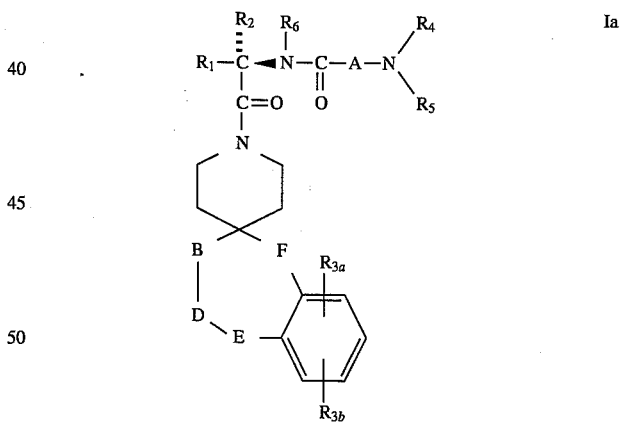

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The preparation of compounds I and II of the present invention can be carded out in sequential or convergent synthetic routes. Syntheses detailing the preparation of the compounds of Formula I and II in a sequential manner are presented in the following reaction schemes.

The protected amino acid derivatives 1 are, in many cases, commercially available where the protecting group L is, for example, BOC or CBZ groups. Other protected amino acid derivatives I can be prepared by literature methods. Many of the spiro piperidines and spiroazepines (n=2) of formula 2 and 2a are known in the literature and can be derivatized on the phenyl or heteroaryl by standard means, such as halogenation, nitration, sulfonylation, etc. Alternatively, various phenyl or heteroaryl substituted spiro piperidines and spiroazepines (n=2) can be prepared following literature methods using derivatized phenyl and heteraryl intermediates. In Schemes subsequent to Scheme I, the synthetic methods are illustrated only with spiropiperidines although it will be appreciated by those skilled in the art that the illustrated transformations can also be carried out in the higher homolog series to afford compounds of Formulas I and II with n=2.

Intermediates of formulas 3 and 3a can be synthesized as described in Scheme 1. Coupling of spiro piperidines of formula 2 and 2a to protected amino acids of formula 1, wherein L is a suitable protecting group, is conveniently carried out in an inert solvent such as dichloromethane by a coupling reagent such as DCC or EDC in the presence of HOBT. Alteratively, the coupling can also be effected with a coupling reagent such as BOP in an inert solvent such as dichloromethane. Separation of unwanted side products, and purification of intermediates is achieved by chromatography on silica gel, employing flash chromatography (W. C. Still, M. Kahn, and A. Mitra J. Org. Chem. 1978, 43, 2923), MPLC or preparative TLC.

SCHEME 1

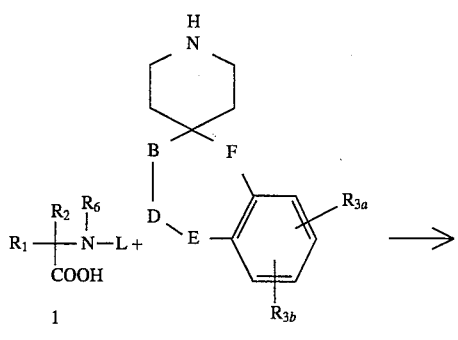

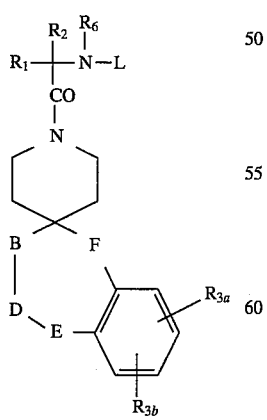

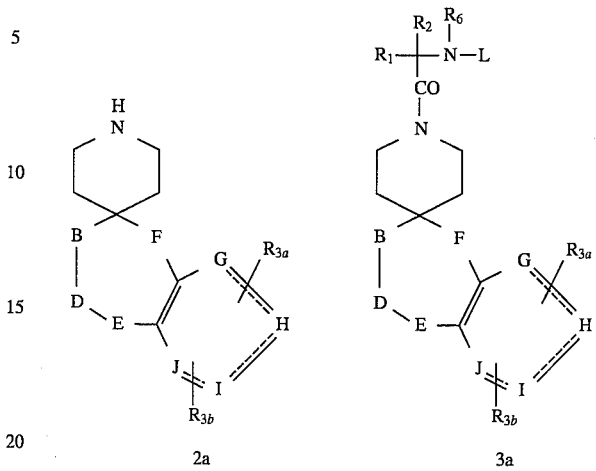

Conversion of 3 and 3a to intermediates 4 and 4a can be carded out as illustrated in Scheme 2. Removal of benzyloxycarbonyl groups can be achieved by a number of methods known in the art; for example, catalytic hydrogenation with hydrogen in the presence of palladium or platinum catalyst in a protic solvent such as methanol. In cases where catalytic hydrogenation is contraindicated by the presence of other potentially reactive functionality, removal of benzyloxy carbonyl groups can also be achieved by treatment with a solution of hydrogen bromide in acetic acid. Removal of BOC protecting groups is carded out in a solvent such as methylene chloride or methanol, with a strong acid, such as hydrochloric acid or trifluoroacetic acid. Conditions required to remove other protecting groups which may be present can be found in Greene, T; Wuts, P.G.M. Protective Groups in Organic Synthesis, John Wiley & Sons, Inc., New York, N.Y. 1991.

SCHEME 2

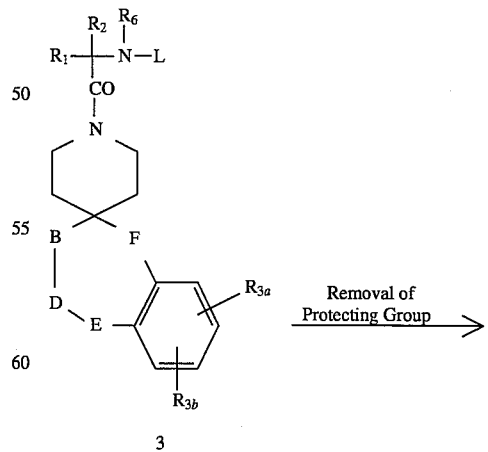

-continued
SCHEME 2

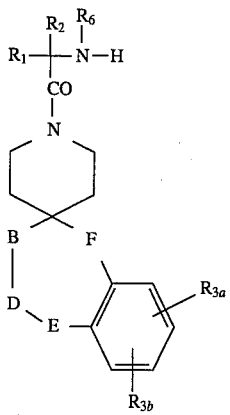

4

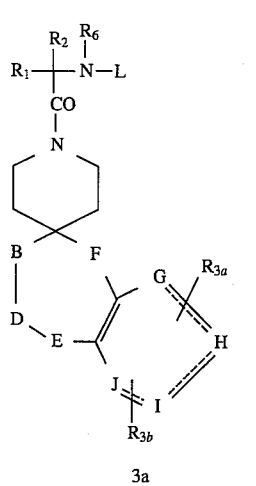

3a

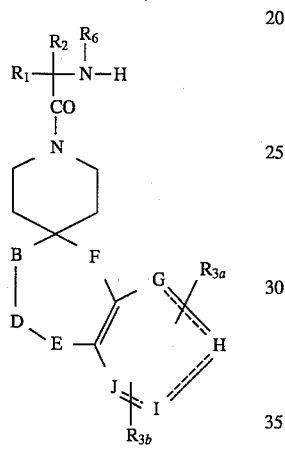

4a solvent such as dichloromethane by a coupling reagent such as EDC or DCC in the presence of HOBT. These amino acids 6 are known amino acids or amino acids readily synthesized by methods known to those skilled in the art. Alteratively, the coupling can also be effected with a coupling reagent such as BOP in an inert solvent such as dichloromethane. Also if $R_4$ or $R_5$ is a hydrogen then amino acids of formula 7 are employed in the coupling reaction, wherein L is a protecting group as defined above, to give 5a and 5c. Deprotection of 5a and 5c (L=protecting group) can be carded out under conditions known in the art.

Intermediates of formula 5 and 5b, wherein A is a methylene or a substituted methylene group, can be prepared as shown in Scheme 3 by coupling of intermediates of formula 4 and 4a to amino acids of formula 6, once again, in an inert

SCHEME 3

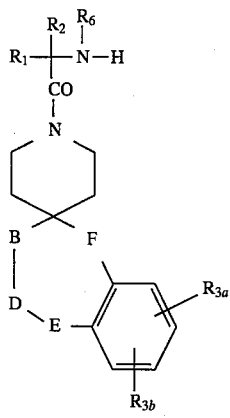

4

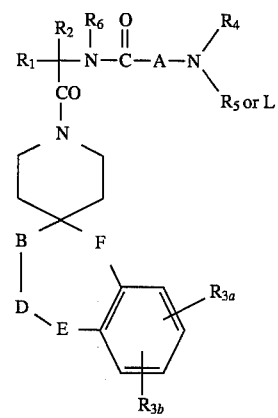

5 and 5a

-continued
SCHEME 3

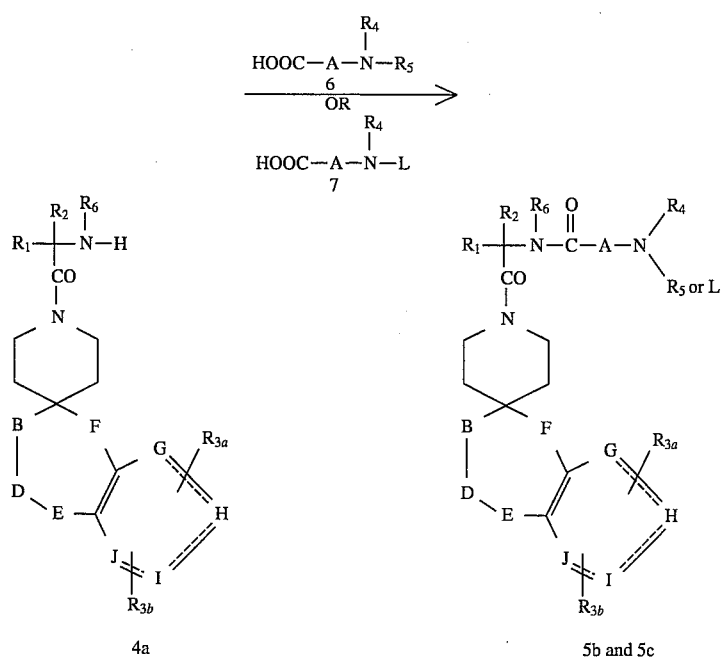

4a          5b and 5c

Compounds of formula I and II wherein $R_4$ and/or $R_5$ is a hydrogen can be further elaborated to new compounds I and II (preferred side chain $R_7=CH_2-CH(OH)-CH_2X$, wherein X=H or OH) which are substituted on the amino group as depicted in Scheme 4. Reductive amination of I and II with an aldehyde is carded out under conditions known in the art; for example, by catalytic hydrogenation with hydrogen in the presence of platinum, palladium, or nickel catalysts or with chemical reducing agents such as sodium cyanoborohydride in an inert solvent such as methanol or ethanol. Alternatively, a similar transformation can be accomplished via an epoxide opening reaction.

SCHEME 4

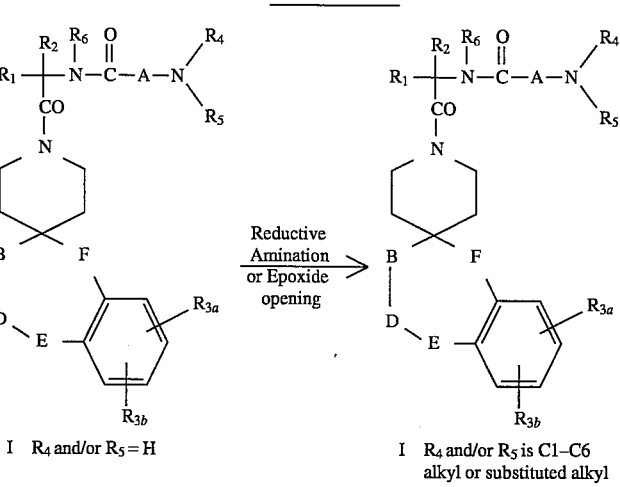

I   $R_4$ and/or $R_5$ = H         I   $R_4$ and/or $R_5$ is C1–C6 alkyl or substituted alkyl -continued
SCHEME 4

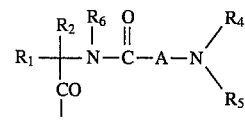

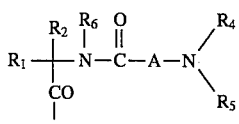

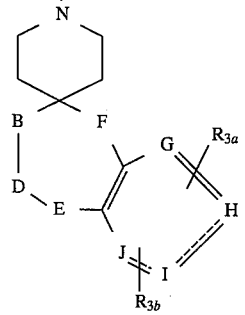

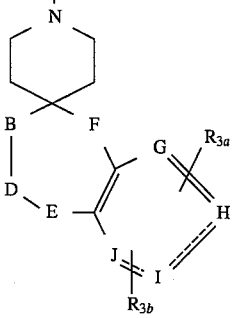

II  R₄ and/or R₅ = H

II  where R₄ and/or R₅ is C1–C6 alkyl or substituted alkyl

Compounds of formula I and II, wherein A is N(R₂)—(CH₂)$_z$—C(R₇)(RT$_{7a}$)—(CH₂)$_y$, can be prepared as shown in Scheme 5 by reacting 4 or 4a with reagents 8, Wherein X is a good leaving group such as Cl, Br, I, imidazole. Alternatively, 4 and 4a can be reacted with an isocyanate of formula 9 in an inert solvent such as 1,2-dichloroethane. If R₄ or R₅ is hydrogen in the final product, the reagents 8 and 9 will bear a removable protecting group L in place of R₄ or R₅.

SCHEME 5

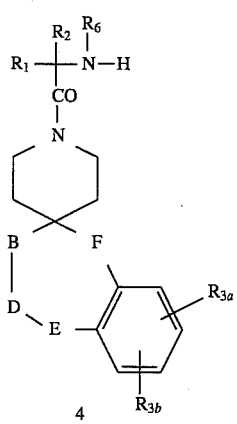

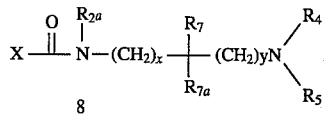

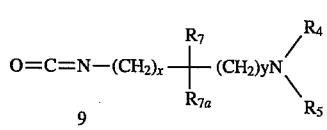

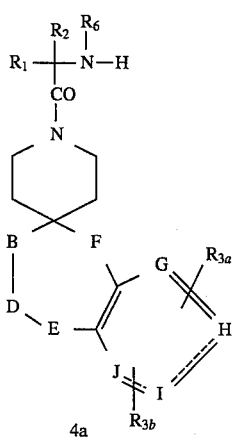

The compounds I and II of the present invention can also be prepared in a convergent manner as described in reaction schemes 6, 7 and 8.

The protected amino acid derivatives 10 are, in many cases, commercially available where M=methyl, ethyl, or benzyl esters. Other ester protected amino acids can be prepared by classical methods familiar to those skilled in the art. Some of these methods include the reaction of a protected amino acid with a diazoalkane and removal of a protecting group L, the reaction of an amino acid with an appropriate alcohol in the presence a strong acid like hydrochloric acid or p-toluenesulfonic acid. Synthetic routes for the preparation of new amino acids are described in Schemes 14, 15, and 16.

Intermediates of formula 11 and 11a, can be prepared as shown in Scheme 6 by coupling of amines 10 to amino acids 6 and/or 7, wherein L is a protecting group, as described above in Scheme 3. When a urea linkage is present in 11 or 11a, it can be introduced as illustrated in Scheme 5.

Acid 12 or 12a can then be elaborated to 5 & 5a and 5b & 5c as described in Scheme 8. Coupling of spiro piperidines of formula 2 and 2a to acids of formula 12 or 12a, wherein L is a suitable protecting group, is conveniently carded out in an inert solvent such as dichloromethane by a coupling reagent such as dicylohexyl carbodiimide (DCC) or EDC in the presence of 1-hydroxybenztriazole (HOBT). Alteratively, the coupling can also be effected with a coupling reagent such as benzotriazol-1-yloxytris(dimethylamino) phosphonium hexafluorophosphate ("BOP") in an inert solvent such as dichloromethane. Transformation of 5a & 5c to I and II is achieved by removal of the protecting group L. When $R_4$ and/or $R_5$ is H, substituted alkyl groups may be optionally added to the nitrogen atom as described in Scheme 4.

SCHEME 6

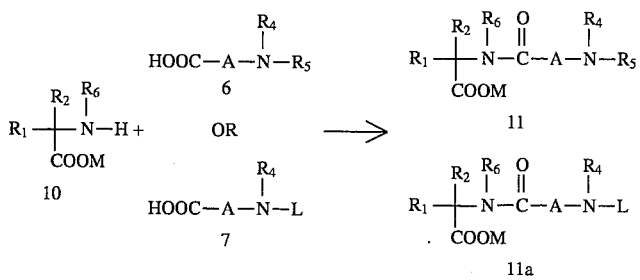

Conversion of the ester 11 or 11a to intermediate acids 12 or 12a can be achieved by a number of methods known in the art as described in Scheme 7; for example, methyl and ethyl esters can be hydrolyzed with lithium hydroxide in a protic solvent like aqueous methanol. In addition, removal of benzyl group can be accomplished by a number of reductive methods including hydrogenation in the presence of platinum or palladium catalyst in a protic solvent such as methanol. An allyl ester can be cleaved with tetrakistriphenylphosphine palladium catalyst in the presence of 2-ethylhexanoic acid in a variety of solvents including ethyl acetate and dichloromethane (see J. Org. Chem. 1982, 42,587).

SCHEME 7

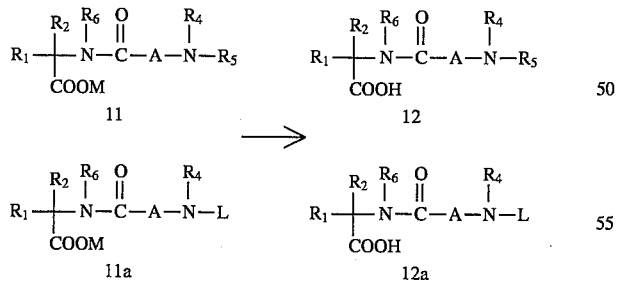

SCHEME 8

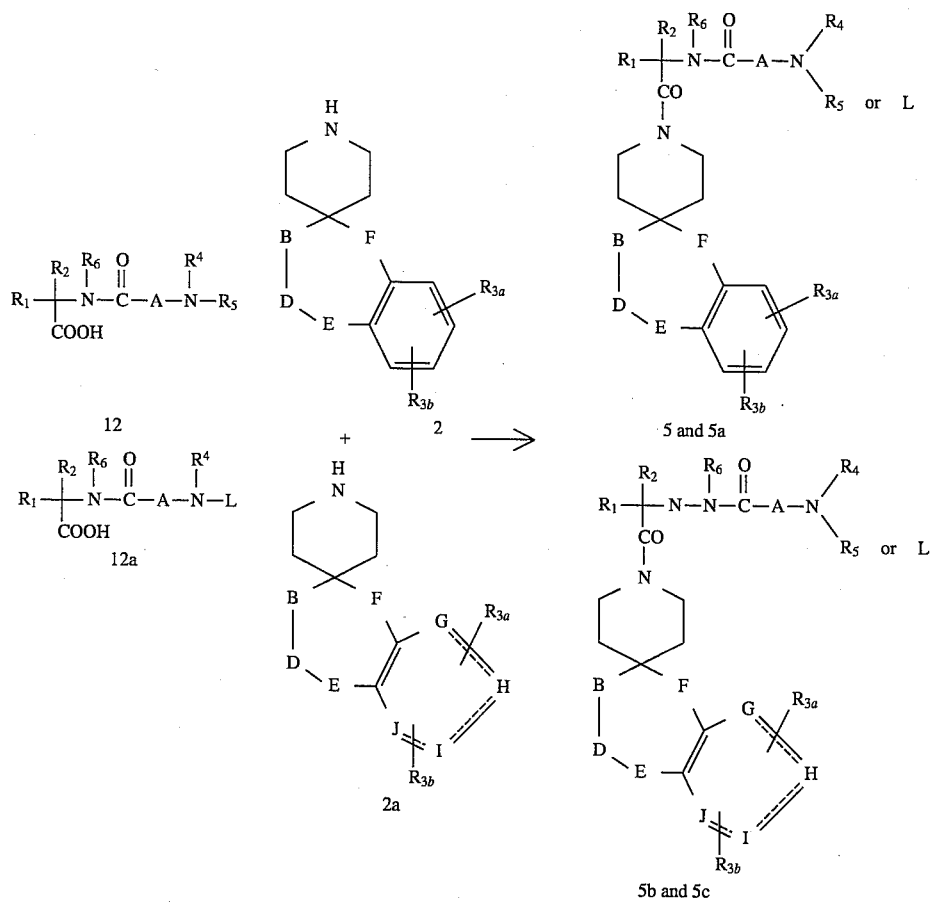

The preparation of oxygenated spiroindanyl piperidine intermediates is illustrated in scheme 9 in which $R_{3a}$ and $R_{3b}$ are both hydrogens. Hydroboration of the protected spiroindene 13 followed by oxidative workup with pyridinium chlorochromate provides the spiroindanone 14.

SCHEME 9

Conversion of spiroindanes into benzolactam intermediates is illustrated in Scheme 10. The treatment of the spiroindanone with hydrazoic acid in an inert solvent such as chloroform (Schmidt reaction) is one of the many suitable literature methods for this transformation. A mixture of two benzolactams is formed in this example. The isomers are easily separated by chromatography on silica gel. These intermediates can then be deprotected and incorporated into growth hormone secretagogues as depicted in Schemes 1 and 8 utilizing generic intermediate 2.

SCHEME 10

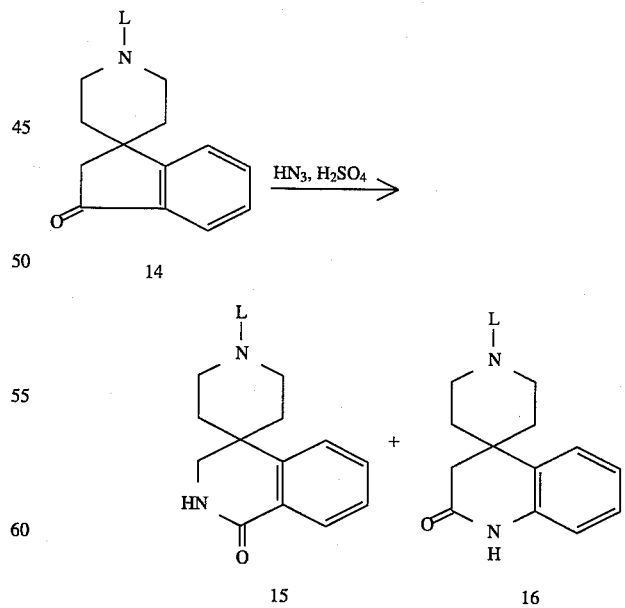

Alkylation of 15 and 16 with an alkyl halide in a solvent such as DMF in the presence of NaH afford 17 and 18 ($R_2$=$C_1$-$C_4$ alkyl).

SCHEME 10A 15 or 16 $\xrightarrow[\text{DMF}]{\text{R}_2\text{X, NaH}}$

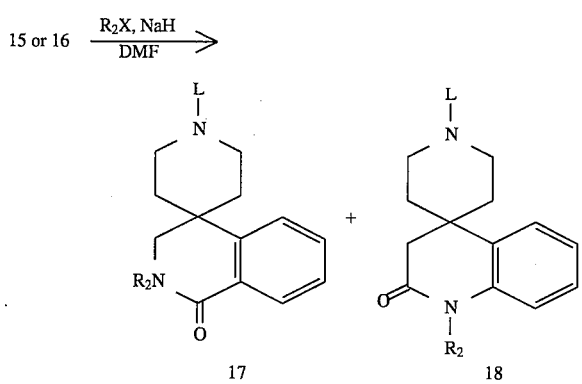

When L is an appropiate protecting group such as a benzyl group the amides can be reduced with lithium aluminum hydride to provide the amines 19 and 21. These amines where $R_2$=H can then be alkylated, arylated, acylated, or reacted with substituted sulfonyl halides or isocyanates employing conditions known to those skilled in the art to afford compounds 20 and 22. Removal of the protecting group (L) by hydrogenolysis using a palladium catalyst provides intermediates that can be incorporated into the secretagogues of this invention using the chemistry illustrated in Schemes 1 and 8 shown above which utilize generic intermediate 2.

SCHEME 11

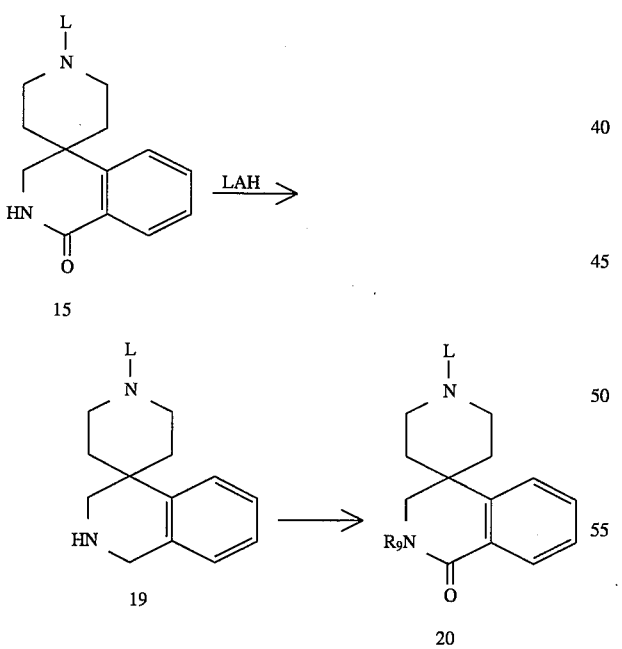

SCHEME 11A

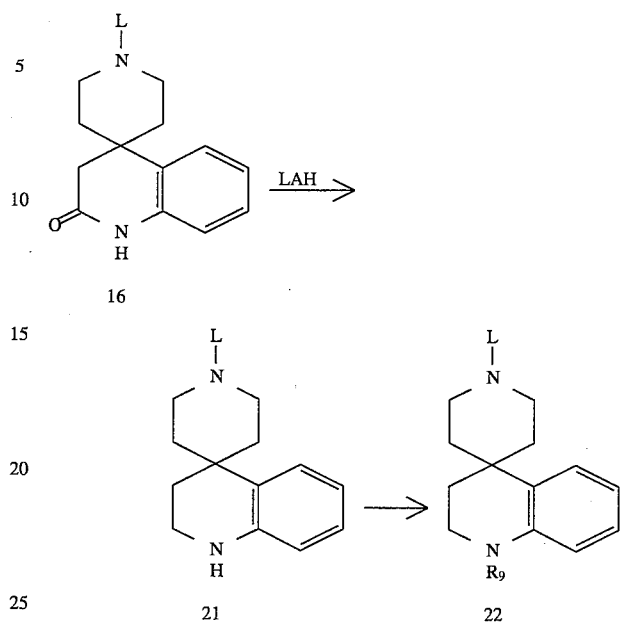

Alternatively, the 1,2,3,4-tetrahydrospiro[isoquinolin-4, 4'-piperidine]ring system can be prepared as outlined in Scheme 12. The ozonolysis of the protected spiroindene followed by dimethyl sulfide treatment gives a hemiacetal intermediate 24 which under reductive amination and acylation conditions provides amine 25. The amino protecting group (L) has been defined above.

SCHEME 12

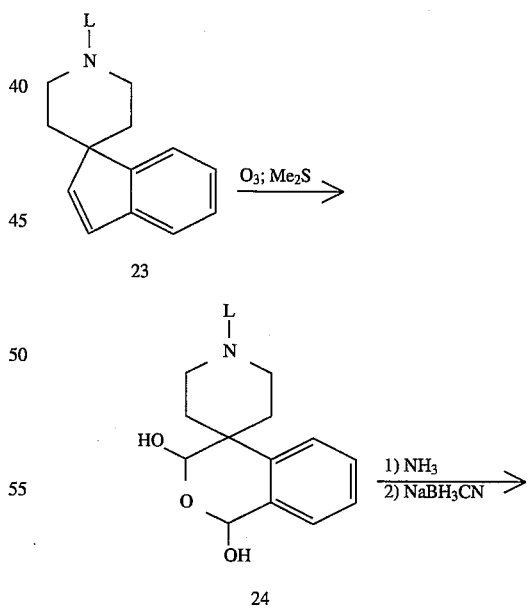

-continued
SCHEME 12

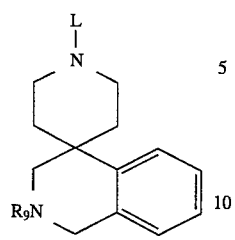

25

The ring analogs of formula 26, where X, Y is H,H; OH,H; H,OH; and =O may be prepared by methods described in the literature and known to those skilled in the art. For example, as illustrated in Scheme 13, the spiro[2H-1-benzopyran-2,4'-piperidine]analog can be prepared from a substituted or unsubstituted 2-hydroxyacetophenone and a properly protected 4-piperidone as described by Kabbe, H. J. Synthesis 1978, 886–887 and references cited therein. The 2-hydroxyacetophenones, in turn, are either commercially available or can be prepared by routes in the literature known to those skilled in the art. Such methods are described by Chang, C. T. et al, in J. Am. Chem. Soc., 1961, 3414–3417. and by Elliott, J. M. et al, in J. Med. Chem. 1992, 35, 3973–3976. Removal of the protecting group as described in: Protective Groups in Organic Synthesis, Greene, T. W., Wuts, P. G., John Wiley & sons, New York, 1991, and Olofson, R. A. et al, J. Org. Chem. 1984, 49, 2081–2082, provides the amine which then can be incorporated into a growth hormone secretagogue via the chemistry detailed in Schemes 1 and 8 shown above which utilize generic intermediate 2.

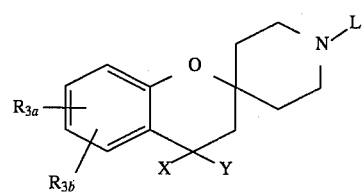

SCHEME 13

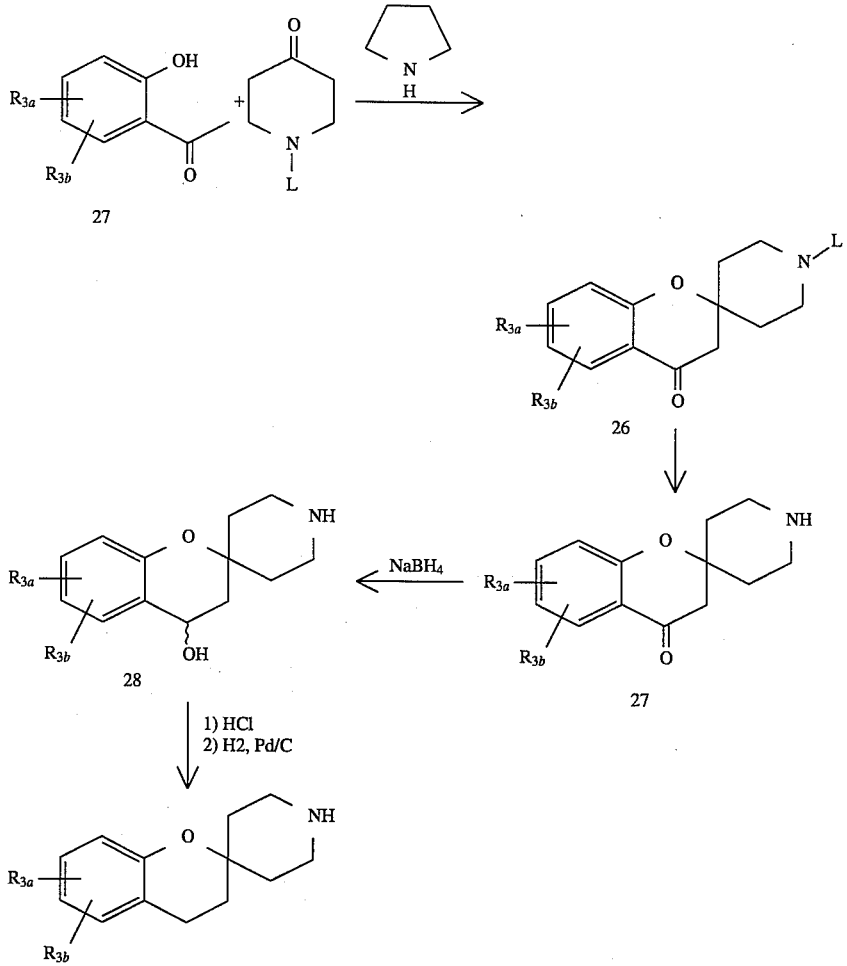

The ketone functionality in compounds of general structure 27 may be reduced to an alcohol using sodium borohydride or may be fully reduced to a methylene also employing conditions known to those skilled in the art. For example, reduction of the ketone with sodium borohydride, followed by treatment with concentrated hydrochloric acid and hydrogenation yield compounds with general structure 29. The amine of structure 27, 28, or 29 can then be incorporated into a growth hormone secretagogue via the chemistry detailed in Schemes 1 and 8 utilizing generic formula 2. Alternatively, the ketone can often be reduced after incorporation into the compounds of Formula I.

Preparation of chiral hydroxyspiro[2H-1-benzopyran-2,4'-piperidine]analogs can be achieved using optically active reducing agents and the crystallization of diastereomeric salts.

The compounds of formulas I and II of the present invention are prepared from a variety of substituted natural and unnatural amino acids such as those of formulas 30 and 6 and 7 where A is —$(CH_2)_x$—$C(R_7)(R_{7a})$—$(CH_2)_y$—. The preparation of many of these acids has been described in the U.S. Pat. No. 5,206,237. The preparation of these intermediates in racemic form is accomplished by classical methods familiar to those skilled in the art (Williams, R. M. "Synthesis of Optically Active α-Amino Acids" Pergamon Press: Oxford, 1989; Vol. 7). Several methods exist to resolve (DL)—

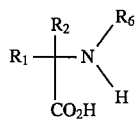

amino acids. One of the common methods is to resolve amino or carboxyl protected intermediates by crystallization of salts derived from optically active acids or amines. Alternatively, the amino group of carboxyl protected intermediates can be coupled to optically active acids by using chemistry described earlier. Separation of the individual diastereomers either by chromatographic techniques or by crystallization followed by hydrolysis of the chiral amide furnishes resolved amino acids. Similarly, amino protected intermediates can be converted to a mixture of chiral diastereomeric esters and amides. Separation of the mixture using methods described above and hydrolysis of the individual diastereomers provides (D) and (L) amino acids. Finally, an enzymatic method to resolve N-acetyl derivatives of (DL)amino acids has been reported by Whitesides and coworkers in J. Am. Chem. Soc. 1989, 111, 6354–6364.

When it is desirable to synthesize these intermediates in optically pure form, some established methods include: (1) asymmetric electrophilic amination of chiral enolates (J. Am. Chem. Soc. 1986, 108, 6394–6395, 6395–6397, and 6397–6399), (2) asymmetric nucleophilic amination of optically active carbonyl derivatives, (J. Am. Chem. Soc. 1992, 114, 1906; Tetrahedron Lett. 1987, 28, 32), (3) diastereoselective alkylation of chiral glycine enolate synthons (J. Am. Chem. Soc. 1991, 113, 9276; J. Org. Chem. 1989, 54, 3916), (4) diastereoselective nucleophilic addition to a chiral electrophilic glycinate synthon (J. Am. Chem. Soc. 1986, 108, 1103), (5) asymmetric hydrogenation of prochiral dehydroamino acid derivatives ("Asymmetric Synthesis, Chiral Catalysis;" Morrison, J. D., Ed; Academic Press: Orlando, Fla., 1985; Vol 5), and (6) enzymatic syntheses (Angew. Chem. Int. Ed. Engl. 1978, 17, 176).

For example, alkylation of the enolate of diphenyloxazinone 31 (J. Am. Chem. Soc. 1991, 113, 9276) with cinnamyl bromide in the presence of sodium bis(trimethylsilyl)amide proceeds smoothly to afford 32 which is converted into the desired (D)-2-amino-5-phenylpentanoic acid 33 by removing the N-t-butyloxycarbonyl group with trifluoroacetic acid and hydrogenation over a $PdCl_2$ catalyst (Scheme 14)

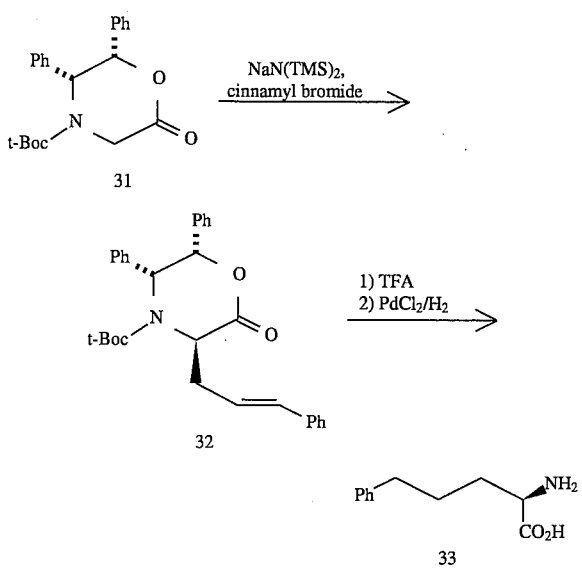

Intermediates of formula 30 which are O-benzyl-(D)-serine derivatives 34 are conveniently prepared from suitably substituted benzyl halides and N-protected-(D)-serine 34. The protecting group L is conveniently a BOC or a CBZ group. Benzylation of 34 can be achieved by a number of methods well known in the literature including deprotonation with two equivalents of sodium hydride in an inert solvent such as DMF followed by treatment with one equivalent of a variety of benzyl halides (Synthesis 1989, 36) as shown in Scheme 15.

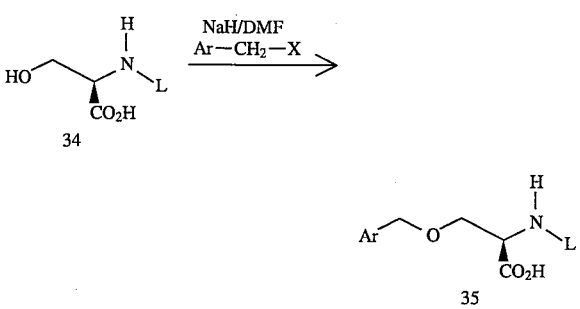

The O-alkyl-(D)-serine derivatives are also prepared using the alkylation protocol shown in Scheme 15. Other methods that could be utilized to prepare (D)-serine derivatives of formula 35 include the acid catalyzed benzylation of carboxyl protected intermediates derived from 34 with reagents of formula $ArCH_2OC(=NH)CCl_3$ (O. Yonemitsu et al. Chem. Pharm. Bull. 1988, 36, 4244). Alternatively, alkylation of the chiral gylcine enolates (J. Am. Chem. Soc. 1991, 113, 9276; J. Org. Chem. 1989, 54, 3916) with $ArCH_2OCH_2X$ where X is a leaving group affords 35. In addition D,L-O-aryl(alkyl)serines can be prepared and resolved by methods described above.

The alkylation of N-protected-(D)-cysteine 36 is carried out by the procedure described in the (D)-serine derivative synthesis and illustrated below with $R_{1a}$-X where X is a leaving group such as halides and mesyloxy groups as shown in Scheme 16.

SCHEME 16

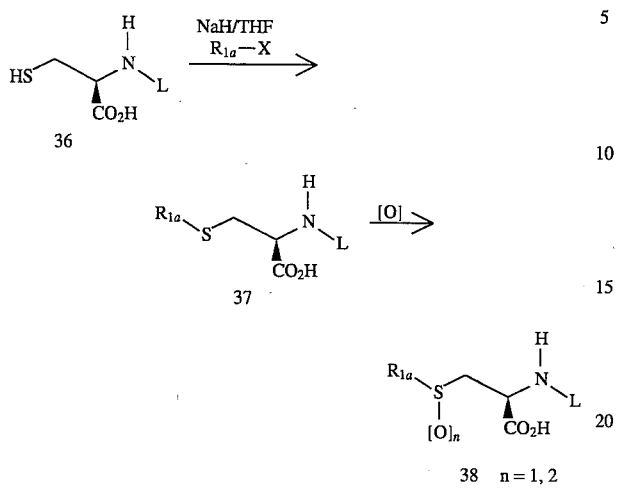

The oxidation of the cysteine derivatives 37 to the sulfoxide 38 (n=1) and the sulfone 38 (n=2) can be accomplished with many oxidizing agents. (For a review of the oxidation of sulfides see Org. Prep. Proced. Int. 1982, 14, 45.) Sodium periodate (J. Org. Chem. 1967, 32, 3191) is often used for the synthesis of sulfoxides and potassium hydrogen persulfate (OXONE) (Tetrahedron Lett. 1981, 22, 1287) is used for the synthesis of sulfones.

Hence, a variety of substituted amino acids may be incorporated into a growth hormone secretagogue via the chemistry detailed in Schemes 1 and 8. The secretagogues that contain a sulfoxide or a sulfone functional group can also be prepared from the cysteine secretagogues by using sodium periodate or OXONE®. Alternatively hydrogen peroxide may be used as the oxidizing reagent in the last step of the synthesis as shown in Scheme 17. The sulfoxide 40 (n=1) and sulfone 40 (n=2) analogs can be separated by preparative thin layer chromatography.

SCHEME 17

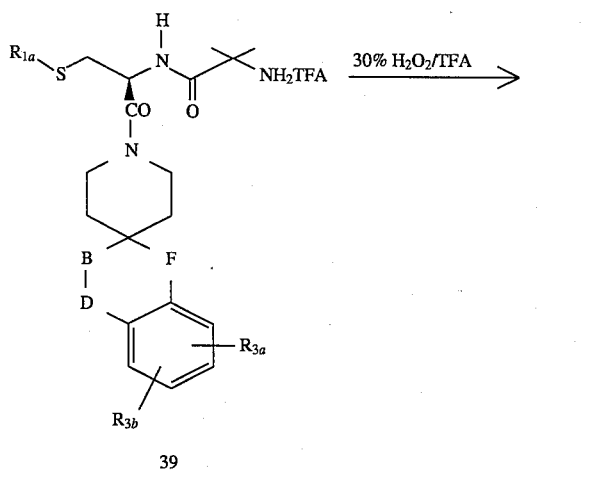

-continued
SCHEME 17

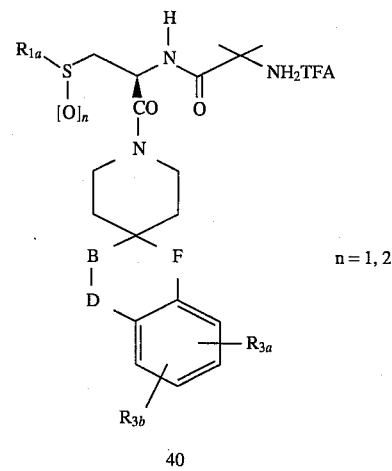

Removal of amino protecting groups can be achieved by a number of methods known in the art; as described above and in *Protective Groups in Organic Synthesis* T. W. Greene, John Wiley and Sons, NY. 1981.

Compounds of formula I wherein $R^4$ and $R^5$ are each hydrogen can be further elaborated by reductive alkylation with an aldehyde by the aforementioned procedures or by alkylations such as by reaction with various epoxides. The products, obtained as hydrochloride or trifluoroacetate salts, are conveniently purified by reverse phase high performance liquid chromatogrphy (HPLC) or by recrystallization.

The spiro piperidines of formula 41 can be prepared by a number of methods, including the syntheses as described below.

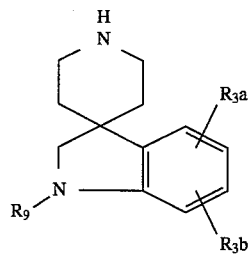

The spiropiperidines of formula 42, wherein L is a defined protecting group, can be synthesized by methods that are known in the literature (for example H. Ong et al J. Med. Chem. 1983, 23, 981–986). The indoline nitrogen of 42, wherein L is a protecting group such as methyl or benzyl, can be reacted by with a variety of electrophiles to yield spiro piperidines of formula 43, wherein $R_9$ can be a variety of functionalities. Compound 42 can be reacted with, for example, isocyanates in an inert solvent like dichloromethane to yield urea derivatives, chloroformates in an inert solvent like dichloromethane to yield carbamates, acid chlorides,

SCHEME 18

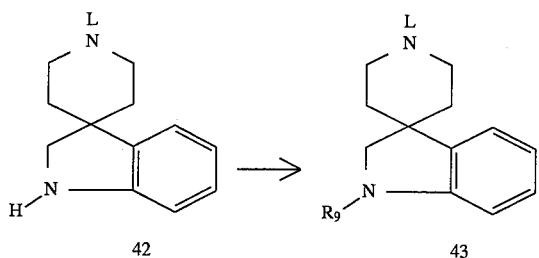

anhydrides, or acyl imidazoles to generate amides, sulfonyl chlorides to generate sulfonamides, sulfamyl chlorides to yield sulfamides. Also, the indoline nitrogen of 42 can be reductively alkylated with aldehydes with conditions known in the art. When the aldehyde used in the reductive amination reaction is a protected glyoxylic acid of structure HCOCOOM, wherein M is a defined protecting group, M can be removed from the product and further derivatized. Alternatively, 42 can be reacted with epoxides to produce 43, wherein $R_9$ is β-hydroxy-substituted alkyl or arylalkyl groups. The indoline 42 can also be transformed to compounds of formula 43, wherein $R_9$=phenyl or substituted phenyl, heteroaryl or substituted heteroaryl, by carrying out the reacting 42 with a fluoro phenyl or fluoro heteroaryl reagent. This chemistry is detailed in H. Ong et al J. Med. Chem. 1983, 23, 981–986.

SCHEME 19

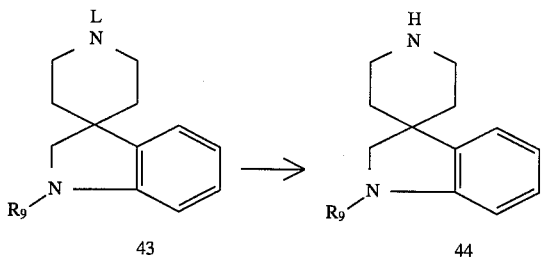

The spiro piperidine intermediate 43 (L=Me or Bn), wherein $R_9$ is hydrogen or most of the derivatives described above, can be demethylated or debenzylated to produce 44, wherein $R_9$ is hydrogen or most of the derivatives described above, as shown in Scheme 19. For compounds of formula 43, wherein L=Me, demethylation can be carded out by a number methods familiar those skilled in the art. For example, demethylation of 43 be accomplished by reacting it with cyanogen bromide and potassium carbonate in an inert solvent solvent such as dichloromethane to yield a cyanamide which can reduced to give 44 by treatment with lithium aluminum hydride in refluxing tetrahydrofuran, refluxing strong acid like aqueous hydrochloric acid, or with Grignard reagents like methyl magnesium bromide. Alternatively, demethylation of 43 can be effected with the ACE-Cl method as described in R. Olofson et al. J. Org. Chem. 1984, 49, 2795 and references therein. For intermediates of formula 43, wherein L=Bn, removal of benzyl group can be accomplished by reductive methods including hydrogenation in the presence of platinum or palladium catalyst in a protic solvent like methanol. Alternatively, debenzylation of 43, L = Bn, can be effected with the ACE-Cl method as described in R. Olofson et al. J. Org. Chem. 1984.

The spiro heterocyclic compounds 45 can be prepared by a number of methods, including the syntheses as described in Scheme 20.

SCHEME 20

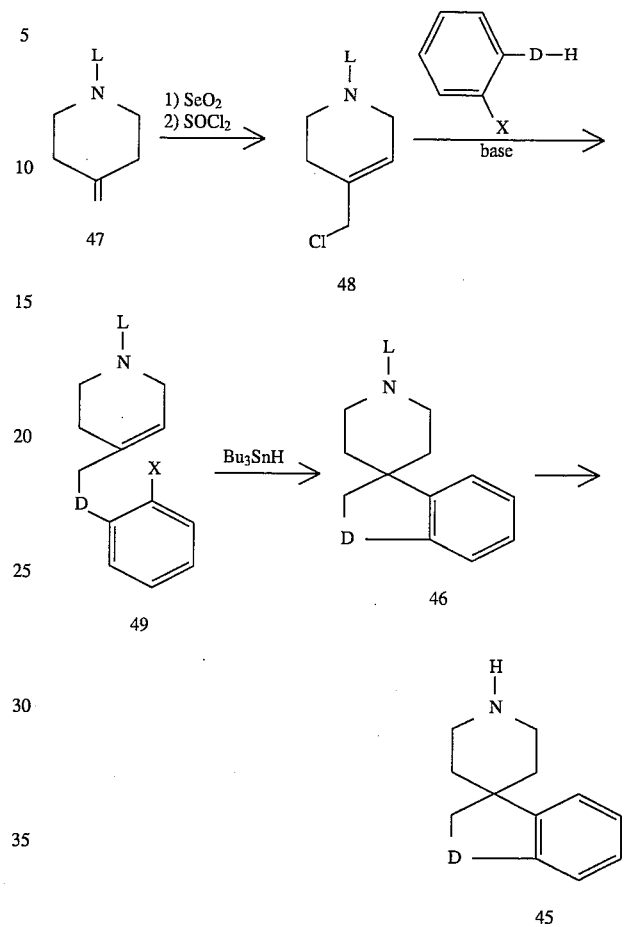

D = O, S, $NR_9$, X = halides, Se, S

Allylic oxidation of the protected piperidine 47 is accomplished by classical methods familiar to those skilled in the art (Rabjohn, N. Org. React. 1976, 24, 261 ). The resulting allylic alcohol is treated with thionyl chloride in an inert solvent such as benzene to provide the corresponding chloride 48. When D=O or S, the alkylation is carried out in DMF or acetone as solvent with potassium carbonate as a base, and when D=$NR_9$ ($R_9$=H, alkyl, aryl, acyl, sulfonyl, carbamate) the reaction is carried out with sodium hydride as a base in an inert solvent such as THF to afford the cyclization precursor 49. When L is a defined protecting group, compound 49 can be cyclized by a number methods familiar to those skilled in the art. For example, cyclization of can be accomplished by reaction with tributyltin hydride (Curran, D. P. Synthesis 1988, 417 and 489) in an inert solvent such as benzene to yield 46. Alternatively, compound 46 (D=$NR_9$) can be prepared by the method shown in Schemes 18 and 19. When D=S, compound 46 can be oxidized to the sulfoxide 47 (n=1) and the sulfone 47 (n=2) by many oxidizing agents (Scheme 21 ). For example, sodium periodate is often used for the synthesis of sulfoxides and OXONE is used for the synthesis of sulfones. Removal of the protecting group provides the amine 45 which then can be incorporated into a growth hormone secretagogue via the chemistry detaileds in Scheme 1 and 8 shown above which utilize genetic intermediate 2.

SCHEME 21

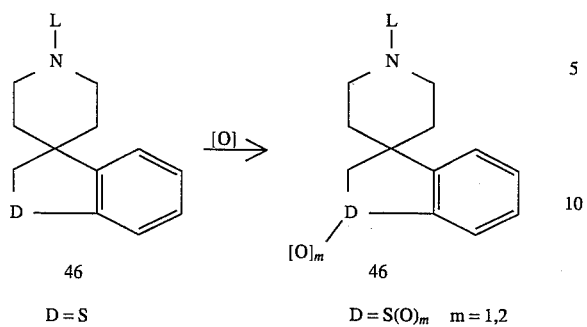

D = S   →[O]→   D = S(O)$_m$  m = 1,2

46                46

The spiro piperidines of formula 50 and formula 51 can be prepared by the syntheses described in Scheme 22.

The phthalimidines of formula 53, where $R_{11}$ is defined as alkyl, aryl, $(CH2)_q$-aryl, or a protecting group, are either commercially available or can be synthesized from the corresponding phthalimides by methods that are known in the literature (for example, Bewster et al in J. Org. Chem., 1963, 28. 501; Mcalees et al J. Chem. Soc., 1977, 2038). The phthalimidine 53 can be alkylated in the presence of a base, such as potassium hydride, lithium or potassium bis(trimethylsilyl)amide, with the protected bis 2-haloethyl amine, where L is a defined protecting group such as methyl, benzyl, t-BOC, or CBZ, etc., and Y could be Cl, Br, I, to yield the spiropiperidine 54. The protecting group could be removed by procedures described above to yield formula 50. Reduction of the lactam in formula 50 by hydrides, such as lithium aluminum hydride, yields formula 51.

SCHEME 22

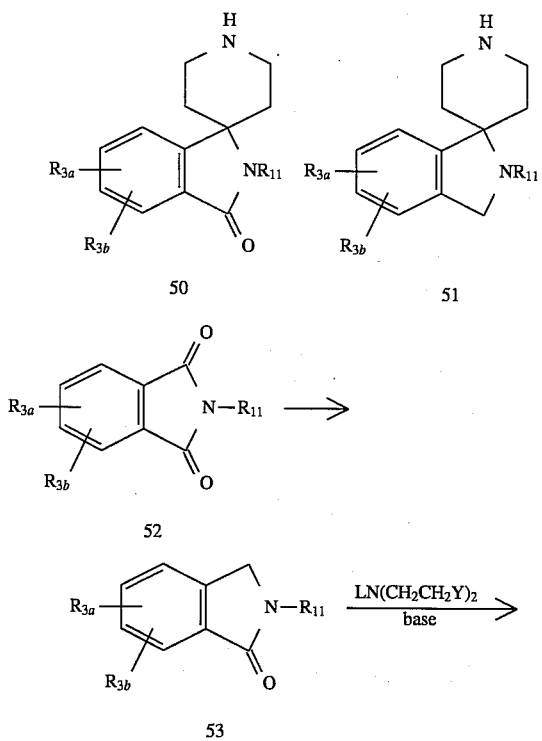

-continued
SCHEME 22

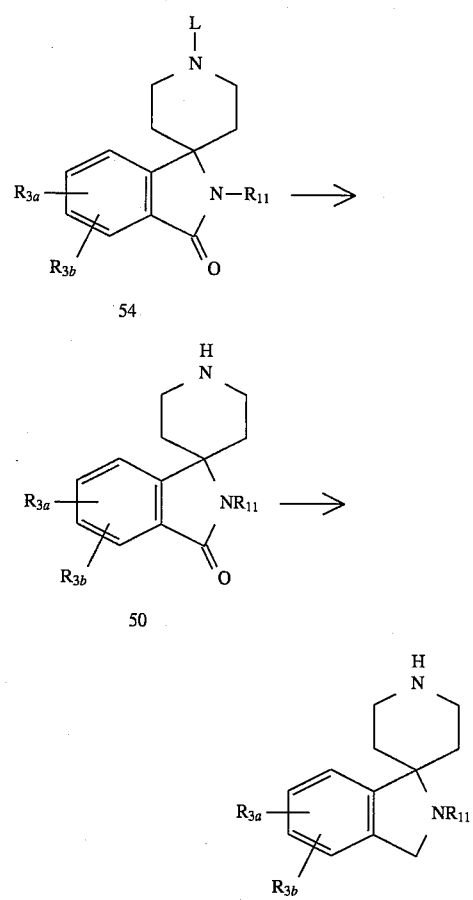

It is noted that the order of carrying out the foregoing reaction schemes is not significant and it is within the skill of one skilled in the art to vary the order of reactions to facilitate the reaction or to avoid unwanted reaction products.

The growth hormone releasing compounds of Formula I and II are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formulas I and II can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I and II can be administered to animals, including man, to release growth hormone in vivo. For example, the compounds can be administered to commercially important animals such as swine, cattle, sheep and the like to accelerate and increase their rate and extent of growth, to improve feed efficiency and to increase milk production in such animals. In addition, these compounds can be administered to humans in vivo as a diagnostic tool to directly determine whether the pituitary is capable of releasing growth hormone. For example, the compounds of Formula I and II can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I and II in association with a pharmaceutical carrier or diluent. Optionally, the active ingredient of the pharmaceutical compositions can comprise an anabolic agent in addition to at least one of the compounds of Formula I and II or another composition which exhibits a different activity, e.g., an antibiotic growth permittant or an agent to treat osteoporosis or in combination with a corticosteroid to minimize the catabolic side effects or with other pharmaceutically active materials wherein the combination enhances efficacy and minimizes side effects.

Growth promoting and anabolic agents include, but are not limited to, TRH, diethylstilbesterol, estrogens, β-agonists, theophylline, anabolic steroids, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the growth hormone secretagogues of this invention is in combination with other growth hormone secretagogues such as the growth hormone releasing peptides GHRP- 6, GHRP-1 as described in U.S. Pat. Nos. 4,411,890 and publications WO 89/07110, WO 89/07111 and B-HT920 as well as hexarelin and the newly discovered GHRP-2 as described in WO 93/04081 or growth hormone releasing hormone (GHRH, also designated GRF) and its analogs or growth hormone and its analogs or somatomedins including IGF-1 and IGF-2 or α- adrenergic aginists such as clonidine or serotonin 5HTlD agonists such as sumitriptan or agents which inhibit somatostatin or its release such as physostigmine and pyridostigmine.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; treating growth hormone deficient adults; prevention of catabolic side effects of glucocorticoids, treatment of osteoporosis, stimulation of the immune system, acceleration of wound healing, accelerating bone fracture repair, treatment of growth retardation, treating acute or chronic renal failure or insufficiency, treatment of physiological short stature, including growth hormone deficient children, treating short stature associated with chronic illness, treatment of obesity and growth retardation associated with obesity, treating growth retardation associated with Prader-Willi syndrome and Tumer's syndrome; accelerating the recovery and reducing hospitalization of burn patients or following major surgery such as gastrointestinal surgery; treatment of intrauterine growth retardation, skeletal dysplasia, hyperconisonism and Cushings syndrome; replacement of growth hormone in stressed patients; treatment of osteochondrodysplasias, Noonans syndrome, sleep disorders, Alzheimer's disease, delayed wound healing, and psychosocial deprivation; treatment of pulmonary dysfunction and ventilator dependency; attenuation of protein catabolic response after a major operation; treating malabsorption syndromes ,reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; to stimulate thymic development and prevent the age-related decline of thymic function; adjunctive therapy for patients on chronic hemodialysis; treatment of immunosuppressed patients and to enhance antibody response following vaccination; improvement in muscle strength, mobility, maintenance of skin thickness, metabolic homeostasis, renal hemeostasis in the frail elderly; stimulation of osteoblasts, bone remodelling, and cartilage growth; treatment of neurological diseases such as peripheral and drug induced neuropathy, Guillian-Barre Syndrome, amyotrophic lateral sclerosis, multiple sclerosis, cerebrovascular accidents and demyelinating diseases; stimulation of the immune system in companion animals and treatment of disorders of aging in companion animals; growth promotant in livestock; and stimulation of wool growth in sheep.

It will be known to those skilled in the art that there are numerous compounds now being used in an effort to treat the diseases or therapeutic indications enumerated above. Combinations of these therapeutic agents some of which have also been mentioned above with the growth hormone secretagogues of this invention will bring additional, complementary, and often synergistic properties to enhance the growth promotant, anabolic and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N.A.T., Role of Bisphosphonates in Metabolic Bone Diseases. Trends in Endocrinol. Metab., 1993, 4, 19–25. Bisphosphonates with these utilities include alendronate, tiludronate, dimethyl - APD, risedronate, etidronate, YM- 175, clodronate, pamidronate, and BM-210995. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg of body weight daily are administered to patients and animals, e.g., mammals, to obtain effective release of growth hormone.

The following examples are provided for the purpose of further illustration only and are not intended to be limitations on the disclosed invention.

EXAMPLE 1

N-[1(R)-[(2', 3'-dihydro-2-oxo,spiro[piperidine-4,4'(1H)-quinolin]-1'yl)carbonyl]-2-(indol-3-yl)ethyl]-2-amino-2-methylpropanamide hydrochloride Step A: 1'-(t-butyloxycarbonyl)3,4-dihydro-3-oxospiro[1H-indene- 1,4'-piperidine]

To a solution of 661 mg (2.31 mmol) of 1'-(t-butyloxycarbonyl)spiro[1H-indene-1,4'-piperidine][prepared by the method of Chambers, et al, J. Med. Chem., 1992, 35, 2036] in 5.0 ml of THF was added 5.8 ml (1.0 M THF, 2.9 mmol) of 9-BBN. The reaction mixture was heated at 70° C. until TLC analysis indicated that the starting material was consumed. The solution was concentrated and the residue was dissolved in dichloromethane. The solution was cooled to 0° C. and 4.1 g (19.2 mmol) of PCC was added slowly over 15 minutes. The reaction mixture was warmed to room temperature and then to reflux for 30 minutes. The solution was then diluted with ether and filtered through a pad of a mixture of celite and florisil. Purification by flash chromotgraphy (silica gel, hexane/ethyl acetate, 4:1) gave 326 mg (47%) of the title compound.

$^1$H NMR (200 MHz, CDCl$_3$): 7.75–7.60 (m, 2 H), 7.50–7.44 (m, 2 H), 4.30–4.15 (m, 2 H), 2.85 (dt, 2 H), 2.63 (s, 2 H), 1.98 (dt, 2 H), 1.53–1.40 (m, 2 H), 1.49 (s, 9 H).

Step B: Spiro[1H-indene-1,4'-piperidin]-3(2H)-one trifluoroacetamide

A solution of the intermediate from Step A in a 1:1:0.5 mixture of trifluoroacetic acid, dichloromethane and anisole was stirred for 1 hour and then concentrated and azeotroped from toluene to give the title compound. $^1$H NMR (200 MHz, CDCl$_3$): 7.81–7.70 (m,1 H), 7.62–7.45 (m, 2 H), 7.22–7.15 (m, 1 H), 3.72–3.58 (m,2 H), 3.29–3.04 (m, 2 H), 2.70 (s, 2 H), 2.47 (dt, 2 H), 1.85–1.75 (m, 2 H).

Step C: Trifluoroacetamide-2,3-dihydrospiro[indene- 1,4'piperidine]

To a solution of 1.0 g (3.21 mmol) of the intermediate obtained in Step B in 3.0 ml of dichloromethane was added 0.945 ml (6.74 mmol) of triethylamine and 50 mg of DMAP and finally 0.501 ml (3.53 mmol) of trifluroacetic acid anhydride. The reaction mixture was stirred for 3 hours and then diluted with 20 ml of dichloromethane. The solution was washed with water, dried over magnesium sulfate, and concentrated. Purification by flash chromatography (silica gel, hexane/ethyl acetate 2:1) gave 568 mg(1.91 mmol).

$^1$H NMR (200 MHz, CDCl$_3$): 7.79–7.64 (m, 2 H), 7.52–7.41 (m, 2 H), 4.75–4.65 (m,1 H), 4.22–4.08 (m, 1 H), 3.37 (dt, 1 H), 2.92 (dt, 1 H), 2.70 (s, 2 H), 2.08 (dt, 2 H), 1.71–1.62 (m, 2 H).

Step D: Triflouroacetamide-3', 4'-dihydro-2-oxospiro[piperidine- 4,4'(1H)-quinoline]

To a solution of 218 mg (3.36 mmol) of sodium azide in 0.285 ml of water and 1.5 ml of chloroform at 0° C. was added 0.105 ml of sulfuric acid. The reaction mixture was stirred for 2.5 hours and then the layers were separated and the chloroform layer was dried over sodium sulfate. The hydrazic acid solution was then added to a solution of 400 mg( 1.34 mmol) of the intermediate obtained from Step A. To this solution was added 0.400 ml of sulfuric acid over 5 minutes. The reaction mixture was stirred for 20 minutes and then for 45 minutes at 45° C. and finally for 16 hours at room temperature. The sulfuric acid layer was added to ice and then made basic with 50% sodium hydroxide. The aqueous layer was extracted with ethyl acetate. The ethyl acetate extracts were dried over sodium sulfate and concentrated. Purification of a 100 mg portion of the crude product by flash chromatography (silica gel, dichloromethane/ethyl acetate 1:1 followed by 1:2) gave 50 mg (0.160 mmol) of a high RF material and 16 mg (0.051 mmol) of a low RF material.

$^1$H NMR (200 MHz, CDCl$_3$, high RF): 8.9–8.7 (bs, 1 H), 7.40–7.21 (m, 2 H), 7.18–7.04 (m, 1 H), 6.90–6.86 (m, 1 H), 4.52–4.36 (m, 1 H), 3.97–3.83 (m, 1 H), 3.52 (tit, 1 H), 3.22 (tit, 1 H), 2.79 (s, 2 H), 2.12–1.66 (m, 4 H). $^1$HNMR (200 MHz, CDCl3, low RF): 8.12( dd, 1 H), 7.60–7.52 (m, I H), 7.45–7.35 (m, 2 H),6.95 (bs, 1 H), 4.56–443 (m,l H), 4.03–3.96 (m,1 H),3.64–3.62 (m,2 H), 3.49–3.35 (m, 1 H), 3.11 (dt, 1 H), 2.20–1.80 (m, 4 H).

Step E: 3', 4'-dihydro-2-oxospiro[piperidine-4,4'(1H)-quinoline]

A solution of 49 mg (0.157 mmol) of the high RF material from Step B in methanol/water 4:1 with excess potassium hydroxide was stirred over night. The solution was concentrated and water and ethyl acetate were added to the residue. The layers were separated and the aqueous layer was extracted with ethyl acetate. The combined organic layers were dried over sodium sulfate and concentrated to give 31 mg (0.143 mmol) of the title compound.

Step F: N-[1(R)-[(2', 3'-dihydro-2-oxo,spiro[piperidine-4, 4'(1H)-quinolin] -1'yl)carbonyl]-2-(indol-3-yl)ethyl]-2-[[1,1 -dimethylethyloxycarbonyl]amino]-2-methylpropanamide To a solution of 29 mg (0.134 mmol) of the intermediate obtained in Step C, 65 mg (0.167 mmol) of 2-amino-N-[ 1 (R)-[2', 3' -dihydro-2-oxospiro[piperidine-4,4'(1'H)-quinolin]-1-yl)carbonyl]-2-( 1H-indol-3-yl)ethyl-2-methylpmpanamide, and 24 mg (0.174 mmol) of HOBT in dichloromethane was added 33 mg (0.174 mmol) of EDC. The reaction was stirred overnight and then worked up and purified as described for Example 1 (Step A) with one exception, dichoromethane/acetone was used for the chromatography. 34.8 mg (0.059 mmol) of the title compound was obtained.

Step G: N-[1(R)-[(2', 3'-dihydro-2-oxo,spiro[piperidine-4, 4'(1H) -quinolin]-1'yl)carbonyl]-2-(indol-3-yl)ethyl]-2-amino-2 -methylpropanamide hydrochloride The title compound (7.2 mg, 0.013 mmol) was obtained from the intermediate from Step D (14 mg, 0.023 mmol) according to the procedure described for Example 1 (Step C) with one exception. The hydrochloride salt was generated from the purified free amine by the addition of 4N HCl in dioxane in this case.

$^1$H NMR (400 MHz, CD$_3$OD, 2:1 mixture of rotomers): 8.34 (d, 2/3 H), 8.27 (d, 1/3H 7.55 (d, 1/3H), 7.38 (d, 1/3H), 7.33 (d, 2/3H), 7.25 (d, 1/3H), 7.18–6.98 (m, 4 H), 6.85 (d, 1/3H), 6.80 (d, 2/3H), 6.68 (d, 1/3H), 5.23–5.17 (m, 1 H), 4.22–4.19 (m, 2/3H), 4.09–3.95 (m, 1/3H), 3.62–3.59 (m, 1/3H), 3.36–3.17 (m, 2 2/3H), 3.08 (dt, 1/3H), 2.75 (dt, 1/3H), 2.69 (dt, 2/3H), 2.48 (dd, 2 H), 1.93–1.75 (m, 2/3H), 1.60 (s, 3 H), 1.58 (s, 2 H), 1.40–1.32 (m, 1 H), 1.51 (s, 1 H), 1.10 (m, 1/3H), 1.02 (m, 2/3H), 0.90 (dt, 2/3H), 0.22 (dt, 2/3 H). FAB-MS: m/e 490 (m+1).

EXAMPLE 2

N-[1(R)-[(2', 3'-dihydro-1-oxospiro[piperidine-4,4'(1H)-isoquinolin]-1'yl )carbonyl]-2-(indol-3-yl)ethyl]-2-amino-2-methylpropanamide hydrochloride Step A: [3', 4'-dihydro-1-oxospiro[piperidine-4,4'(1H)-isoquinoline]

The title compound (11.3 mg, 0.036 mmol) was prepared from the low RF intermediate from Example 1 (Step D) (16.0 mg, 0.051 mmol) according to the procedure described for Example 13 (Step D). $^1$HNMR (200 MHz, CDCl$_3$): 8.12 (dd, 1 H), 7.60–7.52 (m, 1 H), 7.45–7.35 (m, 2 H), 6.95 (bs, 1 H), 4.56–4.43 (m, 1 H), 4.03–3.96 (m, 1 H), 3.64–3.62 (m, 2 H), 3.49–3.35 (m, 1 H), 3.11 (dt, 1 H), 2.20–1.80 (m, 4 H).

Step B: N-[1(R)-[(2', 3'-dihydro-1-oxo,spiro[piperidine-4, 4'(1 H)-isoquinolin]-1'yl)carbonyl]-2-(indol-3-yl)ethyl]-2 -[[1,1dimethylethyloxycarbonyl]amino]-2-methyl -propanamide The title compound (13.6 mg, 0.023 mmol) was prepared from the intermediate from Step A (10.0 mg, 0.032) and 2-amino-N-[1(R)-[2', 3'-dihydro-2-oxospiro[piperidine-4,4' (1'H)-quinolin]-1-yl)carbonyl]-2-(1H-indol-3-yl)ethyl-2-methylpropanamide (21.6 mg, 0.055 mmol) according to the procedure described for Example 13 (Step D).

Step C: N-[1(R)-[(2', 3'-dihydro-1-oxospiro[piperidine-4, 4'(1H) -isoquinolin]-1'yl)carbonyl]-2-(indol-3-yl)ethyl]-2-amino-2 -methylpropanamide hydrochloride A solution of 10.1 mg (0.017 mmol) of the intermediate obtained from Step B in 1.5 N HCl in ethyl acetate was stirred over night and then concentrated and azeotroped from methanol to yield 8.3 mg (0.015 mmol) of the title compound.

$^1$H NMR (400 MHz, CD$_3$OD, 2:1 mixture of rotomers): 7.94 (d, 1/3 H), 7.87 (d, 2/3H), 7.62–7.53 (m, 2 H), 7.40–7.33 (m, 2 1/3H), 7.18–7.10 (m, 3 H), 6.75 (d, 2/3H), 5.22–5.18 (m, 2/3H), 5.15 (t, 1/3H), 4.27–4.23 (m, 2/3H), 4.14–4.10 (m, 1/3H), 3.68–3.61 (m, 1 H), 3.25–3.18 (m, 4 H), 3.10 (dr, 2/3H), 2.87 (dr, 1/3H), 2.70 (dr, 1/3H), 2.65 (dt, 2/3H), 1.88 (dt, 1/3H), 1.75 (dt, 1/3H), 1.62+1.61 +1.59+1.51 (s, 6 H total), 1.57–1.44 (m, I H), 1.38–1.35 (m, 1/3H), 1.15–1.10 (m, 1/3H), 0.929 (dt, 2/3H),0.19 (dt, 2/3H). FAB-MS: m/e 490 (m+1).

EXAMPLE 3

N-[1(R)-[(4H-1-oxospiro[3H-2-benzopyran-3,4'-piperidin]-1'-yl)carbonyl]-2-(indol-3-yl)-ethyl]-2-amino-2-methylpropanamide hydrochloride.

Step A: Spiro[3H-2-benzopyran-3,4'-piperidin]-1(4H)-one

To a suspension of 10% palladium on carbon (5 mg) in ethanol (5 mL) was added of 1'-benzylspiro[3H-2-benzopyran-3,4'-piperidine]-1(4H)-one (20 mg, 0.058 mmol). (Hashigaki et al *Chem. Pharm. Bull.* 32 pg 3561–3568 (1984)). Hydrogenation was performed at 1 atmosphere pressure at room temperature. The reaction was stirred for 2 hours under hydrogen atmosphere, until TLC analysis indicated that the reaction was complete. The catalyst was removed by vacuum filtration through celite 545 and the filtrate was concentrated to give the desired product (12.4 mg, 98.5%).

FAB-MS calc. for $C_{13}H_{15}NO_2$ 217; found 218 (M+H, 100%).

Step B: N-[1(R)-[(4H-1-oxospiro[3H-2-benzopyran-3,4'-piperidin] -1'-yl)carbonyl]-2-(indol-3-yl)-ethyl]-2-[[(1,1-dimethyl -ethyloxy)carbonyl]amino]-2-methylpropanamide A solution of the intermediate from Step A (12 mg, 0.055 mmol) and α(R)-[[2-[[(1,1-dimethylethoxy)carbonyl]amino]-2,2 -dimethyl-1-oxoethyl]amino]-1H-indole-3-propanoic acid (27 mg, 0.058 mmol) in dichloromethane was cooled to 0° C. and then HOBT (2 mg, 0.015 mmol), N-methyl-morpholine (8.8 mg; 0.084 mmol) and EDC (22 mg, 0.12 mmol) were added. The reaction mixture was stirred at room temperature for 1 hour, until the reaction was judged complete by TLC analysis. The solution was then washed with saturated sodium chloride and dried over anhydrous magnesium sulfate. The solution was then filtered and concentrated. Purification by silica gel chromatography provided the title compound (15 mg, 47%). FAB-MS calc. for $C_{33}H_{40}N_4O_6$ 588; Found 589 (M+H, 39%) [489 M+H-100, 42%) loss of t- Boc group].

Step C: N-[1(R)-[(4H-1-oxospiro[3H-2-benzopyran-3,4'-piperidin] -1'-yl)carbonyl]-2-(indol-3-yl )-ethyl]-2-amino-2-methyl -propanamide hydrochloride A solution of the intermediate from Step B (12 mg, 0.02 mmol) in methanol (3 mL) was cooled to 0° C. While stirring, concentrated hydrochloric acid (3 mL) was then added slowly to the mixture. The reaction was stirred for 30 minutes, until TLC analysis indicated that the reaction was complete. The solution was then concentrated several times from toluene. The hydrochloric salt was used without purification (10.15 mg, 96%).

$^1$H NMR (400 MHz, CD$_3$OD): The product exists as a mixture of two conformers (2:1): δ7.977, 7.905 (2d, 2/3H), 7.604–6.994 (m, 8 H), 5.134–5.093 (m, 1 2/3H), Hidden 5.025–4.715 (m, 2 H), 4.191–4.114 (m, 1/3H), 3.637–3.587 (m, 1 H), 3.344–3.299 (m, 1 H), 3.188–3.124 (m, 1 H), 3.030 (s, 2/3H), (dt, 2.81 Hz, 9.4 Hz, 1/3H), 2.536 (q, 1 H), 2.301 (t, 1/3H), 1.590, 1.571 (2s, 6 H), 1.539–1.483 (m, 2/3H), 1.275 (s, 6 H), 1.259–1.206 (m, 2/3H), (m, 1 H), 0.633–0.545 (m, 1/3H), −0.277–0.361 (m, 1/3H).

FAB-MS calc. for C$_{28}$H$_{32}$N$_4$O$_4$ 488; found 489 (M+H, 65%).

EXAMPLE 4

N-[1(R)-[(4', 5'-dihydro-4'-oxospiro[piperidine-4,6'-[6H]thieno[2,3-b]thiopyran]-1-yl)carbonyl]-2-(indol-3-yl)ethyl]-2-amino-2-propanamide hydrochloride Step A: N-[1(R)-[(4', 5'-dihydro-4'-oxospiro[piperidine-4,6'-[6H]thieno[2,3-b]thiopyran]-1-yl)carbonyl]-2-(indol-3-yl)ethyl]-2-[[(1,1 -dimethylethyloxy)carbonyl]amino]-2-propanamide Prepared by the procedure described in Example 3, Step B. Spiro[piperidine-4,6'-[6H]thieno[2,3-b]thiopyran]-4'(5'H)-one hydrochloride, (10 mg, 0.044 mmol) EP publication 90313262.9, α(R)-[[2-[[(1,1-dimethylethoxy)carbonyl]amino]-2,2-dimethyl-1-oxoethyl]amino]-1H-indole-3-propanoic acid (20 mg, 0.051 mmol), HOBT (1 eq.), N-methylmorpholine (0.01 mL, 0.093 mmol), and EDC (20 mg, 0.10 mmol). Reaction time: 5 hours. Yield: 22 mg (98%).

$^1$H NMR (400 MHz, CDCl$_3$): product exists as a mixture of two conformers (2:1): δ8.240 (s, 2/3H), 8.063 (s, 1/3H), 7.680 (d, 2/3H), 7.628 (d, 1/3H), 7.416–6.962 (m, 5 H), 5.279–5.162 (m, 1 H), 4.878–4.763 (m, 1 H), 4.285 (d, 2/3H), 3.376 (d, 2/3H), 3.342–3.196 (m, 1 H), 3.129–2.973 (m, 1 2/3H), 2.715–2.662 (m, 1 H), 2.285 (d, 2/3H), 2.139 (d, 2/3H), 1.683–1.567 (m, 8 1/3H), 1.503, 1.454, 1.427, 1.409 (4s, 12 H), 1.278–1.217 (m, 2 H), 0.708–0.628 (m, 2/3H).

FAB-MS calc. for C$_{31}$H$_{38}$N$_4$O$_5$S$_2$ 610; found 611 (M+H, 32%).

Step B: N-[1(R)-[(4', 5'-dihydro-4'-oxospiro[piperidine-4,6'-[6H]thieno[2,3-b]thiopyran]-1-yl )carbonyl]-2-(indol-3-yl)ethyl]-2-amino-2-propanamide hydrochloride Prepared by the procedure described in Example 15, Step C. The intermediate from previous Step (200 mg, 0.033 mmol) and methanol (3 mL). Reaction time: 1.5 hours. Yield: 12.2 mg (69%).

$^1$H NMR (400 MHz, CD$_3$OD): The product exists as a mixture of two conformers (2:1): δ7.562–7.022 (m, 6 H), 5.513–5.446 (m, 6 2/3H), 5.099–5.003 (m, 1 H), hidden 4.914–4.726 (m, 2/3H), 4.178 (d, 1H), 3.624 (d, 1H), 3.337–3.043 (m, 2 2/3H), 2.760–2.660 (m, 1 H), 2.324 (d, 1H), 2.234 (d, 1H), 1.597, 1.587, 1.574, 1.510 (4s, 4H), 1.364–1.225 (m, 3H), 0.562–0.482 (m, 2/3H), −0.311 −0.391 (m, 2/3H).

FAB-MS calc. for C$_{26}$H$_{30}$N$_4$O$_3$S$_2$ 510; found 511 (M+H, 51%).

EXAMPLE 5

N-[1(R)-[(3-hydrospiro[1H-isobenzofuran-1,4'-piperidin]-1'-yl)carbonyl]-2-(indol-3-yl)ethyl]-2-amino-2-methylpropanamide hydrochloride Step A: N-[1(R)-[(3-hydrospiro[1H-isobenzofuran-1,4'-piperidin] -1'-yl)-carbonyl]-2-(indol-3-yl )ethyl]-2-[[(1,1-dimethyl -ethyloxy)carbonyl]amino]-2-methylpropanamide Prepared by the procedure described in Example 3, Step B. 3-Hydrospiro[1H-isobenzofuran-1,4'-piperidine] hydrochloride (10 mg, 0.044 mmol), (Bauer et al U.S. Pat. No. 3,985,889) α(R)-[[2-[[(1,1-dimethyl-ethoxy)carbonyl]amino]-2,2-dimethyl-1-oxoethyl]amino]-1H-indole-3-propanoic acid (20 mg, 0.051 mmol), HOBT (1 eq.), N-methylmorpholine (0.01 mL, 0.093 mmol), and EDC (20 mg, 0.10 mmol). Reaction time: 5 hours. Yield: 21 mg (81%).

The product exists as a mixture of two conformers (1:1): ($^1$H NMR CDCl$_3$): δ5 8.096 (s, 1 H), 7.689 (t, 1 H), 7.341 (d, 1 H), 7.244–6.611 (m, 6 H), 5.288–5.202 (m, 1/2H), 4.945 (br. s, 1/2H), 4.161 (d, 1/2H), 4.003 (d, 1/2H), 3.338 (d, 1/2H), 3.280–3.115 (m, 2 H), 3.005–2.861 (m, 1 H), 2.751 (d, 1/2H), 2.416 (d, 1/2H), 1.787–1.549 (m 3 1/2H), 1.491, 1.461, 1.421, 1.410 (4s, 12 H), 1.281–1.212 (m, 3 H), 0.857 (t, 6 H).

FAB-MS calc. for C$_{32}$H$_{40}$N$_4$O$_5$ 560; found 561 (M+H, 33%).

Step B: N-[1(R)-[(3-hydrospiro[1H-isobenzofuran-1,4'-piperidin] 1'-yl )carbonyl]-2-(indol-3-yl )ethyl]-2-amino-2 -methylpropanamide hydrochloride Prepared by the procedure described in Example 3, Step C. The intermediate from previous Step (20 mg, 0.04 mmol) and methanol (3 mL). Reaction time: 1 hour. Yield: 18.2 mg (93.5%).

$^1$H NMR (400 MHz, CD$_3$OD): The product exists as a mixture of two conformers (1:1): δ7.621–6.568 (m, 8 H), 5.198–5.136 (m, 1 H), hidden 4.856 (br. s, 1 H), 4.098–4.045 (m, 1 H), 3.611–3.499 (m, 1 H), 3.348–3.110 (m, 5 1/2H), 2.987–2.903 (m, 2 1/2H), 2.618 (d, 1/2H), 2.508 (d, 1/2H), 1.691–1.473 (m, 8H), 1.271 (br. s, 2 1/2H), 0.081—0.006 (m, 1/2H).

FAB-MS calc. for C$_{27}$H$_{32}$N$_4$O$_3$ 460; found 461 (M+H, 96%).

EXAMPLE 6

N-[1(R)-[(3,4-dihydro-6-methyl-4-oxospiro[2H-1-benzopyran-2,4'-piperidin]-1'-yl)carbonyl]-2-(indol-3-yl) ethyl]-2-amino-2-methylpropanamide hydrochloride Step A: N-[1(R)-[(3,4-dihydro-6-methyl-4-oxospiro[2H-1-benzopyran- 2,4'-piperidin]-1'-yl)carbonyl]-2-(indol-3-yl)ethyl] -2-[[(1,1 -dimethylethyloxy)carbonyl]amino]-2-methylpropanamide Prepared by the procedure described in Example 3, Step B. 3,4-Dihydro-6-methylspiro[2H- 1 -benzopyran-2,4'-piperidine]-4-one hydrochloride (20 mg, 0.058 mmol), (Hashigaki et al Chem. Pharm. Bull. 32 pg 3561–3568 (1984)) α(R)-[[2-[[(1,1-dimethylethoxy)-carbonyl]amino]-2,2-dimethyl-1-oxoethyl]amino]-1H-indole-3propanoic acid) (32 mg, 0.082 mmol), HOBT (1 eq.), N-methyl morpholine (0.03 mL, 0.28 mmol), and EDC (40 mg, 0.21 mmol). Reaction time: 8 hours. Yield: 34 mg (86%).

$^1$H NMR (400 MHz, CDCl$_3$): The product exists as a mixture of two conformers (2:1): δ8.154 (s, 2/3H), 8.088 (s, 1/3H), 7.626 (d, 2/3 H), 7.591–7.060 (m, 6 H), 6.725–6.688

(m, 2/3H), 5.265–5.168 (m, 2/3H), 4.985–4.900 (m, 2/3H), 4.289–4.178 (m, 2/3H), 3.469 (s, 2/3 H), 3.229–3.064 (m, 2 2/3H), 2.730 (t, 2/3H), 2.562 (s, 2 1/3H), 2.251 (d, 2 1/3H), 2.158 (d, 2/3H), 2.068 (d, 2/3H), 1.680–1.541 (m, 3 H), 1.502, 1.475, 1.454, 1.427, 1.402 (5s, 15 H), 1.292–1.226 (m, 3 H), 0.616–0.532 (m, 1/3H), −0.495 −0.590 (m, 1/3H). FAB-MS calc. for $C_{34}H_{42}N_4O_6$ 602; found 603. (M+H, 37%).

Step B: N-[1(R)-[(3,4-dihydro-6-methyl-4-oxospiro[2H-1-benzopyran- 2,4'-piperidin]-1'-yl)carbonyl]-2-(indol-3-yl) ethyl]-2-amino-2-methylpropanamide hydrochloride Prepared by the procedure described in Example 3, Step C. The intermediate from previous Step (20 rag, 0.029 mmol) and methanol (3 mL). Reaction time: 3 hours. Yield: 17.5 mg (96.5%).

$^1$H NMR (400 MHz, CDCl$_3$): The product exists as a mixture of two conformers (2:1): δ7.550–6.768 (m,7 1/3H), 5.089–5.016 (m, 2 H), hidden 4.872–4.679 (m, 1 H), 4.144–4.093 (m, 1 H), 3.569–3.485 (m, 1 H), 3.321–3.081 (m, 2 1/3H), 2.716–2.600 (m, 1 1/3H), 2.253, 2.236, 2.222, 2.196, 2.190, 2.155 (6s, 4 H), 1.569, 1.541, 1.475 (3s, 7 H), 1.388–1.237 (m, 3 2/3H), 0.881–0.808 (m, 2 H), 0.434–0.420 (m, 2/3 H), 0.427–0.436 (m, 2/3H).

FAB-MS calc. for $C_{29}H_{34}N_4O_4$ 502; found 503 (M+H, 97%).

EXAMPLE 7

N-[1(R)-[(3,4-dihydro-4-oxospiro[2H-1-benzopyran-2,4'-piperidin]-1' -yl)carbonyl]-4-phenylbutyl-2-amino-2-methylpropanamide hydrochloride Step A: α(R)-[[2-[[(1,1-dimethylethyloxy)carbonyl]amino]-2,2 -dimethyl-1-oxoethyl]amino]-4-phenylbutanoic acid, phenylmethyl ester A dichloromethane solution of 2(R)-amino-4-phenylbutanoic acid, phenylmethyl ester, toluenesulfonic acid salt (6.0 g, 13 mmol) was extracted with dilute sodium hydroxide solution. The organic layer was dried over MgSO$_4$ and evaporated to give a residue. To the solution of the residue, N-tert-butyloxycarbonyl-α-methylalanine (3.21 g, 15.8 mmol), HOBT (1.7 g, 13 mmol) in dichloromethane was added EDC (5.1 g, 26 mmol) and the mixture was stirred overnight at room temperature. The mixture was then poured into a mixture of brine and 3 N HCl and extracted with ethyl acetate. The organic extract was dried, evaporated, and purified by flash column chromatography, eluting with 40% ethyl acetate in hexane, to give the desired product (5.47 g, 91%).

$^1$H NMR (400 MHz, CDCl3): δ7.34–7.07 (m, 10 H), 5.15 (d, $J_{AB}$=12 Hz, 1 H), 5.08 (d, $J_{BA}$=12 Hz, 1 H), 4.86 (br. s, 1 H), 4.67–4.62 (m, 1 H), 2.61–2.53 (m, 2 H), 2.18–2.14 (m, 1 H), 2.01–1.96 (m, 1 H), 1.47 (s, 3 H), 1.43 (s, 3 H), 1.41 (s, 9 H).

Step B: α(R)-[[2-[[(1,1-dimethylethyloxy)carbonyl]amino]-2,2 -dimethyl-1-oxoethyllamino]-4-phenylbutanoic acid The intermediate from previous Step (5.37 g, 11.8 mmol) was hydrogenated at room temperature and 1 atm of H$_2$ using 10% palladium on carbon as catalyst (0.5 g) for 2 hours. The catalyst was filtered through celite and evaporated to give the title compound (4.22 g, 100%).

1H NMR (200 MHz, CD$_3$OD): δ7.804–7.143 (m, 5 H), 4.402–4.359 (m, 1 H), 2.672 (dt, 2 Hz, 6 Hz, 2 H), 2.126–2.004 (m, 2 H), 1.483, 1.444 (2s, 5 H), 1.423 (s, 9 H), 1.412 (s, 3 H).

Step C: N-[1(R)-[(3,4-dihydro-4-oxospiro[2H- 1-benzopyran-2,4'-piperidin]-1'- yl)carbonyl]-4-phenylbutyl-2-[[(1,1 -dimethylethyloxy)carbonyl]amino]-2-methylpropanamide A solution of spiro[2H-1-benzopyran-2,4'-piperidin]-4(3H)-one (20 mg, 0.0.776) and the intermediate from previous Step (31 mg, 0.085 mmol) in dichloromethane was cooled to 0° C. and then HOBT (1 eq.), N-methylmorpholine (0.1 mL, 0.90 mmol) and EDC (33 mg, 0.17 mmol) were added. The reaction mixture was stirred at room temperature for 3 hours, until the reaction was judged complete by TLC analysis. The solution was then washed with saturated sodium chloride and dried over anhydrous magnesium sulfate. The solution was then filtered and concentrated. Purification by silica gel chromatography provided the title compound (41.6 mg, 95.5%).

$^1$H NMR (400 MHz, CDCl$_3$): The product exists as a mixture of two conformers (1:1): δ7.853–6.925 (m, 9 H), 4.936–4.868 (m, 2 H), 4.355–4.265 (mt, 1 H), 3.605–3.565 (m, 1/2H), 3.388–3.3 18 (m, 1 H), 3.022–2.965 (m, 1 H), 2.686–2.608 (m, 3 H), 2.067–1.948 (m, 2 1/2H), 1.871–1.810 (m, 1 H), 1.580 (br. s, 2 H), 1.503, 1.488, 1.455, 1.411, 1.403 (5s, 15 H), 1.292–1.227 (m, 2 H).

Step D: N-[1(R)-[(3,4-dihydro-4-oxospiro[2H-1-benzopyran-2,4' -piperidin]-1'-yl)carbonyl]-4-phenylbutyl-2-amino-2 -methylpropanamide hydrochloride A solution of intermediate from previous Step (40 mg, 0.071 mmol) in ethyl acetate was cooled to 0° C. Then hydrochloric gas was bubbled into solution for 2 minutes. The reaction was stirred for 15 minutes, until TLC indicated that the reaction was complete. The solution was concentrated and the hydrochloric salt (33.8 mg, 95.5%) was used without purification.

$^1$H NMR(400 MHz, CD$_3$OD): The product exists as a mixture of two conformers ( 1:1 ): δ8.271–8.229 (m, 1 H), 7.799 (dd, 1 ¾ Hz, 7.84 Hz, 1 H), 7.545 (q, I H), 7.289–7.006 (m, 7 H), 4.737–4.703 (m, 1 H), 4.277 (d, 1/2H), 4.186 (d, 1/2H), 3.555–3.292 (m, 1 1/2H), 3.187–3.068 (m, 1 H), 2.809–2.724 (2m, 2 H), 2.633–2.563 (m, 1 H), 2.085–1.927 (m, 3 1/2H), 1.645, 1.639, 1.616 (3s, 6 H), 1.677–1.603 (m, 3H) 1.316–1.279 (m, 2 H).

FAB-MS calc. for $C_{27}H_{33}N_3O_4$ 463; found 464 (M+H, 54%).

EXAMPLE 8

N-[1(R)-[(3,4-dihydro-4-oxospiro[2H-1-benzopyran-2,4'-piperidin]-1'-yl)carbonyl]-2-(phenylmethyloxy)ethyl]-2-amino-2-methylpropanamide hydrochloride Step A: N-[1(R-[3,4-dihydro-4-oxospiro[2H-1-benzopyran-2,4' -piperidin]-1'-yl)carbonyl]-2-(phenylmethyloxy) ethyl]-2 -[[(1,1-dimethylethyloxy)carbonyl]amino]-2 -methyl-propanamide.

A solution of spiro[2H-1-benzopyran-2,4'-piperidin]-4(3H)-one (20 mg, 0.776) and α(R)-[[2-[[(1,1-dimethylethyloxy)carbonyl]-amino]-2,2-dimethyl-1-oxoethyl] amino]-3-(phenylmethyloxy)-3-propanoic acid (32 mg, 0.085 mmol) in dichloromethane was cooled to 0° C. and then HOBT (1 eq.), N-methylmorpholine (0.1 mL, 0.90 mmol) and EDC (33 mg, 0.171 mmol) were added. The reaction mixture was stirred at room temperature for 4 hours, until the reaction was judged complete by TLC analysis. The solution was then washed with saturated sodium chloride and dried over anhydrous magnesium sulfate. The solution was then filtered and concentrated. Purification by silica gel chromatography provided the title compound(40.8 mg, 91%).

FAB-MS calc. for $C_{32}H_{41}N_3O_7$ 579; found 580 (M+H, 23%); [found 480 (M+H-100, 57%) loss of t-Boc protective group].

Step B: N-[1(R-[(3,4-dihydro-4-oxospiro[2H-1-benzopyran-2,4'-piperidin]-1'-yl)carbonyl]-2-(phenylmethyloxy)ethyl]-2-amino-2-methylpropanamide hydrochloride Prepared by the procedure described in Example 3, Step D. The intermediate from previous Step (35 mg, 0.061. mmol) and ethyl acetate (10 mL). Reaction time: 1 hour. Yield: 30.2 mg (97%).

$^1$H NMR (400 MHz, CD$_3$OD): The product exists as a mixture of two conformers (1:1): δ7.800–7.792-(m, 1 H), 7.533–7.578 (m, 1 H), 7.395–7.285 (m, 5 H), 7.088–7.015 (m, 2 H), 5.551–5.107 (m, 1 H), hidden 4.921–4.816 (m, 1 H), 4.535–4.518 (2s, 1 1/2H), 4.295 (d, 1 H), 3.911–3.803 (m, 1 H), 3.717–3.703 (2s, 1 1/2H), 3.499–3.400 (m, 1 H), 3.309–3.291 (4s, 3 1/2H), 3.211–3.051 (m, 1 H), 2.789 (q, 1/2H), 2.633–2.513 (AB q, 1 H), 2.060 (t, 1 H), 1.897 (d, 1/2H), 1.821–1.725 (m, 1/2H), 1.626–1.567 (6s, 6 H), 1.564–1.410 (m, 1/2H), 1.301 (hr. s, 1 1/2H). FAB-MS calc. for C$_{27}$H$_{33}$N$_3$O$_5$ 479; found 480 (M+H, 100%).

EXAMPLE 9

N-[1(R)-[(6-chloro-3H-4-oxospiro[1H-quinazoline-2,4'-piperidin]-1'-yl)carbonyl]-2-(indol-3-yl)ethyl]-2-amino-2-methylpropanamide hydrochloride Step A: N-[1(R)-[(6-chloro-3H-4-oxospiro[1H-quinazoline-2,4'-piperidin]-1'-yl)carbonyl]-2-(indol-3-yl)ethyl]-2-[[(1,1-dimethylethyloxy)carbonyl]amino]-2-methyl-propanamide Prepared by the procedure described in Example 3, Step B. 6-Chlorospiro(piperidine-4,2(1'H)-quinazolin)-4(3H)one hydrochloride (50 mg, 0.17 mmol), α(R)-[[2-[[(1,1-dimethylethoxy)carbonyl]amino]-2,2-dimethyl-1-oxoethyl]amino]-1H-indole-3-propanoic acid (81 mg, 0.21 mmol), HOBT (1 eq.), N-methyl morpholine (1 eq.), and EDC (80 mg, 0.42 mmol). Reaction time: 3 hours. Yield 64.5 mg (60%).

FAB-MS calc. for C$_{32}$H$_{39}$N$_6$O$_5$Cl 623; found 624 (M+H, 29%).

Step B: N-[1(R)-[(6 chloro-3H-4-oxospiro[1H-quinazoline-2,4'-piperidin]-1'-yl)carbonyl]-2-(indol-3-yl)ethyl]-2-amino-2-methylpropanamide hydrochloride Prepared by the procedure described in Example 7, Step D. Intermediate from previous Step (50 mg, 0.08 mmol). Reaction time: 1 hour. Yield: 40 mg (89.5%).

FAB-MS calc. for C$_{27}$H$_{31}$N$_6$O$_3$Cl 523; found 523 (M+H, 71%).

EXAMPLE 10

N-[1(R)-[(1,4-dihydro-4-phenyl-1-oxospiro[3H-2-benzopyran-3,4'piperidin]-1'-yl)carbonyl]-2-(indol-3-yl)-ethyl]-2-amino-2-methylpropanamide hydrochloride Step A: 1,4-Dihydro-4-phenylspiro(3H-2-benzopyran-3,4'-piperidine)-1-one Prepared by the procedure described in Example 3, Step A from 1'-benzyl-1,4-dihydro-4-phenylspiro(3H-2-benzopyran-3,4'-piperidine)-1-one hydrochloride, (8 mg, 0.019 mmol) and ethanol (5 mL). Reaction time: 45 minutes. Yield 5.5 mg (98.5%).

FAB-MS calc. for C$_{19}$H$_{19}$NO$_2$ 293; found 294 (M+H, 93%).

Step B: N-[1(R)-[(1,4-dihydro-4-phenyl-1-oxospiro[3H-2-benzopyran-3,4'-piperidin]-1'-yl)carbonyl]-2-(indol-3-yl)ethyl]-2-[[(1,1-dimethylethyloxy)carbonyl]amino]-2-methylpropanamide Prepared by the procedure described in Example 3, Step B. The intermediate from previous Step (5 mg, 0.017 mmol), α(R)-[[2-[[(1,1-dimethylethoxy)carbonyl]amino]-2,2-dimethyl-1-oxoethyl]amino]-1H-indole-3-propanoic acid (12 mg, 0.030 mmol), HOBT (1 eq.), N-methyl morpholine (1 eq.), and EDC (12 mg, 0.060 mmol). Reaction time: 5 hours. Yield: 9.2 mg (86%).

$^1$H NMR(400 MHz, CD$_3$OD): The product exists as a mixture of two conformers (1:1): δ8.185–8.072 (m, 1 1/2H), 7.885 (s, 1/2H), 7.710– 6.813 (m; 12 H), 5.331–5.309 (m; 1/2H), 5.198–5.111 (m, 1/2H), 4.710–4.605 (m, 1/2H), 4.300–4.235 (m, 1/2H), 3.876 (d, 1/2H), 3.719–3.617 (m, 1 H), 3.355–3.046 (m; 1 1/2H) 2.746 (q, 1/2H), 2.006–1.960 (m, 1 H), 1.678–1.574 (m, 2 H), 1.438, –1.368 (m, 6 H), 1.257, 1.240, 1.227, 1.208, 1.186 (5s, 5 H).

Step C: N-[1(R)-[(1,4-dihydro-4-phenyl-1-oxospiro[3H-2-benzopyran-3,4'-piperidin]-1'-yl)carbonyl]-2-(indol-3-yl)ethyl]-2-amino-2-methylpropanamide hydrochloride Prepared by the procedure described in Example 7, Step D. Intermediate from previous Step (9 mg, 0.015 mmol) and ethyl acetate (10 mL). Reaction time: 1 hour. Yield: 8 mg (97%).

$^1$H NMR(400 MHz, CDCl$_3$): The product exists as a mixture of two conformers (2:1): δ8.347–8.333 (m, 1 H), 8.043 (t, 1/2H), 7.662–6.869 (m, 12 1/2H), 5.355–5.315 (m, 1/2H), 5.108–5.061 (m, 1/2H), hidden 4.897–4.768 (m, 1/2H), 4.174–4.103 (m, 1/2H), 3.717–3.526 (m, 1 H), 3.387–3.237 (m, 2 H), 3.179–3.067 (m, 1 H), 2.660 (q, 1/2H), 2.044–1.981 (m, 1 H), 1.655–1.212 (m, 11 H), 0.964–0.820 (m, 2 1/2 H), 0.575–0.423 (m, 1/2H), –0.271—0.448 (m, 1/2H).

FAB-MS calc. for C$_{34}$H$_{36}$N$_4$O$_4$ 564; found565 (M+H, 25%).

EXAMPLE 11

N-[1(R)-[(3,4-dihydro-4-oxospiro[2H-1-benzopyran-2,4'-piperidine]-1'-yl)carbonyl]-2-(indol-3-yl)ethyl]-2-amino-2-methylpropanamide hydrochloride Step A: N-[1(R)-[(3,4-dihydro-4-oxospiro[2H-1-benzopyran-2,4'-piperidin]-1'-yl)carbonyl]-2-(indol-3-yl)ethyl]-2-[[(1,1-dimethylethyloxy)carbonylaminol-2-methylpropanamide This intermediate was prepared from α(R)-[[2-[[(1,1-dimethylethoxy)carbonyl]amino]-2,2-dimethyl-1-oxoethyl]amino]-1H-indole-3-propanoic acid (903 mg, 2.3 mmol) and spiro[2H-1-benzopyran-2,4'-piperidin]-4(3H)-one, hydrochloride (535 mg, 2.11 mmol) (Elliott, J, et al, J. Med. Chem. 1992, 35, 3973–3976) by the procedure described in Example 25, Step A (1.25 g, 100%).

$^1$H NMR (400 MHz, CDCl$_3$): compound exists as a mixture of conformers (ratio 2:1 ): δ8.42, 8.31 (2s, 1 H), 7.79, 7.75 (2 dd, 1.6 Hz, 7.8 Hz, 1 H), 7.66, 7.56 (2d, 8.0 Hz, 7.6 Hz, 1 H), 7.47–6.78 (m, 8 H), 5.37–5.15 (m, 1 H), 4.98, 4.94 (2 br. s, 1 H), 4.24, 4.18 (2 br. d, 1 H), 3.40, 3.32 (2 br. d, 1 H), 3.23–3.02 (m, 3 H), 2.73 (dt, 3 Hz, 13 Hz, 1 H), 2.47 (d, 2 Hz, 1/3H), 2.17 (d, 16.6 Hz, 2/3H), 2.08 (d, 16.7 Hz, 2/3 H), 1.84 (br. s, 2 H), 1.70–1.60 (br. dd, 1 H), 1.3–1.2 (br. dd, 1 H), 0.56 (dt, 4.6, 13.8 Hz, 2/3H), –0.55 (dr, 4.6, 13.8 Hz, 2/3H). FAB-MS: calc. for C$_{33}$H$_{40}$N$_4$O$_6$. 588; found 595 (M+Li, 100%).

Step B:. N-[1(R)-[(3,4-dihydro-4-oxospiro[2H-1-benzopyran-2,4'-piperidin]-1'-yl)carbonyl]-2-(indol-3-yl)ethyl]-2-amino-2-methylpropanamide hydrochloride To a stirred solution of the intermediate prepared in Step A (1.0 g, 1.7 mmol) in methanol (5 mL) was added concentrated hydrochloric acid (5 mL). The reaction mixture was stirred at room temperature for one hour and 20 mL of toluene was added and the mixture was evaporated in vacuo. This procedure was repeated twice to give the title compound (0.87 g, 98%).

$^1$H NMR (400 MHz, CD$_3$OD): compound exists as a mixture of conformers (ratio 2:1): δ7:76–6.90 (m, 10 H), 5.11 (dd, 5,11 Hz, 1 H), 4.16, 4.11 (2 td, 2.0 Hz, 14 Hz, 1 H), 3.60, 3.33 (2 md, 14 Hz, 1 H), 3.25–3.10 (m, 2 H), 2.92–2.67 (m 2 H), 2.30–2.17 (AB, centered at w.23, 16.7 Hz, 2 H), 2.85–2.80 (br. d, 1/3H), 1.60, 1.59 (2s, 6 H), 1.70–1.50 (m, hidden), 1.40–1.30 (md, 1 H), 0.47 (dt, 5.5, 13.5 Hz, 2/3 H), –0.38 (dr, 5.5, 13.5 Hz, 2/3Hz). FAB-MS: calc. for C$_{28}$H$_{32}$N$_4$O$_4$, 488; found 489 (M+H, 100%).

EXAMPLE 11A

N-[1(R)-[(3,4'dihydro-4(RS)-hydroxyspiro[2H-1-
benzopyran-2,4'-piperidin]-1'-yl)carbonyl]-2-
(indol-3-yl)ethyl]-2-amino-2-methylpropanamide To a stirred solution of the title compound in Example 11 (55 mg, 0.09 mmol) in methanol (5 mL) at 0° C., was added sodium borohydride (16 mg, 0.4 mmol) in several portions. After stirred at 0° C. for 30 minutes the mixture was evaporated to dryness and dissolved in dichloromethane and purified by flash column eluting with 10% methanol in dichloromethane to give the title compound (35 mg, 78%).

$^1$H NMR (400 MHz, CD$_3$OD): compound exists as a mixture of 2 diastereomers (1:1) and each isomer exists as two conformers (ratio 2:1): δ7.89–6.66 (m, 9 H), 5.14–5.06 (m, 1 H), 4.52–4.45 (2 dd, I H), 4.22–4.10 (2 md, I H), 3.58–3.44 (2 md, 1 H), 3.25–3.14 (m, 2 H), 3.10–2.59 (4 dr, 1 H), 2.02 (dd, 6.2, 14.7 Hz, 1/3H), 1.79–1.74 (dd, 1/3H), 1.60–1.40 (m, 3 H), 1.37, 1.31, 1.28, 1.28, 1.26 (4 s, 6 H), 1.3–1.05 (m, hidden), 0.71, 0.49 (2 dt, 5.6, 13.5 Hz, 2/3H), –0.20, –0.47 (2 dt, 4.6, 13.5 Hz, 2/3H). FAB-MS: calc. for C$_{28}$H$_{34}$N$_4$O$_4$, 490; found 491 (M+H, 100%).

EXAMPLE 12

N-[1(R)-[(3,4-dihydro-spiro[2H-1-benzopyran-2,4'-
piperidin]-1'-yl)carbonyl]-2-(indol-3-yl)ethyl]-2-
amino-2-methylpropanamide hydrochloride Step A: 3,4-Dihydrospirol 2H-1-benzopyran-2,4'-piperidine]

To a stirred solution of the spiro[2H-1-benzopyran-2,4'-piperidin]-4(3H)-one, hydrochloride (53 mg, 0.21 mmol) in methanol (5 mL) at 0° C., was added sodium borohydride (38 mg, 1 mmol) in several portions. After 30 minutes the mixture was evaporated and then treated with concentrated hydrochloric acid (2 mL) for 30 min. Evaporation gave a residue which was hydrogenated with palladium on carbon (10%, 10 mg), H$_2$ (1 atm) in ethanol for two hours. Filtration to remove the catalyst gave the crude intermediate (89 mg) which was used without further purification.

$^1$H NMR (400 MHz, CD$_3$OD): 7.07 (appears as d, 5 Hz, 2 H), 6.84 (appears as t, 7 Hz, 2 H), 7.07–7.08 (m, 4 H), 2.82 (t, 7 Hz, 2 H), 2.02 (br. d, 14.5 Hz, 2 H), 1.90–1.85 (m, 4 H). EI-MS: calc. for C$_{13}$H$_{17}$NO, 203; found 203 (M+, 45%)

Step B: N-[1(R)-[(3,4-dihydro-spiro[2H-1-benzopyran-2,4'-
piperidin]-1'-yl)carbonyl]-2-(indol-3-yl)ethyl]-2-[[ (1,1
-dimethylethyloxy)carbonyl]amino]-2-methylpropana-
mide This intermediate was prepared from the product of Step A and α(R)-[[2-[[( 1,1-dimethylethoxy)carbonyl]amino]-2,2-dimethyl- 1-oxoethyl]amino]-1H-indole-3-propanoic acid following standard peptide coupling methods.

$^1$H NMR (400 MHz, CDCl$_3$): compound exists as a mixture of conformers (ratio 2:1): δ8.04, 8.02 (2s, 1 H), 7.70, 7.61 (2d, 8 Hz, 1 H), 7.49–6.66 (m, 1 H), 4.92 (br. s, 1 H), 4.30–4.20 (m, 1 H), 3.4–3.1 (m, 4 H), 2.85–2.45 (m, 3 H), 1.68 (t, 7.6 Hz, 1 H), 1.49, 1.45, 1.44, 1.43, 1.41 (5 s, 12 H), 1.30–1.21 (m, 3 H), 1.11–1.07 (dd, 2.5, 14 Hz, 1/3H), 0.68 (dt, 4.5 Hz, 13 Hz, 1/3H), –0.33—0.43 (dt, 1/3H). FAB-MS: calc. for C$_{33}$H$_{42}$N$_4$O$_5$, 574; found 575 (M+H, 35%).

Step C: N-[1(R)-[(3,4-dihydro-spiro[2H-1-benzopyran-2,4'-
piperidin]-1'-yl )carbonyl]-2-(indol-3-yl )ethyl]-2-
amino-2 -methylpropanamide hydrochloride The title compound was prepared from the intermediate in Step B according to the procedure described in Example 11, Step B. (90%).

$^1$H NMR (400 MHz, CD$_3$OD): compound exists as a mixture of conformers (ratio 2:1): δ8.31, 8.21 (2 d, 6.6 Hz, 2/3H), 7.58, 7.52 (2 d, 7.8 Hz, 1 H), 7.37 (d, 8.2 Hz, 1 H), 7.15–6.60 (m, 6 1/3H), 5.17–5.13 (m, 1 H), 4.14 (br. d, 13.2 Hz, 1 H), 3.35–3.10 (m 3 H), 2.90–2.45 (m, 3 H), 1.70 (t, 6.9 Hz, 1'H), 1.60 (s, 6 H), 1.60–1.40 (m, hidden), 1.40– 1.20 (m, 2 H), 1.11 (br. d, 12.7 Hz, 2/3H), 0.57 (dt, 4.3, 13 Hz, 2/3H), –0.31 (dt, 4.3, 13, 2/3H). FAB-MS: calc. for C$_{28}$H$_{34}$N$_4$O$_3$, 474; found 475 (M+H, 60%).

EXAMPLE 13

N-[1(R)-[(3,4-dihydro-6-methanesulfonylamino-4-
oxo-spiro[2H-1
-benzopyran-2,4'-piperidin]-1'-yl)carbonyl]-2-
(indol-3-yl)ethyl]-2 -amino-2-methylpropanamide
hydrochloride The title compound was prepared from α(R)-[[2-[[( 1,1-dimethylethoxy)carbonyl]amino]-2,2-dimethyl-1-oxoethyl]] amino]-1 H-indole-3-propanoic acid and 3,4-dihydro-6-methanesulfonylamino-4 -oxo-spiro[2H-1-benzopyran-2,4'-piperidine] following procedures described in Example 10, Steps A and B.

N-[1(R)-[(3,4-dihydro-6-methanesulfonylamino-4-oxo-
spiro[2H-1 -benzopyran-2,4'-piperidin]-1'-yl)carbonyl]-2-
(indol-3-yl)ethyl]-2-[[(1,1 -dimethylethyloxy)carbonyl]
amino]-2-methylpropanamide.

$^1$H NMR (400 MHz, CDCl$_3$): compound exists as a mixture of conformers (ratio 2:1 ): δ8.60, 8.36 (2 br. s, 1 H), 7.63–6.81 (m, 8 H), 5.20 (br. s, 1 H), 5.10–5.02 (br. m, 1 H), 3.45–3.30 (br. m, 1 H), 3.25–3.10 (br. m, 2 H), 2.97, 2.95 (2s, 3 H), 2.75–2.56 (m, 1 H), 2.28 (v. br. s, 1 H), 2.18 (d, 16.6 Hz, 1 H), 2.05 (d, 16.6 Hz, 1 H), 1.86–1.45 (m, s hidden), 1.51, 1.46, 1.44, 1.43, 1.42, 1.39 (6 s, 12 H), 1.30–1.20 (m, 2 H), 0.55–0.45 (m, 2/3H), –0.55—0.65 (m, 2/3H). FAB-MS: calc. for C$_{34}$H$_{43}$N$_5$O$_8$S, 681; found 688 (M+Li, 40%).

N-[1(R)-[(3,4-dihydro-6-methanesulfonylamino-4-oxo-
spiro[2H-1 -benzopyran-2,4'-piperidin]-1'-yl)carbonyl]-2-
(indol-3-yl)ethyl]-2 -amino-2-methylpropanamide hydro-
chloride.

$^1$H NMR (400 MHz, CD$_3$OD): compound exists as a mixture of conformers (ratio 2:1 ): δ7.63–6.92 (m, 8 H), 5.14–5.08 (m, 1 H), 4.18– 4.08 (2 mr, 1 H), 3.62–3.51 (2 md, 1 H), 3.25–3.10 (m, 2 H), 2.91, 2.89 (2 s, 3 H), 2.78–2.67 (2 dd, 2 Hz, 15 Hz, 2 H), 2.27 (d, 16.7 Hz, 1 H), 2.19 (d, 16.6 Hz, 1 H), 1.86–1.80 (m, 1/3H), 1.80–1.50 (m, hidden ), 1.60, 1.59, 1.48 (3s, 6 H), 1.40–1.30 (m, 1 H), 0.47 (dt, 4.8 Hz, 13

Hz, 2/3H), −0.39 (dt, 4.8 Hz, 13 Hz, 2/3H). FAB-MS: calc. for $C_{29}H_{35}N_5O_6S$, 581; found 582 (M+H, 75%).

EXAMPLE 14

N-[1(R)-[(3,4-dihydro-4(RS)-hydroxy-6-methanesulfonylaminospiro[2H-1-benzopyran-2,4'-piperidin]-1'-yl)carbonyl]-2-(indol-3-yl)ethyl]-2-amino-2-methylpropanamide The title compound was prepared from the title compound in Example 13 following the procedure described in Example 11A.
$^1$H NMR (400 MHz, CD$_3$OD): compound exists as a mixture of 2 diastereomers (1:1) and each isomer exists as two conformers: δ7.62–7.50 (m, 1 H), 7.42–7.29 (m, 2 H), 7.17–6.98 (m, 4 H), 6.68 (d, 8.7 Hz, 1 H), 5.15–5.05 (m, 1 H), 4.75–4.65 (m, 1/3H), 4.57 (dd, 7 Hz, 9 Hz, 1/3H), 4.44 (dd, 6.5 Hz, 9.0 Hz, 1/3H), 4.21–4.07 (m, 1 H), 3.56–3.44 (m, 1 H), 3.28–3.12 (m, 3 H), 3.08–3.01 (m, 2/3H), 2.89, 2.86 (2s, 3 H), 12.82–2.55 (m, 1 H), 2.03 (dd, 6.0 Hz, 13.8 Hz, 1/2H), 1.86 (dd, 6.0, 13.7, 1/2H), 1.70–1.35 (m, 3 H), 1.33, 1.32, 1.31, 1.28, 1.24 (5s, 6 H), 1.33–1.29 (m, hidden), 1.06 (hr. d, 13 Hz, 1/3H), 0.71 (dt, 4.6 Hz, 13 Hz, 1/3H), 0.49 (dt, 4.6 Hz, 13 Hz, 1/3H), −0.21 (dt, 4.6 Hz, 13 Hz, 1/3H), −0.49 (dt, 4.6 Hz, 13 Hz, 1/3H). FAB-MS: calc. for $C_{29}H_{37}N_5O_6S$, 583; found 584 (M+H, 20%).

EXAMPLE 15

N-[1(R)-[(2-acetyl-1,2,3,4-tetrahydrospiro[isoquinolin-4,4'-piperidin]-1'-yl)carbonyl]-2-(indol-3-yl)ethyl]-2-amino-2-methylpropanamide, hydrochloride Step A: 1,3-dihydro-1,3-dihydroxyspiro[4H-2-benzofuran-4,4'-piperidine]-1'-carboxylic acid, 1,1-dimethylethyl ester To a stirred solution of spiro[1H-indene-1,4'-piperidine]-1'-carboxylic acid, 1,1-dimethylethyl ester (800 mg, 2.8 mmol) in methanol (50 mL) at −78° C., was bubbled ozone until the solution turned blue. The mixture was let stand at that temperature for 20 minutes, then purged with nitrogen. Dimethyl sulfide (3 mL) was added and the mixture was warmed to room temperature and stirred for two hours. Evaporation of the solvent gave a crude product (940 mg) which was used without purification.

Step B: 1,2,3,4-tetrahydrospiro[isoquinolin-4,4'-piperidine]-1'-carboxylic acid, 1,1-dimethylethyl ester The intermediate of Step A (100 mg) was stirred in methanol (2 mL) saturated with ammonia for one day, and evaporated to remove ammonia. The residue was redissolved in methanol (3 mL) and sodium cyanoborohydride (50 mg, excess) was added. The mixture was stirred overnight. Evaporation and purification gave the amine.
$^1$H NMR (400 MHz, CD$_3$OD): δ7.35–6.96 (m, 4 H), 4.00 (s, 2 H), 3.14 (s, 2 H), 3.90 (br. s, 2 H), 2.05 (br. s, 2 H), 1.95 (br. t, 2 H), 0.69 (d, 2 H), 1.49 (s, 9 H).

Step C: 2-Acetyl-1,2,3,4-tetrahydrospiro[isoquinolin-4,4'-piperidine]-1'-carboxylic acid, 1,1-dimethylethyl ester The intermediate (16 mg) from Step A was treated with pyridine (2 mL) and acetic anhydride (2 mL) for 2 hours and the reaction mixture was evaporated in vacuo to afford the desired compound (12 mg).
$^1$H NMR (400 MHz, CDCl$_3$, compound exists as a mixture of 3:1 rotamers): δ7.36–7.05 (m, 4 H), 4.72 (s, 2/4H), 4.65 (s, 6/4H), 4.10–4.00 (br. d, 12.8 Hz, 2 H), 3.85 (br. s, 3/4H), 3.65 (s, 1/4H), 3.11 (t, 13.1 Hz, 3/4H), 3.00 (t, 13.1 Hz, 1/4H), 2.19 (s, 3/4H), 2.18 (s, 9/4H) 2.00–1.80 (m, 2 H), 1/65–1.47 (m, 2H, hidden), 1.47 (s, 9/4H), 1.45 (s, 27/4H).

Step D: 2-Acetyl- 1,2,3,4-tetrahydrospiro[isoquinolin-4,4'-piperidine]

To a solution of intermediate from Step C (12 mg) in ethyl acetate (5 mL) at 0° C., was bubbled HCl (gas) until it is saturated. After 30 minutes, the reaction mixture was evaporated in vacuo to afford the desired intermediate.
$^1$H NMR (400 MHz, CD$_3$OD): δ7.47–7.19 (m, 4 H), 4.79 (s, 2 H), 3.96 (s, 2 H), 3.36 (br. d, 6.7 Hz, 2 H), 2.30–2.24 (m, 1 H), 2.21 (s, 3 H), 1.76 (d, 13 Hz). FAB-MS: calc. for $C_{15}H_{20}N_2O$, 244; found 245 (M+1, 100%)

Step E: N-[1(R)-[(2-Acetyl-1,2,3,4-tetrahydrospiro[isoquinolin-4,4'-piperidin]-1'-yl)carbonyl]-2-(indol-3-yl) ethyl]-2 -[[(1,1-dimethylethyloxy)carbonyl]amino]-2-methylpropanamide Title compound was prepared from the intermediate from Step D according to the procedures described previously.

EXAMPLE 16

N-[1(R)-[1,2-dihydro-1-methylsulfonylspiro[3H-indole-3,4'-piperidin]- 1'- yl)carbonyl] -2-(2', 6'-difluorophenyl)-methyloxy)ethyl]-2-amino-2-methylpropanamide hydrochloride Step A: methyl α(R)-[[2-[[(1,1-dimethylethoxy)carbonyl] amino] -2,2-dimethyl-1-oxoethyl]amino]-3[(2', 6'-difluorophenyl) -methoxy]propanic acid Oil free sodium hydride (prepared from 60% oil dispersion of sodium hydride by washing with hexanes (3X), 1.2 g, 30.0 mmole), suspension in 30 mL N,N-dimethylformamide was added N-t-butyloxycarbonyl-(D)-serine (3.07 g, 15.0 mmole) in 10 mL N,N-dimethylformamide at room temperature. When no more gas evolves 2,6-diflorobenzyl bromide (2.68 g, 12.9 mmole) was added. After 18 hours stirring at room temperature, iodomethane (1.0 mL, 16.0 mmole) was added to the reaction mixture. The mixture was stirred another 1 hour, and then poured into water, and extracted with ethyl ether. The organic layer was washed sequentially with water (5X), brine and dried over sodium sulfate, filtered and concentrated. The residue was dissolved in 20 ml of chloroform and BOC-α-methylalanine, EDC, HOBT, and Et$_3$N were added at room temperature. After 3 hours the reaction mixture was poured into water and extracted with methylene chloride. The organic layer was dried over sodium sulfate and concentrated. The title compound was obtained after purification by chromatography, (hexane/ethyl acetate:3/1) to give 2.37 g (35%).
$^1$H NMR (300 MHz, CDCl$_3$ mixture of rotamers): 7.27 (m, 1 H), 7.02–6.88 (m, 2 H), 4.95 (m, 1 H), 4.72 (dt, 8, 3 Hz, 1 H), 4.58 (br. s, 2 H), 3.90 (m, 1 H), 3.78 (s, 1 H), 3.69 (s, 3 H), 1.48 (s, 3 H), 1.45 (s, 3 H), 1.41 (s, 9 H).

Step B: N-[1(R)-[1,2-dihydro-1-methylsulfonylspiro[3 H-indole -3,4'-piperidin]-1'-yl)carbonyl]-2-(2', 6'-difluorophenyl -methyloxy)ethyl]-2-amino-2-methylpropanamide hydrochloride A solution of the intermediate obtained from this Example, Step A (2.37 g, 5.29 mmole) in 30 mL of methanol was added lithium hydroxide (340 mg, 8.1 mmole) in 3 mL of water. After 2 hours stirring at room temperature, the reaction mixture was concentrated, and then diluted with water, extracted with ethyl ether. The organic layer was discarded. The aqueous layer was acidified with 1N hydrochloric acid to pH=1.5 and extracted with ethyl ether (3X).

The organic layer was dried over sodium sulfate, filtered, and concentrated to give 2.18 g (95%) of acid. The title compound was prepared from acid (78 mg, 0.18 mmole), and 1,2-dihydro-1-methylsulfonylspiro[3 H-indole-3,4'-piperidine hydrochloride (50 mg, 0.165 mmole) by the procedure described in Example 20, Step B (use hydrochloride in ethyl ether instead of trifluoroacetic acid) to give 48 mg (44%).

$^1$H NMR (400 MHz, CD$_3$OD mixture of rotamers): 7.39 (m, 2 H), 7.22 (m, 1 1/2H), 7.03 (m, 3 1/2H), 5.14 (dd, 13, 7 Hz, 1 H), 4.66 (d, 16 Hz, 2 H), 4.49 (m, 1 H), 4.09 (m, 1 H), 3.92 (br. s, 2 H), 3.76 (m, 2 H), 3.25 (m, 1 H), 2.97 (s, 3/2H), 2.96 (s, 3/2H), 2.87 (m, 1 H), 1.95 (m, 1 H), 1.76 (m, 3 H), 1.61 (s, 3/2H), 1.57 (s, 3 3/2H), FAB-MS: 565 (M+1).

EXAMPLE 17

N-[1(R)-[(1,2-dihydro-1-methylsulfonylspiro
[3H-indole-3,4'-piperidin]-
1'-yl)carbonyl]-3-cyclohexylpropyl]-2-amino-2-
methylpropanamide hydrochloride Step A: t-butyloxycarbonyl-(D)-hexahydrohomophenylalanine A solution of t-butyloxycarbonyl-(D)-homophenylalanine (100 mg, 0.358 mmole) in 1 mL acetic acid was hydrogenated over PtO$_2$ at one atmosphere for 16 hours. The mixture was filtered through Celite and the filtrate concentrated and azeotroped with toluene.

$^1$H NMR (400 MHz, CDCl$_3$): 5.03 (d, 8 Hz, 1 H), 4.22 (m, 1 H), 1.82 (m, 1 H), 1.64 (m, 6 H), 1.41 (s, 9 H), 1.20 (m, 6 H), 0.84 (m, 2 H).

Step B: benzyl α(R)-[[2-[[(1,1-dimethylethoxy)carbonyl] amino] -2,2-dimethyl-1-oxoethyl]amino]-4-cyclohexylbutanoic acid A solution of BOC-D-homaphenylalanine in acetic acid was hygrogenated over PtO$_2$ at one atmosphere for 16 hours. The mixture was filtered through celite and concentrated. To this residue (44 mg) in 15 mol DMF was added benzyl bromide (198 ml) and K$_2$CO$_3$ (970 mg) at room temperature. After stirring overnight, the mixture was poured into 200 ml of ether and washed with water. The organic phase was dried over MgSO$_4$, filtered and concentrated. The residue was purified by flash chromatography (silica gel, 7.5% ethyl acetate in hexanes) to provide 534 mg (95%) of this intermediate. A solution of 534 mg of this material in 10 ml 1:1 TFA/CH$_2$Cl$_2$ was stirred for 1 hour then stripped and azeotroped from toluene. The residue was dissolved in 10 ml CH$_2$Cl$_2$ and cooled to 0° C. BOC-α-methylalanine (362 mg), EDC, HOBT and NMM were added and stirred overnight. The solution was poured into 250 ml ethyl acetate and washed sequentially with 1N NaHSO$_4$ (aq.), water and saturated aqueous NaHCO$_3$. The organic phase was dried, filtered and concentrated. Purified by flash chromatography (silica gel, ethyl acetate/hexanes) to provide 638 mg of the title compound.

$^1$H NMR (200 MHz, CDCl$_3$): 0.8–0.95 (m, 3 H), 1.05–1.3 (m, 7 H), 1.4–1.9 (m, 19 H), 2.15 (m, 2 H), 4.59 (m, 1 H), 4.87 (m, 1 H), 5.18 (m, 2 H), 6.96 (m, 1 H), 7.35 (m, 5 H). FAB-MS calculated for C$_{26}$H$_{40}$N$_2$O$_5$ 460; found 461.5 (M+H).

Step C: N-[1(R)-[(1,2-dihydro-1-methylsulfonylspiro[3 H-indole-3,4'-piperidin]-1'-yl)carbonyl]-3-cyclohexylpropyl]-2 -amino-2-methylpropanamide hydrochloride A mixture of 638 mg of the intermediate obtained in Step B and 100 mg of 10% Pd on carbon was stirred under a balloon containing H$_2$ for 4 hours. The mixture was filtered through Celite and the filtrate was concentrated. A portion (87 mg) of this residue was dissolved in 2 ml CH$_2$Cl$_2$ and 49.8 mg of 1,2-dihydro-1-methylsulfonylspiro[3H-indole-3, 4'-piperidine hydrochloride, EDC and HOBT were added and stirred for 16 hours. The solution was poured into 200 ml ethyl acetate and washed sequentially with 1N NaHSO$_4$ (aq.), water and saturated aqueous NaHCO$_3$. The organic phase was dried, filtered and concentrated. Purified by flash chromatography (silica gel, 60% ethyl acetate/hexanes) to provide 55 mg (47%) of this intermediate. All of this material was dissolved in 2 ml 1:1 TFA/CH$_2$Cl$_2$ and stirred for 1/2hour. The solution was stripped and the residue was purified by flash chromatography (silica gel, methanol, NH$_4$OH(aq.), CH$_2$Cl$_2$). The compound was then dissolved in CH$_2$Cl$_2$, treated with HCl in ether and concentrated to provide the title compound.

$^1$H NMR (400 MHz, CD$_3$OD): 0.93 (m, 2 H), 1.15–1.3 (m, 6 H), 1.55–1.8 (m, 1 H), 2.06 (dr, 15, 4 Hz, 1 H), 2.88 (m, 1 H), 2.97 (m, 1 H), 3.35 (m, 2 H), 3.8–4.1 (m, 3 H), 4.51 (m, 1H), 4.83 (m, 1H), 7.06 (q, 7 Hz, 1H), 7.22 (m, 2H), 7.37 (d, 8 Hz, 1H).

FAB-MS calculated for C$_{27}$H$_{42}$N$_4$O$_4$S 518; found 519.7 (M+H)

EXAMPLE 18 (METHOD 1)

N-[1(R)-[(1,2-Dihydro-1-methanesulfonylspiro
[3H-indole-3
4'-piperidin]-1'-yl)carbonyl]-2-(phenylmethyloxy)
ethyl]-2-amino-2-methylpropanamide hydrochloride.

Step A: 1,2-Dihydro-1-methanesulfonylspiro[3H-indole-3, 4'-piperdine]hydrochloride To a solution of 1.20 g (5.8mmol) of 1'-methyl-1,2 -dihydro-spiro[3H-indole-3,4'-piperidine] (prepared as described in H. Ong et al J. Med. Chem. 1983, 23, 981–986) in 20 mL of dry dichloromethane at 0° C. was added triethylamine (0.90 mL; 6.4 mmol) and methanesulfonyl chloride (0.49 mL; 6.35 mmol) and stirred for 30 min. The reaction mixture was poured into 15 mL of saturated aqueous sodium bicarbonate solution and extracted with dichloromethane (2×10 mL). The combined organics were washed with brine (20 mL), dried over anhydrous potassium carbonate, filtered and the solvent removed under reduced pressure to yield 1.44 g of the methanesulfonamide derivative as pale yellow oil which was used without purification.

To a solution of above crude product in 20 mL of dry 1,2-dichloroethane at 0° C. was added 1.0 mL (9.30 mmol) of 1-chloroethyl chloroformate, and then stirred at RT for 30 min and finally at reflux for 1 h. The reaction mixture was concentrated to approximately one third of the volume and then diluted with 20 mL of dry methanol and refluxed for 1.5 h. The reaction was cooled to RT and concentrated to approximately one half of the volume. The precipitate was filtered and washed with a small volume of cold methanol. This yielded 1.0 g of the piperidine HCl salt as a white solid. The filtrate was concentrated and a small volume of methanol was added followed by ether. The precipitated material was once again filtered, washed with cold methanol, and dried. This gave an additional 0.49 g of the desired product. Total yield 1.49 g (70%).

$^1$H NMR(CDCl$_3$, 200 MHz) δ7.43–7.20 (m, 3H), 7.10 (dd, 1H), 3.98 (bs, 2H), 3.55–3.40 (bd, 2H), 3.35–3.10 (m, 2H), 2.99 (s, 3H), 2.15 (t, 2H), 2.00 (t, 2H).

Step B: N-[1(R)-[(1,2-Dihydro-1-methanesulfonylspiro[3H-indole- 3,4'-piperdin]-1'-yl)carbonyl]-2-(phenylmethyloxy)ethyl]- 2-[(1,1-dimethylethoxy)carbonyl]amino-2-methylpropanamide To 0.35 g (1.15 mmol) of (2R)-2-[(1,1-dimethylethoxy) carbonyl]amino-3-[2-(phenylmethyloxy)ethyl]-1-propanoic acid in 13 mL of dichloromethane was added 1,2-dihydro-1-methanesulfonylspiro- 3H-indole-3,4'-piperdine]hydrochloride (0.325 g; 1.07 mmol), 0.18 mL (1.63 mmol) of N-methylmorpholine, 0.159 g (1.18 mmol) of 1-hydroxybenztriazole(HOBT) and stirred for 15 min. EDC (0.31 g; 1.62 mol) was added and stirring was continued for 1 h. An additional 60 μL of N-methylmorpholine was added and stirred for 45 min. The reaction mixture was poured into 5 mL of water and the organic layer was separated. The organic layer was washed with 5 mL of 0.5N aqueous hydrochloric acid and 5 mL of saturated aqueous sodium bicarbonate solution. The combined organics were dried over anhydrous magnesium sulfate, and concentrated to yield 0.627 g of the product as a yellow foam which was used without purification.

To a 0.627 g (1.07 mmol) of the above product in 5 mL of dichloromethane was added 1.0 mL of trifluoroacetic acid and stirred at RT for 75 min. An additional 1.00 mL of trifluoroacetic acid was added and stirred for 10 min. The reaction mixture was concentrated, diluted with 5.0 mL of dichloromethane and carefully basified by pouring into 10 mL of 10% aqueous sodium carbonate solution. The organic layer was separated and the aqueous layer was further extracted with 2×15 mL of dichloromethane. The combined organics were washed with 5 mL of water, dried over potassium carbonate, filtered and concentrated to give the 0.486 g of the amine as a light yellow foam which was used without purification.

To 0.486 g (1.01 mmol) of the amine and 10 mL of dichloromethane was added 0.26 g (1.28 mmol) of 2-[(1,1-dimethylethoxy)carbonyl]amino-2-methyl-propanoic acid, 0.173 g (1.28 mmol) of 1-hydroxybenztriazole (HOBT) and EDC (0.245 g; 1.28 mol) and stirried at RT overnight. The reaction mixture was poured into 5.0 mL of water and the organic layer was separated. The aqueous layer was back extracted with 5 mL of dichloromethane. The combined organics were washed with 5.0 mL of 0.5N aqueous hydrochloric acid, 5 mL of saturated aqueous sodium bicarbonate solution dried over anhydrous magnesium sulfate, and concentrated to yield 0.751 g of the crude product as a yellow foam. A solution of this crude product in dichloromethane was chromatographed on 25 g of silica gel and eluted first with hexanes/acetone/dichloromethane (70/25/5) and then with hexanes/acetone/dichloromethane (65/30/5). This gave 0.63 g of the title compound as a white solid.

$^1$H NMR(CDCl$_3$, 400 MHz) Compound exists as a 3:2 mixture of rotamers δ7.40–7.10 (m, 6H), 7.06 (d, 1/3H), 7.02 (t, 1/3H), 6.90 (t, 1/3H), 6.55 (d, 1/3H), 5.15 (m, 1H), 4.95 (bs, 1H), 4.63 (bd, 1/3H), 4.57–4.40 (m, 22/3H), 4.10 (bd, 1/3H), 4.00 (bd, 1/3H), 3.82 (t, 1H), 3.78–3.62 (m, 2H), 3.60–3.50 (m, 1H), 3.04 (q, 1H), 2.87 (s, 1H), 2.86 (s, 2H), 2.80–2.60 (m, 1H), 1.90 (bs, 1H), 2.85–2.75 (m, 1H), 1.82–1.60 (m, 3H), 1.55–1.45 (m, 1H), 1.45 (s, 4H), 1.42 (s, 2H), 1.39 (s, 9H).

Step C: N-[1(R)-[(1,2-Dihydro-1-methanesulfonylspiro[3H-indole- 3,4'-piperdin]-1'-yl)carbonyl]-2-(phenylmethyloxy)ethyl]- 2-amino-2-methylpropanamide hydrochloride To 0.637 g (0.101 mmol) of the intermediate from Step B in 5 mL of dichloromethane was added 2.5 mL of trifluoroacetic acid and stirred at RT for 30 min. The reaction mixture was concentrated to an oil, taken up in 10 mL of ethyl acetate and washed with 8 mL of 10% aqueous sodium carbonate solution. The aqueous layer was further extracted with 5 mL of ethyl acetate. The combined organics were washed with 10 mL of water, dried over magnesium sulfate, filtered and concentrated to give the 0.512 g of the free base as a white foam.

To 0.512 g of the free base in 5 mL of ethyl acetate at 0° C. was added 0.2 mL of saturated hydrochloric acid in ethyl acetate and stirred for 1.5 h. The white precipitate was filtered under nitrogen, washed with ether, and dried to give 0.50 g of the title compound as a white solid.

$^1$H NMR (400 MHz, CD$_3$OD) Compound exists as 3:2 mixture of rotamers. δ7.40–7.28 (m, 4H), 7.25–7.17 (m, 2H), 7.08 (t, 1/3H), 7.00 (t, 1/3H), 6.80 (d, 1/3H), 5.16 (ddd, 1H), 4.60–4.42 (m, 3H), 4.05 (t, 1H), 3.90 (bs, 2H), 3.83–3.70 (m, 2H), 3.30–3.15 (m, 1H0, 2.97 (s, 1H), 2.95 (s, 2H), 2.90–2.78 (m, 1H), 1.96 (t, 1/3H), 1.85–1.65 (m, 4H), 1.63 (s, 2H), 1.60 (s, 4H).

EXAMPLE 19 (METHOD 2)

N-[1(R)-[(1,2-Dihydro-1-methanesulfonylspiro [3H-indole-3,4'-piperdin]- 1'-yl) carbonyl]-2-(phenylmethyloxy)ethyl]-2-amino-2-methylpropanamide hydrochloride Step A: (2R)-[[[-2-(1,1-dimethylethoxy)carbonyl]amino]-2,2-dimethyl-1-oxoethyl]amino-2-(phenylmethoxy) ethyl]- 1-propanoic acid allyl ester Prepared from (2R)-2-[(1,1-dimethylethoxy)carbonyl]-amino- 3-(phenylmethyloxy)ethyl-propanoic acid and allyl alcohol by carrying out the coupling reaction in CH$_2$Cl$_2$ in the presence of EDC and DMAP.

$^1$H NMR (400 MHz, CDCl$_3$) δ7.25 (s, 5H), 5.8 (m, 1H), 5.2 (dd, 2H), 5.0 (bs, 1H), 4.7 (m, 1H), 4.6 (m, 2H), 4.4 (dd, 2H), 3.9 (dd, 1H), 3.6 (dd, 1H), 1.45 (d, 6H), 1.39 (s, 9H).

Step B: (2R)-[[[-2-(1,1-dimethylethoxy)carbonyl]amino]-2,2-dimethyl-1-oxoethyl]amino-2-(phenylmethyloxy) ethyl)- 1-propanoic acid To a stirred solution of the crude intermediate obtained in Step A (6.7 g, 15.9 mmol), tetrakis (triphenylphosphine)-palladium (1.8 g, 0.1 eq) and, triphenyl phosphine (1.25 g, 0.3 eq) was added a solution of potassium-2-ethyl hexanoate (35 mL, 0.5M solution in EtOAc). The reaction mixture was stirred at room temperature under nitrogen atmosphere for 1 h and then diluted with ether (100 mL) and poured into ice-water. The organic layer was seperated and the aqueous fraction was acidified with citric acid (20%), then extracted with EtOAc. The EtOAc extracts were washed with brine, dried over magnesium sulfate, filtered and evaporated to give the title compound as a solid.

$^1$H NMR (400 Hz, CD$_3$OD) δ7.3 (s, 5H), 4.7 (m, 1H), 4.5 (s, 2H), 4.0 (m, 1H), 3.6 (m, 1H), 1.4 (d, 6H), 1.3 (s, 9H).

Step C: N-[1(R)-[(1,2-Dihydro-1-methanesulfonylspiro[3H-indole- 3,4'-piperdin]-1'-yl)carbonyl]-2-(phenylmethyloxy)ethyl]- 2-[(1,1-dimethyl-ethoxy)carbonyl]amino-2-methylpropanamide To a solution of 1.0 g (3.44 mmol) of 1-methanesulfonylspiro[indoline-3,4'-piperidine]hydrochloride, 1.44 g (3.78 mmol) of (2R)-[[-2-(1,1 -dimethylethoxy)carbonyl)amino]-2,2-dimethyl-1-oxoethyl]-amino- 2-(phenylmethyloxy)ethyl)-1-propanoic acid, N-methyl morpholine (0.58 mL; 5.20 mmol), and 1-hydroxybenztriazole (HOBT) (0.58 g; 3.78 mmol), in 50 mL of dichloromethane was added EDC (1.03 g; 5.20 mmol) and stirred at RT for 16 h. The reaction mixture was diluted with an additional 50 mL of dichloromethane and washed with aqueous sodium bicarbonate solution (50 mL), dried over anhydrous magnesium sulfate, filtered, and concentrated. Flash chromatography (50 g silica gel) of the crude oily residue gave 2.148 g (90%) of the desired material as a colorless foam.

$^1$H NMR (CDCl$_3$, 400 MHz) Compound exists as a 3:2 mixture of rotamers δ7.40–7.10 (m, 6H), 7.06 (d, 1/3H), 7.02 (t, 1/3H), 6.90 (t, 1/3H), 6.55 (d, 1/3H), 5.15 (m, 1H), 4.95 (bs, 1H), 4.63 (bd, 1/3H), 4.57–4.40 (m, 22/3H), 4.10 (bd, 1/3H), 4.00 (bd, 1/3H), 3.82 (t, 1H), 3.78–3.62 (m, 2H), 3.60–3.50 (m, 1H), 3.04 (q, 1H), 2.87 (s, 1H), 2.86 (s, 2H), 2.80–2.60 (m, 1H), 1.90 (bs, 1H), 2.85–2.75 (m, 1H), 1.82–1.60 (m, 3H), 1.55–1.45 (m, 1H), 1.45 (s, 4H), 1.42 (s, 2H), 1.39 (s, 9H).

Step D: N-[1(R)-[(1,2-Dihydro-1-methanesulfonylspiro [3H-indole- 3,4'-piperdin]-1'-yl)carbonyl]-2-(phenylmethyloxy)ethyl]- 2-amino-2-methylpropanamide hydrochloride To a solution of 2.148 g (3.41 mmol) of the intermediate from Step C in 10 mL of dichloromethane was added 5 mL of trifluoroacetic acid and stirred for 1 h. The reaction mixture was concentrated and basified with 100 mL of 5% aqueous sodium carbonate solution and extracted with dichloromethane (3×50 mL). The combined organics were washed with brine (50 mL), dried over anhydrous potassium carbonate, filtered, and concentrated to yield a colorless foam. To a solution of the foam in 25 mL of ethyl acetate at 0° C. was added 4 mL of 1M solution of hydrochloric acid in ethyl acetate. The precipitate was filtered and washed first with ethyl acetate and then with ethyl acetate-ether (1:1), dried to yield 1.79 g (93%) of the title compound as a colorless solid.

$^1$H NMR(400 MHz, CD$_3$OD) Compound exists as 3:2 mixture of rotamers. δ7.40–7.28 (m, 4H), 7.25–7.17 (m, 2H), 7.08 (t, 1/3H), 7.00 (t, 1/3H), 6.80 (d, 1/3H), 5.16 (ddd, 1H), 4.60–4.42 (m, 3H), 4.05 (t, 1H), 3.90 (bs, 2H), 3.83–3.70 (m, 2H), 3.30–3.15 (m, 1H$_{0, 2.97}$ (s, 1H), 2.95 (s, 2H), 2.90–2.78 (m, 1H), 1.96 (t, 1/3H), 1.85–1.65 (m, 4H), 1.63 (s, 2H), 1.60 (s, 4H).

EXAMPLE 20

N-[1(R)-[(1,2-Dihydro-1-methanesulfonyl-5-bromo-spiro [3H-indole-3,4'-piperdin]-1'-yl)carbonyl]-2-(phenylmethyloxy)ethyl]-2-amino-2-methylpropanamide trifluoroacetate Step A: N-[1(R)-[(1,2-Dihydro-1-methanesulfonyl-5-bromo-spiro[3 H-indole-3,4'-piperdin]-1'-yl)carbonyl]-2-(phenylmethyl-oxy)-ethyl]-2-[(1,1-dimethylethoxy) carbonyl]amino-2-methylpropanamide To a solution 300 mg(1.03 mmol) of 1-methanesulfonyl-spiro-[3H-indole-3,4'-piperidine]hydrochloride in 5 mL of glacial acetic acid was added 0.28 g (2.06 mmol) of bromine and stirred at RT for 1 h. The reaction mixture was concentrated to dryness, basified with 10 mL of 5% aqueous sodium carbonate solution, and extracted with dichloromethane (3×10 mL). The combined organics were washed with brine (10 mL), dried over anhydrous potassium carbonate, filtered, and concentrated to yield 0.25 g of a crude product as a yellow oil which was used without purification.

Step B:

To a solution of the above crude product in 10 mL of dichloromethane was added 0.43 g (1.13 mmol) of the intermediate from Example 19 Step B, 0.17 g (1.13 mmol) of HOBT, and 0.34 g (1.70 mmol) of EDC and stirred at RT for 16 h. The reaction mixture was diluted with 15 mL of ether and washed with 10% aqueous citric acid (15 mL), saturated sodium bicarbonate solution (15 mL), dried over anhydrous magnesium sulfate, filtered and concentrated to give a crude oily product. This residue was purified was flash chromatography (15 g SiO$_2$; CH$_2$Cl$_2$-Acetone(10:1) as eluent) to yield 0.184 g (26% for 2 steps) of the coupled material as colorless foam.

To 0.184 g (0.26 mmol) of the above material in 2 mL of dichloromethane was added 2 mL of trifluoroacetic acid and stirred at RT for 1 h. The reaction mixture was evaporated to dryness to yield 0.146 g (93%) of the title compound as a white solid. FAB-MS: calculated for C$_{27}$H$_{34}$BrN$_4$O$_5$S 608; found 609.5

EXAMPLE 21

N-[1(R)-[(1,2-Dihydro-spiro[3H-indole-3,4'-piperdin]-1'-yl)carbonyl]-2-(indol-3-yl)ethyl]-2-amino-2-methylpropanamide dihydrochloride Step A: Spiro[3H-indole-3,4'-piperidine]

To a solution of 1.0 g (5.0 mmol) of 1'-methyl-spiro[3 H-indole-3,4'-piperidine](prepared as described in H. Ong et al *J. Med. Chem.* 1983, 23, 981–986) and 1.0 g of powdered potassium carbonate in 30 mL of dry dichloromethane at RT was added to 0.50 g of cyanogen bromide and stirred for 1 h. The reaction mixture was filtered through a pad of celite and washed with chloroform-methanol (95:5). The filtrate was concentrated and the residue was flushed through a pad of silica gel with chloroform-methanol (95:5) as eluent. This gave ~1.2 g of a yellow oil which was used without purification.

To a suspension of above compound in 30 mL of dry DME at 0° C. was added 0.30 g of lithium aluminum hydride and warmed to RT and finally refluxed for 1 h. The reaction mixture was cooled to 0° C. and quenched with 0.30 mL of water, 0.30 mL of 15% aqueous of sodium hydroxide solution, and 0.90 mL of water. The solids were filtered off through a pad of celite and washed well with chloroform-methanol (10:1). Concentration of the filtrate gave 0.74 g of the compound as a yellow foam. This material was a 1:1 mixture of the title compound and 1'-methyl-spiro[3H-indole-3,4'-piperidine].

Step B: (2R)-[[-2-[[1,1-dimethylethoxy)carbonyl]amino]-2,2-dimethyl-1-oxoethyl]amino]-1H-indole-3-propanoic acid benzyl ester To 5.0 g (16.5 mmol) of the commercially available N-t-BOC-D-tryptophan in 100 mL of chloroform was added 1.80 mL (16.5 mmol) of benzyl alcohol, 0.20 g (1.65 mmol) of 4-N,N-dimethylamino pyridine (DMAP), and 3.20 g of EDC and stirred for 16 h. The reaction mixture was poured into 100 mL of water and the organic layer was seperated. The aqueous was further extracted with 2×100 mL of chloroform. The combined organics were washed with 50 mL of 10% aqueous citric acid, 100 mL of 10% aqueous sodium bicarbonate solution, dried over anhydrous magnesium sulfate, filtered and concentrated to give a thick oil.

To a solution of this oil in 10 mL of dichloromethane was added 20 mL of trifluoroacetic acid and stirred for 1 h. The reaction mixture was concentrated, basified carefully with saturated aqueous sodium bicarbonate solution, and extracted with chloroform (2×100 mL). The combined organics were washed with brine (100 mL), dried over potassium carbonate, filtered, and concentrated to give 5.46 g of the amine as a brown oil which was used without purification.

To 5.46 g of the above product in 100 mL of chloroform was added 3.40 g (22.2 mmol) of HOBT, 4.60 g (22.2 mmol) of N-BOC-α-methyl alanine, and 5.32 g (28.0 mmol) of EDC and stirred for 16 h. The reaction mixture was poured into 100 mL of water and the organic layer was seperated. The aqueous was further extracted with 2×100 mL of chloroform. The combined organics were washed with 50 mL of 10% aqueous citric acid, 100 mL of 10% aqueous sodium bicarbonate solution, dried over anhydrous magnesium sulfate, filtered and concentrated to give 6.94 g of the product as a thick oil. Flash chromatography (200 g SiO$_2$; hexane-ethyl acetate as eluent) gave 4.75 g of the desired material as a colorless foam.

$^1$H NMR (CDCl$_3$, 200 MHz) δ8.48 (bs, 1H), 7.54 (bd, 1H), 7.38–7.23 (m, 3H), 7.19 (bd, 2H), 7.15–7.00 (m, 1H), 6.90 (d, 1H), 6.86 (d, 1H), 5.06 (bs, 2H), 4.95 (ddd, 1H), 3.30 (2dd, 2H), 1.40 (s, 15H)

Step C: (2R)-[[-2-[[1,1-dimethylethoxy)carbonyl]amino]-2, 2-dimethyl- 1-oxoethyl]amino]-1H-indole-3-propanoic acid To a solution of 4.75 g of the material from Step B in 100 mL of ethanol was added 1.0 g of 10% Pd/C and stirred at RT under a H$_2$ balloon for 18 h. The catalyst was filtered off through a pad of celite and washed with ethyl acetate. The filtrate was concentrated to give 2.96 g of the acid as a colorless foam.

$^1$H NMR (CDCl$_3$, 200 MHz) δ8.60 (bs, 1H), 7.55 (d, 1H), 7.26–6.90 (m, 3H), 6.88 (bd, 1H), 4.80 (m, 1H), 3.32 (2rid, 2H), 1.37 (s, 3H), 1.35 (s, 12H)

Step D: N-[1(R)-[(1,2-Dihydro-spiro[3H-indole-3,4'-piperdin]-1 '-yl)carbonyl]-2-(indol-3-yl)ethyl]-2-[(1,1-dimethylethoxy)carbonyl]amino-2-methylpropanamide To a solution of 0.122 g (0.542 mmol) of a 1:1 mixture of the intermediate from step A and 1'-methyl-spiro[3H-indole-3,4'-piperdine]in 5 mL of dry chloroform at RT was added 0.105 g (0.271 mmol) of the intermediate from Step C, 41 mg (0.271 mmol) of HOBT, and 80 mg (0.41 mmol) of EDC and stirred at RT for 2 h. The reaction mixture was diluted with 10 mL of chloroform was washed with saturated aqueous sodium bicarbonate solution (10 mL) and 10 mL of brine, dried over anhydrous potassium carbonate, filtered and concentrated. Flash chromatography (10 g SiO$_2$; 2% MeOH—CHCl$_3$) of the residue gave 94 mg of the desired product as a yellow foam.

The compound exists as 3:2 mixture of rotamers. $^1$H NMR (CDCl$_3$, 400 MHz) δ8.37 (d, 1/3H), 8.35 (d, 2/3H), 8.19 (d, 1H), 7.72 (d, 2/3H), 7.60 (d, 1/3H), 7.38 (d, 2/3H), 7.32 (d, 1/3H), 7.22–7.08 (m, 3H), 7.00 (2t, 1H), 6.93 (d, 1/3H), 6.69 (t, 1H), 6.60 (d, 1/3H), 6.56 (d, 2/3H), 6.50 (d, 2/3H), 5.30–5.15 (m, 1H), 5.00 (bs, 1H), 4.34 (m, 1H), 3.62–3.50 (m, 1H), 3.30–3.11 (m, 4H), 2.90 (dt, 1H), 2.40 (dt, 1/3H), 1.70–1.55 (m, 12/3H), 1.34 (s, 2H), 1.31 (s, 4H), 1.28 (s, 1H), 1.31 (s, 9H), 1.20–1.11 (m, 1H), 0.32 (dt, 1/3H)

Step E: N-[1(R)-[(1,2-Dihydro-spiro[3H-indole-3,4'-piperdin]- 1'-yl)carbonyl]-2-(indol-3-yl)ethyl]-2-amino-2-methylpropanamide dihydrochloride To 27.5 mg of the intermediate from Step D was added 1.0 mL of methanol and 1.0 mL of concentrated hydrochloric acid and stirred at RT for 1 h. The reaction mixture was concentrated, basified with 5 mL of 10% aqueous sodium carbonate solution, and extracted with chloroform (3×5 mL). The combined organics were washed with brine (10 mL), dried over potassium carbonate, filtered, and concentrated to yield a thick oil. Preparative TLC (0.50 mm plate; chloroform-methanol 96:5+1% NH$_4$OH) gave 12 mg of the desired product as a yellow solid.

The compound exists as 3:2 mixture of rotamers. $^1$H NMR (CDCl$_3$, 400 MHz) δ8.37 (d, 1/3H), 8.35 (d, 2/3H), 8.19 (d, 1H), 7.72 (d, 2/3H), 7.60 (d, 1/3H), 7.38 (d, 2/3H), 7.32 (d, 1/3H), 7.22–7.08 (m, 3H), 7.00 (2t, 1H), 6.93 (d, 1/3H), 6.69 (t, 1H), 6.60 (d, 1/3H), 6.56 (d, 2/3H), 6.50 (d, 2/3H), 5.30–5.15 (m, 1H), 4.34 (m, 1H), 3.62–3.50 (m, 1H), 3.30–3.11 (m, 4H), 2.90 (dt, 1H), 2.40 (dt, 1/3H), 1.70–1.55 (m, 12/3H), 1.34 (s, 2H), 1.31 (s, 4H), 1.28 (s, 1H), 1.20–1.11 (m, 1H), 0.32 (dt, 1/3H).

EXAMPLE 22

N-[1(R)-[(1,2-Dihydro-1-methylcarbonylspiro [3H-indole-3,4'-piperdin]- 1'-yl)carbonyl]-2-(indol-3-yl)ethyl]-2-amino-2-methylpropanamide hydrochloride To 26 mg of the intermediate from Example 21, Step D in 1.0 mL of 1,2-dichloroethane and 55 µL (0.14 mmol) of N-methylmorpholine at 0° C. was added 6.6 µL (0.93 mmol) of acetyl chloride and stirred for 1 h. The reaction mixture was diluted with 5 mL of ether, washed-with 5 mL of 10% aqueous citric acid, 5 mL of saturated sodium bicarbonate solution, dried over anhydrous magnesium sulfate, filtered, and concentrated to give a pale yellow foam which was used without purification.

To the above material in 1.0 mL of dichloromethane was added 1.0 mL of trifluoroacetic acid and stirred at RT for 1 h. The reaction mixture was concentrated, basified with 5 mL of 10% aqueous sodium carbonate solution, and extracted with chloroform (3×5 mL). The combined organics were washed with brine (10 mL), dried over potassium carbonate, filtered, and concentrated to yield a thick oil. To a solution of this material in 1.0 mL of methanol was added 1.0 mL of 4M hydrochloric acid in dioxane and concentrated to dryness to yield 16 mg of the title compound as a pale yellow solid. The compound exists as a 3:2 mixture of rotamers. $^1$H NMR (CD$_3$OD, 400 MHz) δ8.43 (d, 1H), 8.35 (t, 1H), 7.72 (d, 2/3H), 7.61 (d, 1/3H), 7.40–7.25 (m, 2H), 7.20–7.08 (m, 3H), 7.05–6.95 (m, 22/3H), 6.50 (d, 1/3 H), 5.25–5.10 (m, 1H), 5.00–4.84 (2bd, 1H), 3.68–3.45 (m, 3H), 3.20 (m, 2H), 2.60–2.48 (m, 11/3H), 2.30 (dt, 1/3H), 2.00 (s, 1H), 1.98 (s, 2H), 1.81–1.40 (m, 4H), 1.35 (s, 2H), 1.33 (s, 2H), 1.32 (s, 1H), 1.30 (s, 1H), 1.25–1.15 (m, 1H), 1.10–1.00 (m, 1H), 0.20 (dt, 1/3H)

EXAMPLE 23

N-[1(R)-[(1,2-Dihydro-1-benzenesulfonylspiro [3H-indole-3,4 '-piperdin]-1'-yl)carbonyl]-2-(indol-3-yl)ethyl]-2- amino-2-methylpropanamide To 26 mg (0.050 mmol) of the intermediate from Example 21, Step D in 1.0 ml of 1,2-dichloroethane and 5 µl of N-methyl morpholine was added at 0° C. 7.5 µL of benzenesulfonyl chloride and stirred for 1 h. The reaction mixture was diluted with 10 ml of ether washed with 5 ml of 10% aqueous citric acid, 5 ml of saturated sodium bicarbonate solution, dried over anhydrous magnesium sulfate, filtered, and concentrated to give 29.8 mg of a crude product as a pale yellow foam. To a solution of this material in 2 ml of methanol was added 1.0 ml of conc. hydrochloric acid and stirred for 1 h. The solvent were removed under reduced pressure to yield the title compound as a brown solid. This compound exists as a 3:2 mixture of rotamers. $^1$H NMR(CDCl$_3$, 400 MHz) δ8.30 (bs, 1/3H), 8.20 (bs, 2/3H), 8.05 (bs, 2/3H), 7.88 (d, 1/3H), 7.72–7.45 (m, 5H), 7.43–7.30 (m, 4H), 7.20–7.05 (m, 2H), 7.00–6.90 (m, 22/3H), 6.35 (d, 1/3H), 5.25–5.10 (m, 1H), 4.90 (bs, 1H), 4.30 (dt, 1H), 4.15 (dt, 1H), 3.95 (dd, 1H), 3.60–3.40 (m, 3H), 3.25–3.20 (m, 2H), 2.90 (dt, 1H), 2.73 (dt, 22/3H), 2.35 (m, 11/3H), 1.80 (m, 1H), 1.50 (s, 1H), 1.43 (s, 2H), 1.39 (s, 3H), 1.30–1.20 (m, 2H), 1.00 (bd, 1/3H), 0.90–0.70 (m, 2H), 0.55 (bd, 1/3H), 0.48 (dd, 2/3H), -0.90 (dt, 1/3H)

EXAMPLE 24

N-[1(R)-[(1,2-Dihydro-1-methanesulfonylspiro [3H-indole-3,4 '-piperdin]-1'-yl)carbonyl]-2-(indol-3-yl)ethyl]-2- amino-2-methylpropanamide hydrochloride To a solution of 0.258 g (0.50 mmol) of the intermediate from Example 21, Step D in 10 mL of dry dichloromethane at 0° C. was added 0.39 mL (1.00 mmol) of N-methyl morpholine, and 45 µL (0.60 mmol) of methanesulfonyl chloride and stirred for 30 min. The reaction was diluted with 10 mL of ether and washed with saturated sodium bicarbonate solution (5 mL), brine (5 mL), dried over anhydrous magnesium sulfate, filtered, and concentrated to yield the product as a pale yellow foam which was used without purification. To a solution of this material in 3.0 mL of dichloromethane was added 1.0 mL of trifluoroacetic acid and stirred at RT for 1 h. The reaction mixture was concentrated, basified with 5 mL of 10% aqueous sodium carbonate solution, and extracted with chloroform (3×5 mL). The combined organics were washed with brine(10 mL), dried over potassium carbonate, filtered, and concentrated to yield a thick oil. To a solution of this material in 3.0 mL of methanol was added 200 µL of 4M hydrochloric acid in dioxane and concentrated to dryness to yield 98 mg of the desired material as a pale yellow solid. The compound exists as a 3:2 mixture of rotamers. $^1$H NMR (CD$_3$OD, 400 MHz) δ8.43 (d, 1H), 8.35 (t, 1H), 7.72 (d, 2/3H), 7.61 (d, 1/3H), 7.40–7.25 (m, 2H), 7.20–7.08 (m, 3H), 7.05–6.95 (m, 22/3H), 6.50 (d, 1/3H), 5.25–5.10 (m, 1H), 5.00–4.84 (2bd, 1H), 3.68–3.45 (m, 3H), 3.20 (m, 2H), 2.82 (s, 1H), 2.80 (s, 2H), 2.60–2.48 (m, 11/3H), 2.30 (dt, 1/3H), 1.81–1.40 (m, 4H), 1.35 (s, 2H), 1.33 (s, 2H), 1.32 (s, 1H), 1.30 (s, 1H), 1.25–1.15 (m, 1H), 1.10–1.00 (m, 1H), 0.20 (dt, 1/3H)

EXAMPLE 25

N-1(R)-[1,2-Dihydro-1-methanesulfonylspiro[3H-indole-3,4'-piperidin]-1'-yl)carbonyl]-[3-phenylpropyl]-2-amino-2-methylpropanamide hydrochloride Step A: N-1(R)-[1,2-Dihydro-1-methanesulfonylspiro[3H-indole- 3,4 '-piperdin]-1'-yl)carbonyl]-3-phenylpropyl]-2-[( 1,1-dimethylethoxy)carbonyl]amino-2-methylpropanamide The title compound was prepared from (2R)-2-[(1,1-dimethylethoxy)carbonyl]amino- 4-phenyl-1-butanoic acid and 1,2-dihydro-1 -methylsulfonylspiro[3H-indole-3,4'-piperidine]hydrochloride by using the coupling method as described in Example 18, Step B. The crude product was purified on silica gel using 5% Acetone in CH$_2$Cl$_2$.

$^1$H NMR (400 MHz, CDCl$_3$) δ7.2 (m, 9H), 4.9 (m, 1H), 4.5 (m, 1H), 3.8 (m, 2H), 3.2 (m, 2H), 2.9 (s, 3H), 2.7 (m, 2H), 2.3 (s, 2H), 2.0 (m, 2H), 1.7 (m, 4H), 1.5 (s, 6H), 1.4 (s, 9H).

Step B: N-1(R)-[1,2-Dihydro-1-methanesulfonylspiro[3H-indole- 3,4'-piperidin]-1'-yl)carbonyl]-3-phenylpropyl]-2-amino- 2-methylpropanamide hydrochloride Prepared from the intermediate obtained in step A using the deprotection method as described in Example 18, Step C.

$^1$H NMR (400 MHz, CD$_3$OD) δ7.3 (m, 9H), 4.5 (m, 1H), 3.9 (m, 2H), 3.5 (m, 2H), 3.2 (m, 2H), 2.9 (s, 3H), 2.7 (m, 4H), 2.0 (m, 4H), 1.6 (s, 6H).

EXAMPLE 26

N-[1(R)-[(1,2-Dihydro-1-trifluoromethanesulfonyl-5-fluoro-spiro[3 H-indole-3,4'-piperdin]-1'-yl)carbonyl]-2-(indol-3-yl) ethyl]-2-amino-2-methylpropanamide trifluoroacetate Step A: 1,2-Dihydro-1-benzyloxycarbonyl-5-fluoro-spiro[3 H-indole-3,4'-piperdine]

To 7.82 g of 60% sodium hydride was added hexane and the liquids were decanted. To this was added a solution of 11.10 mL (89 mmol) of 2,5-difluorophenylacetonitrile in 150 mL of DMSO and stirred for 30 min. A solution of 15.10 g of 1-chloromethyl ethylamine hydrochloride in 150 mL of DMSO was added dropwise and heated at 75° C. for 4 h. The reaction mixture was poured into 600 g of ice and extracted with ether (5×200 mL). The combined organics were washed with 3×100 mL of 2N hydrochloric acid. The combined aqueous extracts were basified to pH=9 with 50% aqueous sodium hydroxide and extracted with ether (3×200 mL). The combined organics were washed with brine (100 mL), dried over potassium carbonate and concentrated to give 15.54 g of a thick oil.

Ethanol (24 mL) was added in dropwise fashion to 9.90 g of lithium aluminum hydride in 250 mL of DME at 0° C. and then warmed to reflux. A solution of the compound in 250 mL of DME was added and refluxed for 72 h. The reaction was then cooled to 0° C. and quenched with water (10 mL), 10 mL of 15% NaOH, and 30 mL of water. The slurry was dried over K$_2$CO$_3$, filtered, and concentrated to give 13.6 g of a thick oil. This crude product was triturated with hexanes, the solid was filtered, and washed further with hexanes. 200 MHz NMR (CDCl$_3$) of the solid (2.6 g) indicated about 75% of the desired spiro-indoline.

To a solution of 1.02 g of this mixture in 50 mL of CH$_2$Cl$_2$ at 0° C. was added 1.0 mL of trimethylamine and 0.80 mL of CBZ-Cl and stirred for 1 h at RT. The reaction mixture was poured into 50 mL of 5% HCl and the aqueous layer was separated. The aqueous layer was basified with 50% NaOH to pH=10 and extracted with CH$_2$Cl$_2$ (3×25 mL). The combined organics were washed with brine (50 mL), dried over K$_2$CO$_3$, and concentrated to yield 1.26 g of the compound as a thick oil.

$^1$H NMR (200 MHz, CDCl$_3$) δ7.7–7.90 (m, 1H), 7.50–7.15 (m, 6H), 6.95–6.60 (m, 2H), 5.28 (bs, 2H), 3.90 (bs, 2H), 2.85 (bd, 2H), 2.30 (s, 3H), 2.20–1.80 (m, 4H), 1.65 (bd, 2H).

Step B: N-[1(R)-[(1,2-Dihydro-1-benzyloxycarbonyl-5-fluoro-spiro[3H-indole-3,4'-piperidin]-1'-yl)carbonyl]-2-(indol- 3-yl)ethyl]-[[(1,1-dimethylethyloxy)carbonyl]amino]- 2-methylpropanamide To 1.62 g (4.62 mmol) of the above intermediate from Step A in 10 mL of 1,2-dichloroethane at 0° C. was added 0.65 mL of ACE-Cl and refluxed for 1 h. The reaction mixture was concentrated to one-third the volume and diluted with 10 mL of methanol and heated to reflux for 1 h. The reaction mixture was concentrated to dryness and triturated with ether to give brown solid. This material was dissolved in saturated sodium bicarbonate solution (25 mL), and extracted with dichloromethane (2×25 mL). The combined organics were dried over K$_2$CO$_3$ and concentrated to give 0.384 g of the free base.

To 0.384 g of this material in 15 mL of CH$_2$Cl$_2$ was added 0.483 g of the acid intermediate obtained from Step C of Example 21, 0.189 g of HOBT, and 0.34 g of EDC and stirred for 18 h. The reaction mictured was poured into 10 mL of water and extracted with CH$_2$Cl$_2$ (2×10 mL). The combined organics were washed with 20 mL of 10% citric acid, 20 mL of saturated NaHCO$_3$, dried over MgSO$_4$, and concentrated. Flash chromatographed of the residue on 25 g of silica gel with hexanes-acetone (1:1) as eluent gave 0.389 g of the desired material.

$^1$H NMR (200 MHz, CDCl$_3$) δ7.7–7.90 (m, 1H), 7.50–7.15 (m, 6H), 6.95–6.60 (m, 2H), 5.28 (bs, 2H), 3.90 (bs, 2H), 2.85 (bd, 2H), 2.30 (s, 3H), 2.20–1.80 (m, 4H), 1.65 (bd, 2H).

Step C: N-[1(R)-[(1,2-Dihydro-5-fluoro-spiro[3H-indole-3,4'-piperdin]-1'-yl)carbonyl]-2-(indol-3-yl)ethyl]-[[(1,1-dimethylethyloxy)carbonyl]amino]-2-methylpropanamide To a solution of 0.363 g of the intermediate obtained from Step B in 5 mL of of ethanol was added 0.10 g of 20% palladium hydroxide on carbon and hydrogenated under H$_2$ balloon for 1 h. the catalyst was filtered off and washed with more methanol. The filtrate was concentrated to yield 0.262 g of the desired material.

$^1$H NMR (400 MHz, CDCl$_3$) This material was 2:1 mixture of rotamers. δ8.85–8.60 (2bs, 1H), 7.70(d, 2/3H), 7.55 (d, 1/3H), 7.38 (d, 2/3H), 7.30 (d, 1/3H), 7.28–7.15 (m, 4H), 7.13–7.02 (m, 2H), 6.65 (dt, 2H), 6.50 (dd, 1/3H), 6.45 (dd, 2/3H), 6.14 (dd, 2/3H), 5.30–5.13 (m, 1H), 5.10 (bs, 1H), 4.30 (bd, 2/3H), 422 (bd, 1/3H), 3.50–3.30 (m, 1H), 3.30–3.00 (m, 4H), 3.00–2.80 (m, 1H), 2.73 (t, 1H), 2.53–2.40 (m, 11/3H), 2.20 (t, 1/3H), 1.49 (s, 3H), 1.45 (s, 3H), 1.41 (s, 9H) 1.20 (dt, 1/3H), 0.95 (bd, 2/3H), 0.90 (dt, 2/3H), -0.05 (dt, 1/3H).

Step D: N-[1(R)-[(1,2-Dihydro-1-trifluoromethanesulfonyl-5-fluoro-spiro[3 H-indole-3,4'-piperdin]-1'-yl)carbonyl]-2-(indol-3-yl)ethyl]-[[(1,1-dimethylethyloxy)carbonyl]amino]- 2-methylpropanamide To a solution of 30 mg of the intermediate obtained from Step C in 1 mL of dichloromethane at 0° C. was added 0.050 mL of triethylamine and 0.020 mL of triflic anhydride and stirred for 5 min. the catalyst was filtered off and washed with more methanol. The reaction was poured into 5 mL of 5% aqueous sodium carbonate solution and stirred for 5 min. The aqueous layer was extracted with CH$_2$Cl$_2$ (2×5 mL) and the combined organics were dried over MgSO$_4$, filtered, and concentrated. Flash chromatography of the residue on 3 g of silica gel with CH$_2$Cl$_2$-acetone (4:1) as eluent gave 21 mg of product.

$^1$H NMR (400 MHz, CDCl$_3$) This material was 2:1 mixture of rotamers. δ8.40 (bs, 2/3H), 8.25 (bs, 1/3H), 7.70(d, 2/3H), 7.60 (d, 1/3H), 7.40 (d, 2/3H), 7.35–7.10 (m, 5H), 6.90–6.80 (m, 2H), 6.18 (dd, 1H), 5.30–5.13 (m, 1H), 4.95(bs, 2/3H), 4.90 (s, 1/3H), 4.45 (bd, 2/3H), 4.35 (bd, 1/3H), 385–3.70 (m, 2H), 3.70–3.55 (m, 2H), 3.30–3.10 (m, 2H), 2.70 (t, 1H), 2.45 (t, 1/3H), 2.35 (t, 2/3H), 1.49 (s, 3H), 1.45 (s, 3H), 1.41 (s, 9H), 1.20 (dt, 1/3H), 0.95 (bd, 2/3H), 0.90 (dt, 2/3H), -0.05 (dt, 1/3H).

Step E: N-[1(R)-[(1,2-Dihydro-1-trifluoromethanesulfonyl-5-fluoro-spiro[3H-indole-3,4'-piperdin]-1'-yl)carbonyl]-2-(indol-3-yl)ethyl]-2-methylpropanamide trifluoroacetate To a solution of 21 mg of the intermediate obtained from Step D was maintained in 1 mL of dichloromethane and 1 mL of trifluoroacetic acid at room temperature for 30 min. The volatiles were evaporated to dryness and triturated with ether to give a yellow solid.

$^1$H NMR (400 MHz, CD$_3$OD) This material was 2:1 mixture of rotamers. δ7.65(d, 2/3H), 7.60 (d, 1/3H), 7.42 (d, 2/3H), 7.35–7.10 (m, 5H), 6.93–6.80 (m, 2H), 6.24 (dd, 1H), 5.30–5.13 (m, 1H), 4.95(bs, 2/3H), 4.90 (s, 1/3H), 4.45 (bd, 2/3H), 4.35 (bd, 2/3H), 385–3.70 (m, 2H), 3.70–3.55 (m, 2H), 3.30–3.10 (m, 2H), 2.70 (t, 1H), 2.45 (t, 1/3H), 2.35 (t, 2/3H), 1.49 (s, 3H), 1.45 (s, 3H), 0.93 (bd, 2/3H), 0.90 (dt, 2/3H), -0.05 (dt, 1/3H).

EXAMPLE 27

N-[1(R)-[(1,2-Dihydro-1-[methoxycarbonyl]methylsulfonyl-5-fluoro-spiro-[3H-indole-3,4'-piperdin]]-1'-yl)carbonyl]-2-(indol-3-yl)ethyl]-2-amino-2-methylpropanamide trifluoroacetate Step A: N-[1(R)-[(1,2-Dihydro-1-[methoxycarbonyl]methylsulfonyl- 5-fluoro-spiro[3H-indole-3,4'-piperdin]]-1'-yl)carbonyl]-2-(indol-3-yl)ethyl]-2-methylpropanamide trifluoroacetate To a solution of 77 mg of the intermediate obtained from Step C of Example 26 in 1 mL of dichloromethane at 0° C. was added 0.30 mL of N-methylmorpholine, and 0.024 mL of 2-carbomethoxymethanesulfonylchloride and stirred for 1 h. The reaction was poured into 5 mL of 5% aqueous sodium carbonate solution and stirred for 5 min. The aqueous layer was extracted with CH$_2$Cl$_2$ (2×5 mL) and the combined organics were washed with brine (5 mL), dried over MgSO$_4$, filtered, and concentrated. Flash chromatography of the residue on 5 g of silica gel with CH$_2$Cl$_2$-acetone (4:1) as eluent gave 64 mg of product.

$^1$H NMR (400 MHz, CDCl$_3$) This material was 2:1 mixture of rotamers. δ8.48 (bs, 2/3H), 8.35 (bs, 1/3H), 7.70(d, 2/3H), 7.60 (d, 1/3H), 7.40 (d, 2/3H), 7.32 (d, 1/3H), 7.25–7.00 (m, 4H), 6.90–6.78 (m, 2H), 6.18 (dd, 1H), 5.30–5.20 (m, 1H), 4.97(bs, 2/3H), 4.91 (s, 1/3H), 4.50–4.35 (2bd, 1H), 4.02 (s, 2/3H), 3.99 (s, 1/3H), 3.76(q, 2H), 3.58 (s, 1H), 3.56 (s, 2H), 3.08–3.07 (m, 2H), 2.72 (t, 1H), 2.50–2.30 (2t, 1H), 1.65 (t, 1/3H), 1.50 (s, 2H), 1.46 (s, 4H), 1.40 (s, 9H), 1.30 (m, 1/3H), 1.10 (bd, 2/3H), 0.88 (dt, 2/3H), -0.13 (dt, 1/3H).

Step B: N-[1(R)-[(1,2-Dihydro-1-[methoxycarbonyl]methylsulfonyl-5-fluoro-spiro[3H-indole-3,4'-piperdin]]-1'-yl)carbonyl]-2-(indol-3-yl)ethyl]-2-methylpropanamide trifluoroacetate To a solution of 24 mg of the intermediate obtained from Step A was maintained in 1 mL of dichloromethane and 1 mL of trifluoroacetic acid at room temperature for 30 min. The volatiles were evaporated to dryness and triturated with ether to give 23 mg of a colorless solid.

$^1$H NMR (400 MHz, CD$_3$OD) This material was 2:1 mixture of rotamers. δ8.70 (bs, 1/3H), 8.60 (bs, 2/3H), 7.60 (m, 2/3H), 7.50 (d, 2/3H), 7.48 (m, 1/3H), 7.40 (d, 2/3H), 7.31 (d, 1/3H), 7.25–7.00 (m, 4H), 6.95–6.85 (m, 1H), 6.70 (dd, 1/3H), 6.15 (dd, 2/3H), 5.20–5.10 (m, 1H), 4.38 (bd, 1/3H), 4.28 (bd, 2/3H), 4.02 (s, 2/3H), 3.99 (s, 1/3H), 3.76(q, 2H), 3.58 (s, 1H), 3.56 (s, 2H), 3.08–3.07 (m, 2H), 2.72 (t, 1H), 2.50–2.30 (2t, 1H), 1.65 (t, 1/3H), 1.65 (s, 2H), 1.60 (s, 4H), 1.30 (m, 1/3H), 1.00 (bd, 2/3H), 0.88 (dt, 2/3H), -0.10 (dt, 1/3H).

EXAMPLE 28

N-[1(R)-[(1,2-Dihydro-1-methanesulfonyl-5-fluoro-spiro [3H-indole-3,4'-piperdin]-1'-yl)carbonyl]-2-(phenylmethyloxy)ethyl]-2-amino-2-methylpropanamide hydrochloride Step A: N-[1(R)-[(1,2-Dihydro-1-benzyloxycarbonyl-5-fluoro-spiro[3H-indole-3,4'-piperdin]-1'-yl)carbonyl]-2-(phenylmethyloxy)ethyl]-[[(1,1-dimethylethyloxy)carbonyl]amino]- 2-methylpropanamide To 0.330 g of the 1,2-Dihydro-1-benzyloxycarbonyl-5-fluoro-spiro[3H-indole-3,4'-piperdine]obtained from Step A of Example 26 in 10 mL of 1,2-dichloromethane at room temperature was added 0.35 g of N-tBOC-O-benzyl-D-serine, 0.195 g of HOBT, and 0.30 g of EDC and stirred for 18 h. The reaction mictured was poured into 10 mL of water and extracted with CH₂Cl₂ (2×10 mL). The combined organics were washed with 20 mL of 10% citric acid, 20 mL of saturated NaHCO₃, dried over MgSO₄, and concentrated.

To a solution of the intermediate obtained from Step A in 5 mL of CH₂Cl₂ was added 5 mL of trifluoroacetic acid and stirred at RT for 30 min. The reaction mixture was concentrated, diluted with 5.0 mL of dichloromethane and carefully basified with 10 mL of 10% aqueous sodium carbonate solution. The organic layer was separated and the aqueous layer was further extracted with 2×15 mL of dichloromethane. The combined organics were washed with 5 mL of water, dried over potassium carbonate, filtered and concentrated to give 0.39 g of the amine as a thick oil.

To 0.39 g of the above intermediate in 10 mL of 1,2-dichloromethane at room temperature was added 0.24 g of N-tBOC-α-methylalanine, 0.195 g of HOBT, and 0.30 g of EDC and stirred for 18 h. The reaction mixtured was poured into 10 mL of water and extracted with CH₂Cl₂ (2×10 mL). The combined organics were washed with 20 mL of 10% citric acid, 20 mL of saturated NaHCO₃, dried over MgSO₄, and concentrated. Flash chromatography of the residue over 30 g of silica gel with hexane-ethyl acetate (2:1) as eluent gave 0.33 g of product ¹H NMR (200 MHz, CDCl₃) δ7.80(bs, 1H), 7.50–7.15 (m, 5H), 7.10(bd, 1H), 6.90–6.70(m, 1H), 6.27 (bd, 1H), 7.35–7.10 (m, 5H), 5.35–5.10 (m, 3H), 4.99 (s, 1H), 4.70–4.40 (m, 3H), 3.90–3.50 (m, 4H), 3.15–2.90 (m, 2H), 2.80–2.50 (m, 2H), 1.80–1.40 (m, 2H), 1.50 (3H), 1.42 (s, 6H).

Step B: N-[1(R)-[(1,2-Dihydro-5-fluoro-spiro[3H-indole-3,4'-piperdin]-1'-yl)carbonyl]-2-(phenylmethyloxy) ethyl]-[[(1,1-dimethylethyloxy)carbonyl]amino]-2-methylpropanamide To a solution of 0.330 g of the intermediate obtained from Step A in 5 mL of ethanol at was added 1 drop of triethylamine and hydrogenated with hydrogen balloon for 3 h. The catalyst was filtered off through a pad of celite and washed with ethyl acetate. The filtrate was concentrated to give 0.269 g of the product as a colorless foam.

¹H NMR (400 MHz, CDCl₃) δ7.35–7.20 (m, 4H), 7.17–7.08 (m, 2H), 6.80–6.65 (m, 22/3H), 6.27 (dt, 1/3H), 5.20–5.10 (m, 1H), 4.90 (s, 1H), 4.60–4.40 (m, 3H), 4.00 (bt, 1H), 3.75–3.60 (m, 1H), 3.55–3.40 (m, 3H), 3.18–3.30 (m, 2H), 2.90–2.65 (m, 1H), 1.83–1.50 (m, 4H), 1.48 (s, 4H), 1.42 (s, 2H), 1.39 (s, 9H).

Step C: N-[1(R)-[(1,2-Dihydro-1-methanesulfonyl-5-fluoro-spiro[3H-indole-3,4'-piperdin]-1'-yl)carbonyl]-2-(phenylmethyloxy)ethyl]-[[(1,1-dimethylethyloxy)carbonyl]amino]- 2-methylpropanamide To a solution of 0.134 g the intermediate from Step B in 5 mL of dichloromethane was added 0.080 mL of N-methylmorpholine, and 0.022 mL of methanesulfonylchloride and stirred at 0° C. for 30 min. The reaction mixture was diluted with an additional 5 mL of dichloromethane and washed with 5 mL of saturated sodium bicarbonate solution, brine (5 mL), dried over MgSO4 and concentrated. Flash chromatography of the residue over 20 g of silica gel gave 0.101 g of the desired product.

¹H NMR (400 MHz, CDCl₃) δ7.40–7.20 (m, 5H), 7.08 (d, 1H), 6.95–6.80 (m, 2/1/3H), 6.23 (dd, 2/3H), 5.20–5.10 (m, 1H), 4.90 (bs, 1H), 4.60 (bd, 2/3H), 4.58–4.40 (m, 3/1/3H), 4.10–4.00 (m, 1H), 3.388–3.70 (m, 21/3H), 3.66–3.60 (m, 1/2H), 3.60–3.50 (m, 1H), 3.10–2.95 (m, 1H), 2.86 (s, 1H), 2.84 (s, 2H), 2.80 (t, 1/3H), 2.65 (t, 2/3H), 2.90–2.50 (m, 4H), 1.45 (s, 4H), 1.44 (s, 2H), 1.42 (s, 3H), 1.40 (s, 6H).

Step D: N-[1(R)-[(1,2-Dihydro-1-methanesulfonyl-5-fluoro-spiro[3H-indole-3,4'-piperdin]-1'-yl)carbonyl]-2-(phenylmethyloxy)ethyl]-2-amino-2-methylpropanamide hydrochloride To a solution of 0.101 g the intermediate from Step C in 1 mL of dichloromethane was added 1.0 mL of trifluoroacetic acid and maintained at RT for 30 min. The reaction mixture was evaporated to dryness, basified with 10% aqueous sodium carbonate solution (10 mL), and extracted with dichloromethane (3×5 mL). The combined organics were washed with brine (5 mL), dried over potassium carbonate, and concentrated. This material was dissolved in 2 mL of ethyl acetate and 0.10 mL of 4M HCl in EtOAc was added at 0° C. The precipitate was filtered under nitogen and washed with EtOAc/ether (1:1) and dried to give 62 mg of the product as a white solid.

¹H NMR (400 MHz, CD₃OD) δ7.40–7.20 (m, 5H), 7.08 (d, 1H), 6.95–6.80 (m, 2/1/3H), 6.23 (dd, 2/3H), 5.20–5.10 (m, 1H), 4.60 (bd, 2/3H), 4.58–4.40 (m, 3/1/3H), 4.10–4.00 (m, 1H), 3.388–3.70 (m, 21/3H), 3.66–3.60 (m, 1/2H), 3.60–3.50 (m, 1H), 3.10–2.95 (m, 1H), 2.86 (s, 1H), 2.84 (s, 2H), 2.80 (t, 1/3H), 2.65 (t, 2/3H), 2.90–2.50 (m, 4H), 1.45 (s, 4H), 1.44 (s, 2H).

EXAMPLE 29

Step A: N-[1(R)-[(1,2-Dihydro-1-benzenesulfonyl-5-fluoro-spiro[3H-indole-3,4'-piperdin]-1'-yl)carbonyl]-2-(phenylmethyloxy)ethyl]-2-amino-2-methylpropanamide trifluoroacetate To a solution of 0.026 g the intermediate from Step B of Example 27 in 2 mL of dichloromethane was added 0.020 mL of N-methylmorpholine, and 0.012 mL of benzeneesulfonylchloride and stirred at 0° C. for 1 h. The reaction mixture was poured into 10 mL of ether and washed with 5 mL of saturated sodium bicarbonate solution, dried over MgSO₄ and concentrated. Flash chromatography of the residue over 10 g of silica gel with CH₂Cl₂-ether (2:1) as eluent gave 0.019 g of the product.

This material was treated with 1 mL of dichloromethane and 1 mL of trifluoroacetic acid for 1 h. The reaction mixture was evaporated to dryness and the residue was triturated with ether to give 18 mg of the desired product as a white solid.

¹H NMR (400 MHz, CD₃OD) δ7.80 (d, 2H), 7.70–7.55 (m, 2H), 7.55–7.50 (m, 2H), 7.40–7.20 (m, 42/3H), 7.03–6.92 (m, 1H), 6.82 (dt, 2/3H), 6.47 (dt, 2/3H), 5.08 (dt, 1H), 4.60–4.48 (m, 2H), 4.33 (bt, 1H), 3.94–3.85 (m, 3H), 3.75–3.65 (m, 2H), 3.10 (dt, 1H), 2.80 (dt, 1H), 1.73 (dt, 1H), 1.58 (s, 4H), 1.56 (s, 2H), 1.50 (dt, 1H), 1.38 (dt, 1H), 1.10 (dt, 2H).

EXAMPLE 30

N-[1(R)-[(1,2-Dihydro-1-ethanesulfonyl-spiro [3H-indole-3,4'-piperdin]-1'-yl)carbonyl]-2-(phenylmethyloxy)ethyl]-2-amino-2-methylpropanamide hydrochloride Step A: N-[1(R)-[(1,2-Dihydro-1-benzyloxycarbonyl-spiro[3 H-indole-3,4'-piperdin]-1'-yl)carbonyl]- 2-(phenylmethyloxy)ethyl]-[[(1,1-dimethylethyloxy)carbonyl] amino]- 2-methylpropanamide To 5 g of the 1,2-Dihydro-1-benzyloxycarbonyl-spiro[3 H-indole-3,4'-piperdine]hydrochloride in 100 mL of dichloromethane at room temperature was added 3.64 g of N-tBOC-O-benzyl-D-serine, 1.83 g of HOBT, 2.60 mL of N-methylmorpholine, and 3.70 g of EDC and stirred for 18 h. The reaction mixture was poured into 100 mL of water and extracted with CH₂Cl₂ (2×100 mL). The combined organics were washed with 100 mL of 10% citric acid, 100 mL of saturated NaHCO$_3$, dried over MgSO$_4$, and concentrated.

To a solution of the intermediate obtained from Step A in 20 mL of CH$_2$Cl$_2$ was added 20 mL of trifluoroacetic acid and stirred at RT for 30 min. The reaction mixture was concentrated, diluted with 50 mL of dichloromethane and carefully basified with 100 mL of 10% aqueous sodium carbonate solution. The organic layer was separated and the aqueous layer was further extracted with 2×50 mL of dichloromethane. The combined organics were washed with 50 mL of water, dried over potassium carbonate, filtered and concentrated to give the amine as a thick oil.

To the above intermediate in 50 mL of dichloromethane at room temperature was added 2.50 g of N-tBOC-α-methylalanine, 1.83 g of HOBT, and 3.70 g of EDC and stirred for 18 h. The reaction mixtured was poured into 10 mL of water and extracted with CH$_2$Cl$_2$ (2×10 mL). The combined organics were washed with 20 mL of 10% citric acid, 20 mL of saturated NaHCO$_3$, dried over MgSO$_4$, and concentrated. Flash chromatography of the residue over 300 g of silica gel with hexane-ethyl acetate (2:1) as eluent gave 8.1 g of product $^1$H NMR (400 MHz, CDCl$_3$) δ7.85(bs, 1H), 7.45–7.20 (m, 10H), 7.20–7.05 (m, 22/3H), 6.95 (t, 1/3H), 6.88(t, 1/3H), 6.53 (dd, 2/3H), 5.35–5.20 (m, 2H), 5.20–5.10 (m, 1H), 4.92 (bs, 1H), 4.65–4.20 (m, 4H), 4.05 (bd, 2/3H), 4.00–3.80 (m, 1,1/3H), 3.80–3.60 (m, 1H), 3.10 (t, 2/3H), 3.00–2.85 (m, 1/3H), 2.82–2.60 (2t, 1H), 1.90–1.55 (m, 5H), 1.49 (s, 4H), 1.42 (s, 2H), 1.40 (s, 9H).

Step B: N-[1(R)-[(1,2-Dihydro-spiro[3H-indole-3,4'-piperdin]- 1'-yl)carbonyl]-2-(phenylmethyloxy)ethyl]-[[( 1,1-dimethylethoxy)carbonyl]amino]-2-methylpropanamide To a solution of 8.10 g of the intermediate obtained from Step A in 80 mL of ethanol was added 1 g of 20% palladium hydroxide/C and hydrogenated with hydrogen balloon for 1 h. The catalyst was filtered off through a pad of celite and washed with ethyl acetate. The filtrate was concentrated to give 4.69 g of the product as a colorless foam.

$^1$H NMR (400 MHz, CDCl$_3$) δ7.35–7.20 (m, 5H), 7.18 (d, 1/2H), 7.10 (d, 1/2H), 7.04–6.98 (m, 2H), 6.75–6.60 (m, 2H), 5.20–5.10 (m, 1H), 4.97 (bs, 1H), 4.55–4.40 (m, 3H), 3.95 (dd, 1H), 3.73–3.61 (m, 1H), 3.60–3.50 (m, 1H), 3.50–3.33 (m, 3H), 3.10 (dt, 1H), 2.83 (dt, 1H), 1.85–1.55 9m, 5H), 1.47 (s, 4H), 1.42 (s, 2H), 1.39 (s, 9H).

Step C: N-[1(R)-[(1,2-Dihydro-1-ethanesulfonyl-spiro[3H-indole- 3,4'-piperdin]-1'-yl)carbonyl]-2-(phenylmethyloxy)-ethyl]- 2-amino-2-methylpropanamide To a solution of 0.158 g the intermediate from Step B in 5 mL of dichloromethane was added 0.053 mL of N-methylmorpholine, and 0.034 mL of ethanesulfonylchloride and stirred at 0° C. for 30 min and RT for 1 h. The reaction mixture was diluted with an additional 5 mL of dichloromethane and washed with 5 mL of saturated sodium bicarbonate solution, brine (5 mL), dried over MgSO$_4$ and concentrated. Flash chromatography of the residue over 10 g of silica gel with CH$_2$Cl$_2$-ether (3:1) as eluent gave 0.057 g of the desired product.

To a solution of 0.057 g the above intermediate in 1 mL of dichloromethane was added 1.0 mL of trifluoroacetic acid and maintained at RT for 30 min. The reaction mixture was concentrated to dryness and triturated with ether to give 0.034 g of the product as a yellow solid.

$^1$H NMR (400 MHz, CD$_3$OD) δ 7.40–7.25(m, 5H), 7.25–7.13 (m, 21/2H), 7.03 (t, 1/2H), 6.95 (t, 1/2H), 6.80 (d, 1/2H), 5.18 (dt, 1H), 4.60–4.42 (m, 3H), 4.08 (t, 1H), 3.96 (s, 2H), 3.83–3.70 (m, 2H), 3.29–3.15 (m, 3H), 2.84 (dt, 1H), 1.90 (dt, 1H), 1.74–1.62 (m, 4H), 1.62 (s, 2H), 1.60 (s, 4H), 1.33 (dt, 3H).

EXAMPLE 31

Step A: N-[1(R)-[(1,2-Dihydro-1-[2-methyl-2-propanesulfonyl-spiro[3H-indole-3,4'-piperdin]]-1'-yl)carbonyl]-2-(phenylmethyloxy)ethyl]-[[(1,1-dimethylethyloxy)carbonyl]amino]-2-methylpropanamide To a solution of 0.212 g the intermediate from Step B of Example 29 in 2 mL of 1,2-dichloroethane was added 0.083 mL of triethylamine, and 0.054 mL of isopropylsulfonylchloride and stirred at 0° C. for 30 min and at RT for 3 h. The reaction mixture was diluted with a 5 mL of dichloromethane and washed with 5 mL of saturated sodium bicarbonate solution, brine (5 mL), dried over MgSO$_4$ and concentrated. Flash chromatography of the residue over 10 g of silica gel with CH$_2$Cl$_2$-ether (3:1) as eluent gave 0.113 g of the desired product.

To a solution of 0.101 g the above intermediate in 1 mL of dichloromethane was added 1.0 mL of trifluoroacetic acid and maintained at RT for 30 min. The reaction mixture was evaporated to dryness, basified with 10% aqueous sodium carbonate solution (10 mL), and extracted with dichloromethane (3×5 mL). The combined organics were washed with brine (5 mL), dried over potassium carbonate, and concentrated. This material was dissolved in 2 mL of ethyl acetate and 0.10 mL of 4M HCl in EtOAc was added at 0° C. The precipitate was filtered under nitrogen and washed with EtOAc/ether (1:1) and dried to give 88 mg of the product as a white solid.

$^1$H NMR (400 MHz, CD$_3$OD) a 7.40–7.20 (m, 5H), 7.08 (d, 1H), 6.95–6.80 (m, 2/1/3H), 6.23 (dd, 2/3H), 5.20–5.10 (m, 1H), 4.60 (bd, 2/3H), 4.58–4.40 (m, 3/1/3H), 4.10–4.00 (m, 1H), 3.388–3.70 (m, 21/3H), 3.66–3.60 (m, 1/2H), 3.60–3.50 (m, 1H), 3.10–2.95 (m, 1H), 2.86 (s, 1H), 2.84 (s, 2H), 2.80 (t, 1/3H), 2.65 (t, 2/3H), 2.90–2.50 (m, 4H), 1.45 (s, 4H), 1.44 (s, 2H).

EXAMPLE 32

Step A: N-[1(R)-[(1,2-Dihydro-1-[2-carbomethoxymethanesulfonyl-spiro[3H-indole-3,4'-piperdin]]-1'-yl)carbonyl]- 2-(phenylmethyloxy)ethyl]-[[(1,1-dimethylethyloxy)carbonyl]amino]-2-methylpropanamide hydrochloride To a solution of 0.50 g the intermediate from Step B of Example 29 in 10 mL of dichloromethane was added 0.21 mL of N-methylmorpholine and 0.10 mL of 2-carbomethoxymethanesulfonylchloride and stirred at 0° C. for 30 min. The reaction mixture was diluted with 10 mL of dichloromethane and washed with 5 mL of saturated sodium bicarbonate solution, brine (5 mL), dried over MgSO$_4$ and concentrated. Flash chromatography of the residue over 20 g of silica gel with CH$_2$Cl$_2$-ether (3:1 ) as eluent gave 0.529 g of the desired product.

$^1$H NMR (400 MHz, CDCl$_3$) a 7.39–7.20 (m, 5H), 7.20–7.10 (m, 21/2H), 7.08 (dt, 1H), 6.92 (t, 1/2H), 6.55 (d, 1/2H), 5.20–5.10 (m, 1H), 4.94 (bs, 1H), 4.60 (bd, 1H), 4.53–4.40 (m, 2H), 4.10 (2bs, 2H), 4.05–3.90 (m, 2H), 3.70 (dt, 1H), 3.63 (s, 11/2H), 3.61 (s, 11/2H), 3.59–3.50 (m, 1H), 3.05 (dt, 1H), 2.70 (dt, 1H0, 1.90–1.50 (m, 4H), 1.49 (s, 4H), 1.44 (s, 2H), 1.39 (s, 9H).

Step B: N-[1(R)-[(1,2-Dihydro-1-[2-carbomethoxymethanesulfonyl-spiro[3H-indole-3,4'-piperdin]]-1'-yl)carbonyl]- 2-(phenylmethyloxy)ethyl]-2-amino-2-methylpropanamide hydrochloride To a solution of 0.113 g the above intermediate in 1 mL of dichloromethane was added 1.0 mL of trifluoroacetic acid and maintained at RT for 30 min. The reaction mixture was evaporated to dryness, basified with 10% aqueous sodium carbonate solution (10 mL), and extracted with dichloromethane (3×5 mL). The combined organics were washed with brine (10 mL), dried over potassium carbonate, and concentrated. This material was dissolved in 2 mL of ethyl acetate and 0.20 mL of 4M HCl in EtOAc was added at 0° C. Ether was added and the precipitate was filtered under nitogen and washed with ether and dried to give 0.108 g of the product as a white solid.

$^1$H NMR (400 MHz, CD$_3$OD) a 7.40–7.20 (m, 5H), 7.08 (d, 1H), 6.95–6.80 (m, 2/1/3H), 6.23 (dd, 2/3H), 5.20–5.10 (m, 1H), 4.60 (bd, 2/3H), 4.58–4.40 (m, 3/1/3H), 4.10–4.00 (m, 1H), 3.388–3.70 (m, 21/3H), 3.66–3.60 (m, 1/2H), 3.60–3.50 (m, 1H), 3.10–2.95 (m, 1H), 2.86 (s, 1H), 2.84 (s, 2H), 2.80 (t, 1/3H), 2.65 (t, 2/3H), 2.90–2.50 (m, 4H), 1.45 (s, 4H), 1.44 (s, 2H).

EXAMPLE 33

Step A: N-[1(R)-[(1,2-Dihydro-1-[2-carboxymethanesulfonyl-spiro[3H-indole-3,4'-piperdin]]-1'-yl)carbonyl]-2-(phenylmethyloxy)ethyl]-[[(1,1-dimethylethyloxy)carbonyl]amino]-2-methylpropanamide trifluoroacetate To a solution of 0.126 g the intermediate from Step A of Example 32 in 3 mL of methanol and 1 mL of water at 0° C. was added 2 drops of 5N aqueous sodium hydroxide and stirred for 30 min. The reaction mixture was acidified to pH=2 with 0.50N aqueous hydrochloric acid, diluted with brine (5 mL), and extracted with CH$_2$Cl$_2$ (2×5 mL). The combined organics were washed with brine(10 mL), dried over MgSO$_4$ and concentrated to give 0.098 g of a white foam.

$^1$H NMR (400 MHz, CDCl$_3$) δ9.80 (bs, 1H), 7.45 (d, 1/2H), 7.40–7.13 (m, 7H), 7.02 (t, 1/2H), 6.90 (t, 1/2H), 6.50 (d, 1/2H), 5.22–5.10 (m, 1H), 4.60–4.40 (m, 3H), 4.20–4.00 (m,3H), 3.92 (d, 1H), 3.70–5.50 (m, 2H), 3.04 (dt, 1H), 2.70 (dt, 1H), 1.93–1.50 (m, 4H), 1.42 (s, 6H), 1.33 (s, 9H).

Step B: N-[1(R)-[(1,2-Dihydro-1-[2-carboxymethanesulfonyl-spiro[3H-indole-3,4'-piperdin ]]-1'-yl)carbonyl]-2-(phenylmethyloxy)ethyl]-2-amino-2-methylpropanamide To a solution of 0.098 g the intermediate from Step A in 1 mL of dichloromethane was added 1 mL of trifluoroacetic acid and stirred for 30 min. The reaction mixture was evaporated to dryness and triturated with ether to 0.096 g of the product as a white solid.

$^1$H NMR (400 MHz, CD$_3$OD) δ7.40–7.28 (m, 6H), 7.24–7.15 (m, 21/2H), 7.00 (dt, 1H), 6.80 (d, 1/2H), 5.17 (dt, 1H), 4.60–4.45 (m, 2H), 4.22 (d, 2H), 4.14–4.00 (m, 3H), 3.81–3.70 (m, 2H), 3.22 (dt, 1H), 2.83 (dt, 1H), 1.96 (dt, 1/2H), 1.80–1.64 (m, 41/2H), 1.62 (s, 1H), 1.60 (s, 5H).

EXAMPLE 34

Step A: N-[1(R)-[(1,2-Dihydro-1-[2-hydroxyethanesulfonyl-spiro[3H-indole-3,4'-piperdin]]-1'-yl)carbonyl]-2-(phenylmethyloxy)ethyl]-[[(1,1-dimethylethyloxy)carbonyl]propanamide trifluoroacetate To a solution of 0.222 g the intermediate from Step A of Example 32 in 2 mL of 2 mL of anhydrous tetrahydrofuran at RT was added was added 0.48 mL of 2M solution of lithium borohydride in tetrahydrofuran and stirred for 3 h. The reaction mixture was quenched with 0.50 mL of acetone, diluted with 15 mL of water and extracted with CH$_2$Cl$_2$ (2×15 mL). The combined organics were washed with brine(10 mL), dried over MgSO$_4$ and concentrated to give 0.27 g of a white foam. Flash chromatography of the residue over 10 g of silica gel with CH$_2$Cl$_2$-acetone (2:1) as eluent gave 0.129 g of the desired material as a thick oil.

$^1$H NMR (400 MHz, CDCl$_3$) δ7.32–7.20 (m, 6H), 7.20–7.10 (m, 2H), 7.09 (d, 1/2H), 6.98 (t, 1/2H), 6.90 (t, 1/2H), 6.54 (d, 1/2H), 5.17–5.10 (m, 1H), 5.00 (bs, 1H), 4.61–4.39 (m, 3H), 4.10–3.95 (m, 5H), 3.93–3.74 (m, 2H), 3.66 (ddd, 1H), 3.53 (dt, 1H), 3.27 (dt, 2H), 3.00 (dt, 1H), 2.70 (dt, 1H), 1.90–1.50 (m, 4H), 1.43 (s, 4H), 1.41 (s, 2H), 1.36 (s, 9H).

Step B: N-[1(R)-[(1,2-Dihydro-1-[2-hydroxyethanesulfonyl-spiro[3H-indole-3,4'-piperdin]]-1'-yl)carbonyl]-2-(phenylmethoxy)ethyl]-2-amino-2-methylpropanamide trifluoroacetate To a solution of 0.129 g the intermediate from Step A in 1 mL of dichloromethane was added 1 mL of trifluoroacetic acid and stirred for 30 min. The reaction mixture was evaporated to dryness and triturated with ether to 0.113 g of the product as a white solid.

$^1$H NMR (400 MHz, CD$_3$OD) δ7.40–7.25 (m, 6H), 7.25–7.13 (m, 21/2H), 6.98 (dt, 1H), 6.80 (d, 1/2H), 5.20–5.10 (m, 1H), 4.60–4.43 (m, 3H), 4.10–3.90 (m, 5H), 3.81–3.70 (m, 2H), 3.40–3.33 (dt, 2H), 3.20 (dt, 1H), 3.82 (dt, 1H), 2.00–1.63 (m, 4H), 1.61 (s, 1H), 1.58 (s, 5H).

EXAMPLE 35

Step A: N-[1(R)-[(1,2-Dihydro-1-trifluoromethanemethanesulfonyl-spiro [3H-indole-3,4'-piperdin]-1'-yl)carbonyl]-2-(phenylmethyloxy)ethyl]-[[(1,1-dimethylethyloxy)carbonyl]amino]-2-methylpropanamide hydrochloride To a solution of 0.150 g the intermediate from Step B of Example 29 in 5 mL of dichloromethane was added 0.10 mL of N-methylmorpholine and 0.057 mL of trifluoromethanesulfonic anhydride and stirred at 0° C. for 15 min. The reaction mixture was diluted with 5 mL of saturated aqueous sodium bicarbonate solution and extracted with 2×5 mL of dichloromethane. The combined organics were washed with brine (5 mL), dried over MgSO$_4$ and concentrated. Flash chromatography of the residue over 10 g of silica gel with hexane is acetone (3:1) as eluent gave 0.136 g of the desired product.

$^1$H NMR (400 MHz, CDCl$_3$) δ7.40–7.15 (m, 6H), 7.15–6.93 (m, 21/2H), 6.53 (d, 1/2H), 5.20–5.10 (m, 1H), 4.90 (bs, 1H), 4.70–4.60 (m, 3H), 4.15–3.90 (m, 3H), 3.70 (ddd, 1H), 3.60–3.50 (m, 1H), 3.00 (dt, 1H), 2.70 (dt, 1H), 1.93–1.55 (m, 4H), 1.46 (s, 4H), 1.43 (s, 2H), 1.40 (s, 9H).

Step B: N-[1(R)-[(1,2-Dihydro-1-trifluoromethanesulfonyl-spiro[3H-indole-3,4'-piperdin]]-1'-yl)carbonyl]- 2-(phenylmethyloxy)ethyl]-2-amino-2-methylpropanamide hydrochloride To a solution of 0.136 g the above intermediate in 1 mL of dichloromethane was added 1.0 mL of trifluoroacetic acid and maintained at RT for 30 min. The reaction mixture was evaporated to dryness, basified with 10% aqueous sodium carbonate solution (5 mL), and extracted with ethylacetate (2×5 mL). The combined organics were washed with brine (5 mL), dried over potassium carbonate, and concentrated. This material was dissolved in 2 mL of ethyl acetate and 0.20 mL of 4M HCl in EtOAc was added at 0° C. Ether was added and the precipitate was filtered under nitrogen and washed with ether and dried to give 0.94 g of the product as a white solid.

$^1$H NMR (400 MHz, CD$_3$OD) δ7.40–7.15 (m, 6H), 7.15–6.93 (m, 21/2H), 6.53 (d, 1/2H), 5.20–5.10 (m, 1H), 4.90 (bs, 1H), 4.70–4.60 (m, 3H), 4.15–3.90 (m, 3H), 3.70 (ddd, 1H), 3.60–3.50 (m, 1H), 3.00 (dt, 1H), 2.70 (dt, 1H), 1.93–1.55 (m, 4H), 1.46 (s, 4H), 1.43 (s, 2H).

EXAMPLE 36

Step A: N-[1(R)-[(1,2-Dihydro-1-benzenesulfonyl-spiro [3H-indole- 3,4'-piperdin]-1'-yl)carbonyl]-2-(phenylmethyloxy)ethyl]- 2-amino-2-methylpropanamide hydrochloride To a solution of 0.148 g the intermediate from Step B of Example 29 in 3 mL of dichloromethane was added 0.30 mL of N-methylmorpholine and 0.022 mL of benzenesulfonyl chloride and stirred at room temperature for 1 h. The reaction mixture was diluted with 10 mL of dichloromethane and washed with 10 mL of saturated aqueous sodium bicarbonate solution, dried over MgSO$_4$ and concentrated. Flash chromatography of the residue over 10 g of silica gel with hexane-acetone (3:1) as eluent gave 0.190 g of the desired product.

To a solution of 0.190 g the above intermediate in 3 mL of dichloromethane was added 3 mL of trifluoroacetic acid and maintained at RT for 30 min. The reaction mixture was evaporated to dryness, basified with 10% aqueous sodium carbonate solution (5 mL), and extracted with ethylacetate (2×5 mL). The combined organics were washed with brine (5 mL), dried over potassium carbonate, and concentrated. This material was dissolved in 2 mL of ethyl acetate and 0.40 mL of 4M HCl in EtOAc was added at 0° C. Ether was added and the precipitate was filtered under nitogen and washed with ether and dried to give 0.136 g of the product as a white solid.

$^1$H NMR (400 MHz, CD$_3$OD) δ7.82 (d, 2H), 7.67–7.58 (m, 2H), 7.52 (t, 2H), 7.40–7.20 (m, 6H), 7.10–6.90 (m, 11/2H), 6.68 (d, 1/2H), 5.10 (dt, 1H), 4.53 (ABq, 2H), 4.35 (t; 1H), 4.00–3.80 (m, 3H), 3.75–3.65 (m, 2H), 3.10 (dt, 1H), 2,73 (dt, 1H), 1.75 (dt, 1/2H), 1.48 (m, 11/2H), 1.20–1.05 (m, 2H).

EXAMPLE 37

Step A: N-[1(R)-[(1,2-Dihydro-[1-ureidomethyl-spiro[3 H-indole-3,4'-piperdin]-1'-yl)carbonyl]-2-(phenylmethyloxy)ethyl]- 2-amino-2-methylpropanamide trifluoroacetate To a solution of 0.148 g the intermediate from Step B of Example 29 in 5 mL of 1,2-dichloroethane was added 0.10 mL of methylisocyanate and stirred at RT for 1 h. The reaction mixture was evaporated to dryness. Flash chromatography of the residue over 15 g of silica gel with CH$_2$Cl$_2$-acetone (2:1) as eluent gave 0.137 g of the desired product.

This material was treated with 3 mL of dichloromethane and 3 mL of trifluoroacetic acid for 30 min. at RT. The reaction mixture was evaporated to dryness and triturated with ether to give 0.126 g of a pale yellow solid.

$^1$H NMR (400 MHz, CD$_3$OD) δ 7.82(dd, 1H), 7.42–7.35 (m, 5H), 7.30–7.20 (m, 21/2H), 6.75 (d, 1/2H), 5.19 (dt, 1H), 4.60–4.50 (m, 3H), 4.13 (bd, 1H), 3.90–3.68 (m, 4H), 3.25 (t, 1H), 2.90–2.70 (2s, 4H), 1.98 (dt, 1/2H), 1.85–1.65 (m, 31/2H), 1.62 (s, 2H), 1.59 (s, 4H).

EXAMPLE 38

N-[1(R)-[(1,2-Dihydro-1-[1-methoxycarbonyl-1-methyl-ethanesulfonyl-spiro[3H-indole-3,4'-piperdin]-1'-yl)carbonyl]-2-(indol-3-yl)ethyl]-2-amino-2-methylpropanamide trifluoroacetate Step A: 1,2-Dihydro-1-[1-methoxycarbonyl-1-methyl-ethanesulfonyl]-spiro[3H-indole-3,4'-piperdine]

To 5.06 g of 1,2-Dihydro-1-benzyloxycarbonyl-spiro[3H-indole-3,4'-piperdine]hydrochloride in 50 mL of dichloromethane was added 3.0 mL of triethylamine and 3.40 g of di-t-butylcarbonate and stirred at room temperature for 3 h. The reaction mixture evaporated to dryness and diluted with 100 mL of ether and washed with 50 mL of 0.50N aqueous hydrochloric acid, 50 mL of brine, dried over MgSO$_4$ and concentrated. To this crude product in 50 mL of ethanol was added 1 g of 20% palladium hydroxide on carbon and hydrogenated with H$_2$ balloon overnight. To 0.506 g of this compound in 15 mL of dichloromethane at 0° C. was added 0.74 mL of triethylamine and 0.41 mL of carbomethoxymethanesulfonyl chloride and stirred for 1 h. The reaction mixture was diluted with 25 mL of ether and washed with saturated sodium bicarbonate solution (20 mL), dried over MgSO$_4$, and concentrated. Flash chromatography of the residue over 25 g of silica gel with hexane-ethyl acetate 4:1 as eluent gave 1.79 g of the desired material as a thick oil.

Sodium hydride (0.102 g of 60% in mineral oil) was washed with hexanes and then suspended in 5 mL of dry DMF. A solution of 0.158 g of the above intermediate in 1 mL of DMF was added and stirred for 30 min. Methyl iodide (1.85 mmol) was added and stirred for 3 h. The reaction mixture was poured into 15 mL of saturated aqueous ammonium chloride solution and extracted with ether (2×15 mL). The combined organics were washed with water (15 mL), brine (15 mL), dried over MgSO$_4$ and concentrated to give 0.179 g of the desired material.

$^1$H NMR (200 MHz, CDCl$_3$) δ7.32 (d, 1H), 7.20–6.90 (m, 3H), 4.13 (bd, 2H), 2.83 (bt, 2H), 1.85–1.70 (m, 4H), 1.69 (s, 6H), 148 (s, 9H).

Step B: N-[1(R)-[(1,2-Dihydro-[1-methoxycarbonyl- 1-methylethanesulfonyl]-spiro[3H-indole-3,4'-piperdin]- 1'-yl) carbonyl]-2-(indol-3-yl)ethyl]-[[(1,1-dimethylethyloxy) carbonyl]amino]-2-methylpropanamide To a solution of 0.179 g of the intermediate from Step A was added 1 mL of dichloromethane and 1 mL of trifluoroacetic acid and stirred for 30 min. The reaction mixture was evaporated to dryness, basified with 10 mL of 10% aqueous sodium carbonate solution and extracted with 2×10 mL of dichloromethane. The combined organics were washed with brine (10 mL), dried over potassium carbonate, filtered, and concentrated to 0.120 g of the piperidine as a thick oil. To a solution of this compound in 5 mL of dichloromethane was added 0.132 g of the acid intermediate prepared in Example 21 Step B, 0.055 g of HOBT, 0.102 g of EDC and stirred for 18 h. The reaction mixture was diluted with 25 mL of ether and washed with 15 mL of 0.05N HCl, saturated sodium bicarbonate solution (15 mL), dried over MgSO$_4$ and concentrated. Flash chromatography of the residue over 20 g of silica gel with CH$_2$Cl$_2$-acetone (5:1) as eluent gave 0.094 g of the desired product.

$^1$H NMR (CDCl$_3$, 400 MHz) δ8.60 (s, 2/3H), 8.50 (s, 1/3H), 7.70 (d, 2/3H), 7.60 (d, 1/3H), 7.35 (d, 2/3H), 7.30 (d, 1/3H), 7.26–7.00 (m, 5H), 6.90 (t, 11/3H), 6.40 (d, 2/3H), 5.28–5.16 (m, 1H), 5.05 (bs, 1H), 4.41 (bd, 2/3H), 4.32 (bd, 1/3H), 3.78–3.65 (m, 2H), 3.56 (s, 2H), 3.55 (s, 1H), 3.50 (bd, 1H), 3.20 (dt, 1H), 3.15 (ddd, 1H), 2.75 (t, 1H), 2.42 (m, 1H), 1.18 (d, 2H), 1.24 (s, 4H), 1.50 (s, 2H), 1.48 (s, 4H), 1.42 (s, 9H), 1.30–1.18 (m, 1H), 1.10–0.90 (m, 11/3H), 0.03 (dt, 2/3H).

Step C: N-[1(R)-[(1,2-Dihydro-[1-methoxycarbonyl- 1-methylethanesulfonyl]-spiro[3H-indole-3,4'-piperdin]- 1'-yl) carbonyl]-2-(indol-3-yl)ethyl]-2-amino- 2-methylpropanamide trifluoroacetate A solution of 0.094 g of the intermediate from Step C was treated with 1 mL of dichloromethane and 1 mL of trifluoroacetic acid for 30 min., evaporated to dryness and triturated with ether to give 0.082 g of the desired product.

$^1$H NMR (CD$_3$OD, 400 MHz) δ7.70 (d, 2/3H), 7.60 (d, 1/3H), 7.35 (d, 2/3H), 7.30 (d, 1/3H), 7.26–7.00 (m, 5H), 6.90 (t, 11/3H), 6.40 (d, 2/3H), 5.28–5.16 (m, 1H), 5.05 (bs, 1H), 4.41 (bd, 2/3H), 4.32 (bd, 1/3H), 3.78–3.65 (m, 2H), 3.56 (s, 2H), 3.55 (s, 1H), 3.50 (bd, 1H), 3.20 (dt, 1H), 3.15 (ddd, 1H), 2.75 (t, 1H), 2.42 (m, 1H), 1.18 (d, 2H), 1.24 (s, 4H), 1.50 (s, 2H), 1.48 (s, 4H), 1.30–1.18 (m, 1H), 1.10–0.90 (m, 11/3H), 0.03 (dt, 2/3H).

EXAMPLE 39

N-[1(R)-[(1,2-Dihydro-1-methanesulfonylspiro [3H-indole-3,4'-piperdin]-1'-yl)carbonyl]-2-(indol-3-yl)ethyl]-3-amino-3-methylbutanamide hydrochloride Step A: N-[1(R)-[(1,2-Dihydro-1-methanesulfonylspiro[3 H-indole-3,4'-piperdin]-1'-yl)carbonyl]-2-(indol-3-yl) ethyl]- 3-amino-3-methylbutanamide To a suspension of 1.14 g of 1,2-dihydro- 1-methanesulfonylspiro-[3H-indole-3,4'-piperidine]hydrochloride (prepared as described in Step A of Example 18 (method 1)) in 50 mL of dichloromethane was added 0.80 mL of N-methylmorpholine, 1.00 g of N-tBOC-D-tryptophan, 0.80 g of HOBT, and 1.20 g of EDC and stirred at RT for 18 h. The reaction mixture was diluted with 100 mL of ether and washed with 50 mL of 0.05N HCl, 50 mL of saturated sodium bicarbonate solution, dried over MgSO$_4$, and concentrated.

A solution of the above intermediate in 50 mL of ethyl acetate at 0° C. was treated with HCl (g) for 2 min. and then stirred for 1 h. Dry ether (50 mL) was added, and the precipitated solid was collected by filtration. The yield was 1.44 g.

To 0.86 g of the amine hydrochloride in 30 mL of dichloromethane was added, 0.24 mL N-methylmorpholine, 0.36 g of HOBT, 0.56 g of EDC, and stirred overnight. The reaction mixture was diluted with 100 mL of ether, and washed with 0.05N HCl (50 mL), 50 mL of saturated NaHCO$_3$, dried over MgSO$_4$, and concentrated. Flash chromatography of the residue over 20 g of silica gel with CH$_2$Cl$_2$-acetone (5:1) as the eluent gave 0.74 g of the desired product.

To a solution of 0.74 g of the above intermediate in 5 mL of ethyl acetate at 0° C. was bubbled in dry HCl gas for 2 min. and stirred for 30 min. Ether was added to completely precipitate the product. The solid was filtered and washed with ether under nitrogen, and dried to give 0.57 g of the desired product.

$^1$H NMR (CD$_3$OD, 400 MHz) δ7.69 (d, 2/3H), 7.55 (d, 1/3H), 7.37–6.90 (m, 5H), 6.82 (bt, 11/3H), 6.43 (d, 2/3H), 5.31–5.18 (m, 1H), 4.40 (bd, 2/3H), 4.30 (bd, 1/3H), 3.63–3.38 (m, 4H), 3.22–3.05 (m, 2H), 2.83–2.75 (m, 1H), 2.80 (s, 1H), 2.74 (s, 2H), 2.63 (dd, 1H), 2.55–2.43 (m, 2H), 2.20 (bd, 1H), 1.70–1.53 (m, 1H), 1.38 (2H), 1.36 (s, 2H), 1.35 (s, 1H), 1.34 (s, 1H), 1.18 (bd, 1H), 1.20–0.94 (m, 11/3H), 0.03 (dt, 2/3H).

EXAMPLE 40

N-[1(R)-[(1,2-Dihydro-1-methanesulfonylspiro [3H-indole-3,4'-piperdin]-1'-yl)carbonyl]-2-(indol-3-yl)ethyl]-[3-[2(R)-3-dihydroxylpropyl]-amino]-3-methylbutanamide hydrochloride Step A: N-[1(R)-[(1,2-Dihydro-1-methanesulfonylspiro[3 H-indole-3,4'-piperdin]-1'-yl)carbonyl]-2-(indol-3-yl) ethyl]-[3-[2 (R)-3-dihydroxylpropyl]-amino]-3-methylbutanamide hydrochloride To a solution 0.30 g of the compound obtained in Step B of Example 39 in 5 mL of dry methanol was added 1.5 g of anhydrous sodium acetate, 0.30 g (R)-1,2-isoprpylideneglyceraldehyde (*Tetrahedron* 1985, 41, 3117) and stirred for 1 h. A THF solution of sodium cyanoborohydride (8.7 mL of 1M solution) was added and stirred for 18 h. The reaction mixture was diluted with 20 mL of water and extracted with dichloromethane (3×10 mL). The combined organics were washed with saturated sodium bicarbonate solution (10 mL), dried over K$_2$CO$_3$, and concentrated. Flash chromatography of the residue over 10 g of silica gel with CH$_2$Cl$_2$-methanol (98:2) gave 0.146 g of the reductively aminated compound.

$^1$H NMR (CDCl$_3$, 400 MHz) δ8.70–8.40 (m, 2H), 7.63 (d, 2/3H), 7.55 (d, 1/3H), 7.37 (t, 1H), 7.32 (d, 1/3H), 7.28 (d, 2/3H), 7.20–6.95 (m, 41/3H), 6.52 (d, 2/3H), 5.20–5.08 (m, 1H), 4.55–4.24 (m, 3H), 4.10 (t, 2/3H), 4.05 (t, 1/3H), 3.80–3.70 (m, 1H), 3.70–3.50 (m, 4H), 3.30–3.10 (m, 2H), 2.84 (s, 1H), 2.80 (s, 2H), 2.80–2.70 (m, 2H), 2.68–2.45 (m, 1H), 2.37 (s, 2H), 1.70 (t, 2/3H), 1.52 (bd, 1/3H), 1.44 (s, 2H), 1.43 (s, 1H), 1.35 (s, 2H), 1.33 (s, 1H), 1.25 (s, 3H), 1.33 (s, 6H), 1.20–1.05 (m, 2H), 0.90–0.65 (m, 1/3H), 0.30 (dt, 2/3H).

Step B:

A solution of 0.146 g of the above intermediate was stirred in 3 mL of methanol and 0.100 mL of concentrated hydrochloric acid for 30 min. The reaction mixture was evaporated to dryness and the solid was washed with ether and dried to give 0.109 g of the desired material.

$^1$H NMR (400 MHz, CD$_3$OD) δ7.63 (d, 2/3H), 7.55 (d, 1/3H), 7.41 (d, 2/3H), 7.38 (d, 1/3H), 7.32 (d, 1/3H), 7.26 (d, 2/3H), 7.21–7.10 (m, 4H), 7.08–7.00 (m, 21/3H), 6.63 (d, 2/3H), 5.25 (dd, 2/3H), 5.19 (dd, 1/3H), 4.36 (bd, 2/3H), 4.30 (bd, 1/3H), 3.92–3.83 (m, 1H), 3.80–3.50 (m, 6H), 3.28–3.10 (m, 3H), 3.05–2.95 (m, 2H), 2.90 (s, 1H), 2.86 (s, 2H), 2.78–2.55 (m, 4H), 1.83–1.65 (m, 1H), 1.43 (s, 2H), 1.39 (s, 2H), 1.37 (s, 1H), 1.32 (s, 1H), 1.36–1.20 (m, 1H), 0.04–0.18(m, 22/3H), -0.08 (dt, 2/3H).

EXAMPLE 41

N-[1(R)-[(1,2-Dihydro-1-methanesulfonylspiro [3H-indole-3,4'-piperdin]-1'-yl)carbonyl]-2-(indol-3-yl)ethyl]-[3-[2(R)-hydroxylpropyl]amino]-3-methylbutanamide hydrochloride Step A: N-[1(R)-[(1,2-Dihydro-1-methanesulfonylspiro[3 H-indole-3,4'-piperdin]-1'-yl)carbonyl]-2-(indol-3-yl) ethyl]-[3-[2(R)-hydroxylpropyl]-amino]-3-methylbutanamide hydrochloride To 0.26 g of the intermediate from Step B of Example 39 was added 5 mL of dry methanol, 1.5 g of anhydrous sodium acetate, freshly prepared 0.10 g of 2(R)-(tetrahydropyranyl)oxy-propionaldehyde and stirred for 1 h at room temperature. A THF solution of sodium cyanoborohydride (8.5 mL of 1M solution) was added and stirred for 18 h. The reaction mixture was diluted with 10 mL of saturated sodium bicarbonate solution and extracted with dichloromethane (2×15 mL). The combined organics were washed with brine (10 mL), dried over K$_2$CO$_3$, and concentrated. Flash chromatography of the residue over 10 g of silica gel with CH$_2$Cl$_2$-methanol (98:2) as eluent gave 0.219 g of the desired product.

The above material was stirred in 3 mL of dry methanol with 0.10 mL of concentrated hydrochloric acid, evaporated to dryness, and the residue was triturated with ether to give 0.174 g of the title compound as a pale yellow foam.

$^1$H NMR (400 MHz, CD$_3$OD) δ 7.63 (d, 2/3H), 7.55 (d, 1/3H), 7.41 (d, 2/3H), 7.38 (d, 1/3H), 7.32 (d, 1/3H), 7.26 (d, 2/3H), 7.21–7.10 (m, 4H), 7.08–7.00 (m, 21/3H), 6.63 (d, 2/3H), 5.25 (dd, 2/3H), 5.19 (dd, 1/3H), 4.36 (bd, 2/3H), 4.30 (bd, 1/3H), 3.92–3.83 (m, 1H), 3.80–3.50 (m, 4H), 3.28–3.10 (m, 3H), 3.05–2.95 (m, 2H), 2.90 (s, 1H), 2.86 (s, 2H), 2.78–2.55 (m, 4H), 1.83–1.65 (m, 1H), 1.43 (s, 2H), 1.39 (s, 2H), 1.37 (s, 1H), 1.32 (s, 1H), 1.36–1.20 (m, 1H), 1.28 (d, 3H), 0.04–0.18 (m, 22/3H), -0.08 (dt, 2/3H).

EXAMPLE 42

N-[1(R)-[[3-oxospiro[isobenzofuran-1(3H),4'-piperidin]-1'-yl]carbonyl]-2-(phenylmethoxy)ethyl]-2-amino-2-methylpropanamide trifluroracetate Step A:

To 0.165 g of the acid intermediate prepared as described in Step B of Example 19 in 10 mL of CH$_2$Cl$_2$ was added 0.095 g of 3-oxospiro[isobenzofuran-1 (3H),4'-piperidine], 0.067 g of HOBT, and 0.110 g of EDC and stirred at room temperature for 4 h. The reaction mixture was poured into 10 mL of CH$_2$Cl$_2$, and washed with 20% aqueous citric acid (5 mL), saturated sodium bicarbonate solution (5 mL), dried over MgSO$_4$, and concentrated. Flash chromatography of the residue over 10 g of silica gel with hexane-acetone (3:1) as the eluent gave 0.234 g of the coupled product.

To a solution of 0.024 g of the above intermediate in 1 mL of CH$_2$Cl$_2$ was added 1.0 mL of trifluoroacetic acid and maintained at room temperature for 30 min. The volatiles were evaporated and the residue was triturated with ether to give 21 mg of the title compound as a solid.

$^1$H NMR (CD$_3$OD, 400 MHz) a 7.85 (d, 1/2H), 7.80 (d, 1/2H), 7.63 (t, 1/2H), 7.54–7.40 (m, 21/2H), 7.35–7.20 (m, 51/2H), 7.06 (d, 1H), 6.58 (d, 1/2H), 5.25–5.15 (m, 1H), 4.93 (s, 1H), 4.69 (bd, 1H), 4.55–4.40 (m, 2H), 4.14 (bd, 1H), 3.70–3.40 (m, 2H), 3.18–3.10 (m, 1H), 2.13 (dt, 1H), 2.90–2.75 (m, 2H), 2.70–2.50 (m, 2H), 1.47 (s, 1.5H), 1.46 (s, 1.5H), 1.44 (s, 1.5H), 1.43 (s, 1.5H).

EXAMPLE 43

N-[1(R)-[1,2-dihydro-1-methanesulfonylspiro[3H-indole-3,4'-piperidin]- 1'yl)carbonyl]-4-phenylbutyl]-2-amino-2-methylpropanamide hydrochloride Step A: N-[1(R)-[1,2-dihydro-1-methanesulfonylspiro[3H-indole- 3,4'-piperidin]-1'yl)carbonyl]-4-phenylbutyl]-2-amino- 2-methylpropanamide hydrochloride This compound was prepared from 2 (R)-N-t-butoxycarbonyl-5-phenylpetanoic and 1,2-dihydro-1-methanesulfonylspiro[3H-indole-3,4'-piperdine]hydrochloride using chemistry described for the preparation of compound in Example 18.

FAB MS Calc. for C$_{28}$H$_{38}$N$_4$O$_4$S:MW=526.2; found m/e =(m+1) 527.9

EXAMPLE 44

N-[1(R)-[1,2-dihydro-1-methanesulfonylspiro [3H-indole-3,4'-piperidin]1'yl)carbonyl]-2-phenymethylthio)ethyl]-2-amino-2-methylpropanamide trifluoroacetate Step A: N-[1(R)-[1,2-dihydro-1-methanesulfonylspiro[3 H-indole-3,4'-piperidin]1'yl)carbonyl]-2-phenymethylthio)ethyl]- 2-amino-2-methylpropanamide trifluoroacetate This compound was prepared from the commercially available N-t-BOC-S-benzyl-D-cysteine and 1,2-dihydro-1-methanesulfonylspiro[3H-indole-3,4'-piperdine]hydrochloride using chemistry described for the preparation of the compound in Example 18.

FAB MS Calc. for C$_{27}$H$_{36}$N$_4$O$_4$S$_2$: MW=544.7; found m/e =(m+1) 548.5.

EXAMPLE 45

N-[1(R,S)-[1,2-dihydro-1-methanesulfonylspiro [3H-indole-3,4'-piperidin]-1'yl)carbonyl]-2-(2'-pyridomethyloxy)ethyl]-2-amino-2-methylpropanamide trifluoroacetate Step A: N-[1(R,S)-[1,2-dihydro-1-methanesulfonylspiro[3 H-indole-3,4'-piperidin]-1'yl)carbonyl]-2-hydroxyl-carbamic acid 1,1-dimethylethyl ester To a solution of N-t-BOC-(D)-serine (56 mg, 274 mmole) in 2.5 mL of THF at room temperature was added 1,2-dihydro-1-methanesulfonylspiro[3H-indole-3,4'-piperdine] hydrochloride (prepared from Example 18, Step A, 83 mg, 0.274 mmole), triethylamine (45 mL, 0.33 mmole), HOBt (44 mg, 0.33 mmole), and EDC (63 mg, 0.33 mmole). After 3 hours, the mixture was diluted with ethyl acetate and then washed sequentially with water and brine. The organic layer was dried over sodium sulfate, filtered and concentrated. The residue was purified by MPLC (silica gel, 100% ethyl acetate) to give 112 mg (90%) of the title compound.

Step B: N-[1 (R,S)-[1,2-dihydro-1-methanesulfonylspiro [3H-indoles 3,4'-piperidin]-1 'yl)carbonyl]-2-(2'-pyridomethyloxy)ethyl]carbamic acid 1,1-dimethylethyl ester To oil free sodium hydride (prepared from 60% oil dispersion of sodium hydride by washing with hexanes (3×), 9 mg, 0.21 mmole), in 0.3 mL of THF was added 2-picolyl chloride (16 mg, 0.1 mmole) in 0.3 mL of DMF. After 5 minutes, the intermediate obtained from Step A (45 mg, 0.1 mmole) was added to the reaction mixture. The mixture was stirred at room temperature for two hours and then diluted with ether. The ether layer was washed with water (5×), brine and dried over sodium sulfate. After purification (Preparative-TLC, silica gel, 100% ethyl acetate), 16 mg of the title compound was isolated (29%).

$^1$H NMR (400 MHz, CDCl$_3$, mixture of rotamers): 8.53 (m, 1H), 7.77–6.83 (m, 7H), 5.75 (m, 1/2H), 4.98 (m, 2H), 4.67 (m, 2 1/2H), 4.25 (m, 1/2H), 4.10 (m, 1/2H), 3.91–3.67 (m, 4H), 3.17 (m, 1H), 2.91 (s, 3/2H), 2.89 (s, 3/2H), 2.79 (m, 1H), 1.95–1.69 (m, 4H), 1.42 (s, 9/2 H), 1.41 (s, 9/2H).

Step C: N-[1(R,S)-[1,2-dihydro-1-methanesulfonylspiro[3 H-indole-3,4'-piperidin]-1'yl)carbonyl]-2-(2'-pyridomethyloxy)ethyl]- 2-amino-2-methylpropanamide trifluoroacetate A solution of the intermediate obtained from Step B (16 mg, 0.029 mmole) in 0.5 mL trifluoroacetic acid was stirred at room temperature for ½ hour and then concentrated. To a solution of this residue in 1 ml chloroform was added t-butyloxycarbonyl-α-methylalanine (6.5 mg, 0.032 mmole), HOBt (4.3 mg, 0.032 mmole), triethylamine (10 ml, 0.064 mmole), and EDC (6 mg, 0.032 mmole). After 12 hours at room temperature, the mixture was diluted with methylene chloride and then washed with water and brine. The organic layer was dried over sodium sulfate, filtered and concentrated. The residue was purified by Preparative-TLC (silica gel, 100% ethyl acetate). The purified compound was concentrated. To the residue was added trifluoroacetic acid at room temperature. After 1 hour, the mixture was concentrated to give the title compound (5.3 mg).

¹H NMR (400 MHz, CD₃OD, mixture of rotamers): 8.70 (br. s, 1H), 8.30 (m, 1H), 7.84 (m, 1H), 7.77 (m, 1H), 7.36 (m, 1H), 7.24 (m, 1 1/2H), 7.06 (m, 1 1/2H), 5.24 (t, 6Hz, 1H), 4.86 (m, 2H), 4.56 (d, 13 Hz, 1H), 4.08 (m, 1H), 3.95 (m, 4H), 3.36 (m, 1H), 2.97 (s, 3/2H), 2.96 (s, 3/.2H), 2.01–1.78 (m, 4H), 1.63 (s, 3/2H), 1.61 (s, 3/2H), 1.59 (s, 3/2H), 1.58 (s, 3/2H).

EXAMPLE 46

N-[1(R,S)-[1,2-dihydro-1-methanesulfonylspiro
[3H-indole-3,4'-piperidin]-
1'yl)carbonyl]-2-(2'-pyridothio)ethyl]-2-amino-
2-methylpropanamide trifluoroacetate Step A: N-[1(R,S)-[1,2-dihydro-1-methanesulfonylspiro[3 H-indole-3,4'-piperidin]-1'yl)carbonyl]-2-(2'-pyridothio) ethyl]carbamic acid 1,1-dimethylethyl ester To oil free sodium hydride (600 mg, 7.5 mmole) suspension in 20 mL DMF was added N-t-BOC-D-cysteine (1.2 g, 5.4 mmole) in 20 mL DMF at −10° C. The mixture was warmed to room temperature and stirred for addition an hour. A solution of 2-brompyridine (0.514 mL, 5.4 mmole) in 10 mL DMF was added to the reaction mixture. After heating for 20 hours at 80° C. To this reaction mixture was added CuI (1.03 g, 5.4 mmole) and stirred at the same temperature for another 20 hours. The mixture was cooled to room temperature and poured into 0.5N hydrochloric acid and extracted with ether. The ether layer was filter though Celite, dried over sodium sulfate and concentrated. The residue was purified by MPLC (silica gel, methylene chloride/methanol=10/1). To the purified compound (170 mg, 0.57 mmole) in methylene chloride was added 1,2-dihydro-1-methanesulfonylspiro[3H-indole-3,4'-piperdine]hydrochloride (prepared from Example 18, Step A, 172 mg, 0.57 mmole), triethylamine (95 mL, 0.68 mmole), HOBt (92 mg, 0.68 mmole), and EDC (130 mg, 0.68 mmole) and reacted according to the procedure described in Example 45, Step A to give the title compound (310 mg, 99%).

Step B: N-[1(R,S)-[1,2-dihydro-1-methanesulfonylspiro [3H-indole-3,4'-piperidin]-1'yl)carbonyl]-2-(2'-pyridothio)ethyl]- 2-amino-2-methylpropanamide trifluoroacetate Prepared from the intermediate obtained from Step A (290 mg, 0.53 mmole) by the TFA deprotection procedure. This gave the title compound (102 mg).

¹H NMR (400 MHz, CD₃OD, mixture of rotamers): 8.45(dd, 5, 1Hz, 1 H), 7.61 (m, 1H), 7.39–7.05 (m, 6H), 5.27 (m, 1H), 4.52 (t, 12Hz, 2H), 4.01 (m, 3H), 3.80 (m, 1H), 3.45 (m, 1H), 2.98 (s, 3H), 2.90 (m, 1H), 2.10–1.79 (m, 4H), 1.63 (s, 3/2H), 1.60 (s, 3/2H), 1.59 (s, 3/2H), 1.58 (s, 3/2H). FAB-MS: 532.7 (M+1).

EXAMPLE 47

N-[1(R,S)-[1,2-dihydro-1-methanesulfonylspiro
[3H-indole-3,4'-piperidin]-
1'yl)carbonyl]-2-(cyclohexylthio)ethyl]-2-amino-
2-methylpropanamide trifluoroacetate Step A: N-t-Boc-cyclohexylcysteine To a solution of cyclohexylmercaptan (1 mL, 8.18 mmole) and methyl 2-acetamidoacrylate (1.29 g, 9 mmole) in THF was added a catalytic amount of sodium hydride at room temperature. After 7 days, the reaction was concentrated. A solution of the residue in 20 mL 6 N hydrochloric acid was refluxed for 4 hours and cooled to room temperature. The resulting solution was allowed to stand for 12 hours and filtered. The solids were dried under vacuum. To a mixture of this hydrochloric acid salt in 1N sodium hydroxide solution (15 mL) was added di-t-butyl dicarbonate (1.68 g, 7.7 mmole) in 15 mL 1,4-dioxane. After 12 hours, the mixture was poured into 0.5N hydrochloric acid and extracted with ethyl acetate. The organic layer was washed with water, brine and dried over sodium sulfate. After filtration and concentration, the title compound was isolated in 92% yield (2.23 g).

Step B: N-[1(R,S)-[1,2-dihydro-1-methanesulfonylspiro[3 H-indole-3,4'-piperidin]-1'yl)carbonyl]-2-(cyclohexylthio)ethyl]carbamic acid 1,1-dimethylethyl ester Prepared from the intermediate obtained from Step A (303 mg, 1.0 mmole) by the procedure described in Example 45, Step A to give the title compound (420 mg) in 76% yield.

Step C: N-[1(R,S)-[1,2-dihydro-1-methanesulfonylspiro[3 H-indole-3,4'-piperidin]-1'yl)carbonyl]-2-(cyclohexylthio)ethyl]- 2-[[(1,1-dimethylethyloxy)carbonyl]amino]-2-methylpropanamide A solution of the intermediate obtained from Step B (420 mg, 0.76 mmole) in 5 mL trifluoroacetic acid was stirred at room temperature for 1/2 hour and then concentrated and dried. To a solution of this residue in 10 mL chloroform was added t-butyloxycarbonyl-α-methylalanine (170 mg, 0.84 mmole), HOBt (113 mg, 0.84 mmole), triethylamine (116 mL, 0.84 mmole), and EDC (160 mg, 0.84 mmole). After 12 hours at room temperature, the mixture was diluted with methylene chloride and washed with water and brine. The organic layer was dried over sodium sulfate, filtered and concentrated. The residue was purified by MPLC (silica gel, hexanes/ethyl acetate=1/1) to give the title compound (430 mg) in 89%.

Step D: N-[1(R,S)-[1,2-dihydro-1-methanesulfonylspiro[3 H-indole-3,4'-piperidin]-1'yl)carbonyl]-2-(cyclohexylthio)ethyl]- 2-amino-2-methylpropanamide trifluoroacetate A solution of the intermediate obtained from Step C (35 mg, 0.055 mmole) in 0.5 mL trifluoroacetic acid was stirred at room temperature for ½ hour and then concentrated to give the title compound (33 mg).

¹H NMR (400 MHz, CD₃OD, mixture of rotamers): 7.38 (d, 8Hz, 1H), 7.25–7.17 (m, 2H), 7.06 (m, 1H), 5.02 (m, 1H), 4.52 (m, 1H), 4.11 (m, 1H), 3.97 (m, 2H), 3.39 (m, 1H), 3.02 (m, 1H), 2.98 (s, 3H), 2.90–2.71 (m, 3H), 2.05–1.74 (m, 9H), 1.62 (s, 3/2H), 1.61 (s, 3/2H), 1.60 (s, 3/2H), 1.57 (s, 3/2H), 1.32 (m, 5H). FAB-MS: 537.9 (M+1).

EXAMPLE 48

N-[1(R,S)-[1,2-dihydro-1-methanesulfonylspiro
[3H-indole-3,4'-piperidin]- 1'yl)carbonyl]-
2-(cyclohexylsulfinyl)ethyl]-2-amino-2-
methylpropanamide hydrochloride To a solution of the intermediate obtained from Example 47, Step C (35 mg, 0.055 mole) in 1 mL methanol was added sodium periodate in 1 mL water at room temperature. After a couple of hours, the reaction mixture was diluted with ethyl acetate and washed with aqueous sodium sulfite solution. The organic layer was dried over sodium sulfate, filtered and concentrated. Deprotection of the residue by the trifluoroacetic acid procedure (Example 47, Step D) gave the crude product, which was purified by Preparative-TLC (silica gel, methylene chloride/methanol/ammonium hydroxide=10/1/0.1). The purified product was re-acidified with HCl in ether to give the title compound (21 mg).

¹H NMR (400 MHz, CD₃OD, mixture of diastereomers and rotamers): 7.38 –7.04 (m, 4H), 5.43 (m, 1H), 4.50 (m, 1H), 4.05 (m, 1H), 3.96 (m, 2H), 3.38 (m, 1H), 3.13 (m, 1H), 2.98 (s, 3H), 2.90–2.71 (m, 3H), 2.05–1.74 (m, 9H), 1.62 (m, 6H), 1.51–1.32 (m, 5H). FAB-MS: 553.9 (M+1).

EXAMPLE 49

N-[1(R,S)-[1,2-dihydro-1-methanesulfonylspiro
[3H-indole-3,4'-piperidin]-
1'yl)carbonyl]-2-(cyclohexylsulfonyl)ethyl]-2-amino-
2-methylpropanamide hydrochloride To a solution of the intermediate obtained from Example 47, Step C (35 mg, 0.055 mmole) in 1 mL methanol was added OXONE in 1 mL water at room temperature. After a couple of hours, the reaction mixture was diluted with ethyl acetate and washed with aqueous sodium sulfite solution. The organic layer was dried over sodium sulfate, filtered and concentrated. To the residue was added trifluoroacetic acid by the procedure described in Example 47, Step D to give a crude product, which was purified by preparative-TLC(silica gel, methylene chloride/methanol/ammonium hydroxide= 10/1/0.1). The is purified product was re-acidified with HCl in ether to give the title compound (12 mg).

¹H NMR (400 MHz, CD₃OD, mixture of rotamers): 7.36 (dd, 7, 2Hz, 1H), 7.22 (m, 2H), 7.06 (m, 1H), 5.53 (m, 1H), 4.51 (m, 1H), 4.11 (m, 1H), 3.95 (m, 2H), 3.49 (m, 2H), 3.38 (m, 1H), 3.10 (m, 1H), 2.98 (s, 3/2H), 2.97 (s, 3/2H), 2.91 (m, 1H), 2.20–1.74 (m, 9H), 1.62 (s, 3/2H), 1.61 (s, 3/2H), 1.58 (s, 3/2H), 1.57 (s, 3/2H), 1.51–1.32 (m, 5H). FAB-MS: 569.9 (M+1).

EXAMPLE 50

N-[1(R)-[spiro[benzo[b]thiophene-3(2H),4'-piperidine]-
1'-yl carbonyl-
2-indole-3-yl)ethyl-2-amino-2-methylpropanamide
hydrochloride Step A: 1-[(1,1-dimethylethoxy)carbonyl]-3-hydroxy-4-methylene- 1,2,5,6-tetrahydropyridine To a suspension/solution of methyltriphenylphosphonium iodide (30 g, 74 mmole) in 150 mL of THF was slowly added butyllithium (2.5N, 25.5 mL, 63.7 mmoles) at 0° C. After stirring an hour at room temperature, N-t-BOC protected 4-piperidone (prepared from 4-piperidone monohydrate hydrochloride by the procedure described in Protective Groups in Organic Synthesis T. W. Greene, John Wiley and Sons, N.Y. 1981.) in 50 mL of THF was added to reaction mixture at room temperature slowly. This reaction was stirred for 2 hours and filtered. The filtrate was concentrated and purified (MPLC, silica gel, hexanes/ethyl acetate=10/1) to give the Wittig product (7.9 g) in 82% yield.

To a suspension of selenium dioxide/silica gel (prepared according to the procedure described in *Chem. lett.* 1981, 1703) in 30 mL methylene chloride was added t-butyl hydroperoxide (1.23 mL). After 15 minutes, the Wittig product (0.72 g, 3.69 mmole) in 5 mL of methylene chloride was added. The cloudy solution was stirred for 3 hours and filtered though Celite. The filtrate was washed with water, brine and dried over sodium sulfate. The organic layer was concentrated and purified by flash chromatography (hexanes/ethyl acetate=4/1) to give the title compound in 52% yield (0.41 g).

Step B: 1-[(1,1-dimethylethoxy)carbonyl]-4-chloromethyl-1,2,5,6-tetrahydropyridine The intermediate obtained from Step A (400 mg, 1.88 mmole) was dissolved in 10 mL benzene and thionyl chloride (165 ml, 2.26 mmole) was added and heated to 60° C. for 25 minutes. The resulting mixture was poured into NaHCO₃ (aq.) and extracted with ether. The ether layer was dried over magnesium sulfate and concentrated to give title compound (333 mg, 77%).

Step C: 1-[(1,1-dimethylethoxy)carbonyl]-4-[[(2-bromophenyl)thio]methyl-1,2,5,6-tetrahydropyridine The intermediate obtained from Step B (330 mg, 1.43 mmole) was dissolved in 10 mL of acetone and 2-bromothiophenol (172 ml, 1.43 mmole) and potassium carbonate (390 mg, 2.86 mmole) were added. The reaction mixture was heated to 60° C. for an hour and then filtered though silica gel (100% ether). The organic layer was concentrated and purified by flash chromatography (silica gel, hexanes/ ethyl acetate=10/1) to give the title compound in 84% yield (460 mg).

Step D: 1'-[(1,1-dimethylethoxy)carbonyl]-spiro[benzo[b]thiophene-3-(2H),y'-piperdine The intermediate obtained from Step C (450 mg, 1.17 mmole) was dissolved in 60 mL of benzene and AIBN (10 mg) and tributyltin hydride (644 mL, 2.39 mmole) were added. This mixture was refluxed for 2 hours and concentrated. The residue was dissolved in ether and bromine was added till the reaction solution turned to a brownish color. To this brownish solution at room temperature was added DBU (650 mL) in dropwise manner. The resulting cloudy solution was filtered though silical gel and washed with ether. The ether solution was concentrated and the residue was purified by radial chromatography (silic gel, hexanes/ethyl acetate= 10/1) to give title compound (157 mg) in 43% yield.

Step E: N-[1(1R)-[spiro[benzo[b]thiophene-3(2H), y'-piperdine]- 1'-yl)carbonyl]-2-(indole-3-yl)ethyl]-2-amino-2-methylpropanamide hydrochloride A solution of the intermediate obtained from Step D (50 mg, 0.164 mmole) in 0.5 mL of TFA was stirred at room temperature for ½ hour and then concentrated. The residue was diluted with chloroform and washed with NaHCO₃ (aq.). The organic layer was dried over sodium sulfate, filtered and concentrated to give free amine (32 mg) in 95%. A solution of free amine (5.1 mg, 0.025 mmole) in 1 ml chloroform was added the intermediate obtained from Example 21 Step C (9.2 mg, 0.0246 mmole), HOBt (4.0 mg, 0.0295 mmole) and EDC (5.6 mg, 0.0295 mmole) at room temperature. After 12 hours, the reaction was poured into water and extracted with chloroform. The chloroform layer was dried over sodium sulfate, filtered and concentrated. The residue was purified by Preparative-TLC (silica gel. hexanes/ethyl acetate=1/1) to give a colorless foam (13 mg, 94%). The title compound was obtained from this colorless foam according to the procedure described in Example 18, Step C.

¹H NMR (400 MHz, CD₃OD) mixture of rotamers: δ7.62 (d, 8Hz, 2/3H), 7.54 (d, 8Hz, 1/3H), 7.39 (d, 8Hz, 2/3H), 7.35 (d, 8Hz, 1/3H), 7.19–7.00 (m, 6 1/3H), 2.62 (m, 1H), 1.72–1.65 (m, 2 1/3H), 1.61 (s, 4H), 1.50 (s, 2H), 0.94 (m, 1H), 0.10 (m, 2/3H). FAB-MS 477 (m+1).

EXAMPLE 51

Step A: 1',2-Dimethylspiro[isoindolin-1-one-3,4'-piperidine]

To a stirred solution of 2-methylisoindolin-1-one (1.47 g, 10 mmol, available from Aldrich chemical company) and mechlorethamine hydrochloride (2.9 g, 15 mmol) in DMF (50 mL) at 0° under Ar, was slowly added potassium hydride (35% in mineral oil, 4.5 g, 40 mmol). The reaction mixture was then slowly warmed to room temperature and stirred for additional 3 hours. TLC (60% ethyl acetate in hexane) showed reaction was complete. The mixture was slowly poured on to ice, and it was extracted with ethyl acetate six times. The combined organic extracts were dried ($Na_2SO_4$) and evaporated. The residue was purified by flash chromatography eluting with a solvent gradient of 5–10% methanol in dichloromethane to provide 1.17 g of product.

$^1$H NMR (400 MHz, $CDCl_3$): δ7.85 (dd, J=1.5Hz, 6.5Hz, 1H), 7.81 (d, J=7.1Hz, 1H), 7.50–7.40 (m, 2H), 3.03 (s, 3H), 2.95–2.90 (m, 2H), 2.71 (dt, J=2.6Hz, 11.4Hz, 2H), 2.46(s, 3H), 2.31 (dt, J=4.7Hz, 13 Hz, 2H), 1.44 (dd, J=1.6Hz, 13Hz, 2H). FAB-MS calc. for $C_{14}H_{18}N_2O$, 230; found 231 (M+H).

Step B: 2-Methylspiro[isoindolin-1-one-3,4'-piperidine]

The demethylation procedure was according to Tidwell and Buchwald, J. Org. Chem. 1992, 57, 6380–6382. To a stirred solution of the product from Step A (1.0 g, 4.35 mmol) in 1,2-dichloroethane (10 mL) at 0° was added 1-chloroethyl chloroformate (0.56 mL, 5.2 mmol) and the mixture was stirred for 20 min. Methanol (10 mL) was added and the resulting mixture was refluxed for one hour. Evaporation and flash column purification eluting with 10–20% $NH_4OH$-MeOH(1:10) in chloroform yielded 0.63 g of product.

$^1$H NMR (400 MHz, $CD_3OD$): δ8.02 (d, J=8Hz, 1H), 7.85 (d, J=8Hz, 1H), 7.70 (t, J=8Hz, 1H), 7.60 (t, J=8Hz, 1H), 3.75–3.60 (m, 4H), 3.10 (s, 3H), 2.60–2.51 (m, 2H), 1.72 (br. d, J=14Hz, 2H). EI MS calc. for $Cl_3H_{16}N_{20}$, 216; found 301 ($M^+$, 5%), 216 ($M^+$), 185, 160.

Step C: 2-Methylspiro[isoindolin-1-one-3,4'-piperidine]-1'-carboxylic acid, 1,1-dimethylethyl ester To a stirred solution of 2-methylisoindolin-1-one (100 mg) in DMF (2 mL) was added excess KH in mineral oil at 0° under Ar. After 5 min., bis(2-bromoethyl)t-butyl carbamate (300 mg) was added and the mixture was stirred at room temperature for 1 h and heated at 80° overnight. The mixture was poured on to ice, and it was extracted with ethyl acetate. The organic extract was dried ($Na_2SO_4$) and evaporated. The residue was purified by prep-TLC eluting with 60% ethyl acetate in hexane to provide 16 mg of product.

$^1$H NMR (400 MHz, $CDCl_3$): δ7.89 (dd, J=1.3Hz, 5.8Hz, 1H), 7.75 (d, J=6.5Hz, 1H), 7.54–7.40 (m, 2H), 4.35–4.10 (br. m, 2H), 3.02 (s, 3H), 2.14 (dt, J=5.3Hz, 13Hz, 2H), 1.49 (s, 9H), 1.46–1.40 (m, 2H). FAB-MS calc. for $C_{18}H_{24}N_{3O3}$, 316; found 317 (M+H, 100%).

Step D: 2-Methylspiro[isoindolin-1-one-3,4'-piperidine]

The intermediate from Step C (16 mg) was treated with concentrated HCl and MeOH at room temperature for 2 hours and evaporated to yield the desired product.

All spectral data for this compound is the same as in step B.

Step E: N-[1(R)-[(2-Methylspiro[isoindolin-1-one-3,4'-piperidin]- 1'-yl)carbonyl]-2-(indol-3-yl)ethyl ]-2-[[( 1,1-dimethylethyloxy)carbonyl]amino]-2-methylpropanamide The compound was prepared according to standard peptide coupling technology from α(R)-[[2-[[(1,1-dimethylethoxy)carbonyl]amino]- 2,2-dimethyl-1-oxoethyl]amino]-1H-indole-3-propanoic acid (25 mg) and the product from Step B $^1$H NMR (400 MHz, $CDCl_3$): δ8.58, 8.44 (2 br. s, 1H), 7.80–7.15, 6.44 (m, d, J=7.6Hz, total 10H), 5.43–5.36, 5.22–5.15, (2m, 1H), 4.98 (br. s, 1H), 4.60–4.50 (br. m, 1H), 3.64–3.50 (br. m, 1H), 3.40–3.05, 2.72–2.64, (2m, 4H), 2.88, 2.51 (2s, 3H), 2.00–1.90 (m, 2H), 1.52, 1.51 (2s, 3H), 1.49 (s, 3H), 1.45, 1.44 (2s, 9H), 1.40–0.40 (several m, 2H). FAB-MS calc. for $C_{33}H_{41}N_5O_5$, 587; found 588 (M+H), 532, 488.

Step F: N-[1(R)-[(2-Methylspiro[isoindolin-1-one-3,4'-piperidin]- 1'-yl)carbonyl]-2-(indol-3-yl)ethyl]-2-amino-2-methylpropanamide hydrochloride The title compound was prepared using HCl in ethyl acetate from the product of Step E.

$^1$H NMR (400 MHz, $CD_3OD$): δ7.84–6.89 (m, 9H), 5.30, 5.15 (2 dd, 1H), 4.50–4.40 (m, 1H), 3.85–3.77 (m, 1H), 3.65–3.50 (m), 3.40–3.15 (m), 2.95, 2.58 (2s, 3H), 2.95–2.85 (m), 2.55–2.47 (m), 2.22–2.15 (m), 2.09–2.00 (m), 1.65, 1.64, 1.60 (3s, 6H), 1.50–1.20 (m), 1.15–1.05 (m), 0.9–0.8 (m), 0.61–0.52 (m). FAB-MS calc. for $C_{28}H_{33}N_5O_3$, 471; found 472 (M+H).

EXAMPLE 52

N-[1(R)-[[1-[[[[[6-[[[4-azido-2-hydroxy-5-iodophenyl] carbonyl]amino]hexyl]amino]carbonyl]methyl] sulfonyl]- 2,3-dihydrospiro[3H-indole-3,4'-piperidin]-1'-yl] carbonyl]-2-(phenylmethyloxy)ethyl]- 2-amino-2-methylpropanamide hydrochloride.

To a solution of the commercially available N-hydroxysuccimidyl-4-azido-2-hydroxy-benzoate in 5 mL of $CH_2Cl_2$ was added 6-N-t-butoxycarbonyl-n-hexylamine hydrochloride and 0.10 mL of Hunig's base and stirred for 4 h. The reaction mixture was evaporated to dryness and chromatorgraphed on 15 g of silica gel. Elution with hexanes-ethyl acetate (2:1) gave 0.229 of the acylated product. To 29 mg of the above material was added 2 ml of THF and 2 mL of 0.01M aqueous NaOH, 25 mg of potassium iodide. Chloramine-T (15 mg) was added and stirred for 30 min. The reaction was quenched with 2 mL of saturated sodium thiosulfate solution, diluted with 5 mL of 0.05N HCl and extracted with ethyl acetate (2×5 mL). The combined organics were washed with brine (5 mL), dried over $MgSO_4$ and concentrated. Flash chromatography of the residue (5 g silica gel) with hexane-ether (3:1) gave 26 mg of the iodonated material. Deprotection of the N-tBOC was carried out with 4M HCl in ethyl acetate to give 21.4 mg of the hydrochloride.

To solution of this material in 5 mL of $CH_2Cl_2$ was added 49 mg of the acid intermediate form Step A of Example 33, 0.016 mL of NMM, 19.8 mg of HOBT, and 29 mg of EDC and stirred for 18 h. The reaction was worked up and purified in the usual manner.

Once again deprotection of the N-tBOC group was carried with 4M HCl in ethyl acetate. This gave the title compound as a yellow-brown solid. This material was basified by dissolving in 2 mL of saturated $NaHCO_3$ and extracted with $CH_2Cl_2$ (2×3 mL). The combined organics were dried over $Na2SO_4$ and concentrated to the title compound.

$^1$H NMR ($CDCl_3$, 400 MHz) The compound exists as a 3:2 mixture of rotamers. δ8.40–8.20 (m, 1H), 7.95 (s, 2/3H), 7.90 (s, 1/3H), 7.40–6.90 (m, 9 1/3H), 6.70 (s, 2/3H), 6.55 (m, 1H), 5.20–5.10 (m, 1H), 4.70–4.40 (m, 4H), 4.10–3.80 (m, 5H), 3.80–3.50 (m, 4H), 3.40–3.10 (m, 4H), 3.10–3.00 (m, 1H), 2.70 (dt, 1H), 1.90–1.20 (m, 14H), 1.30 (s, 6H).

EXAMPLE 53

N-[1(S)-[(1,2-dihydro-1-methylsulfonylspiro [3H-indole-3,4'-piperidin]- 1'-yl)carbonyl]-2-(phenylmethylsulfonyl)ethyl]- 2-amino-2-methylpropanamide hydrochloride Step A: N-[1(S)-[(1,2-Dihydro-1-methylsulfonylspiro[3H-indole- 3,4'-piperidin]-1'yl)carbonyl]-2-(phenylmethylsulfonyl)ethyl]2-amino-2-methylpropanamide A sample of N-[1(S)-[(1,2-dihydro-1-methylsulfonylspiro [3H-indole-3,4'-piperidin ]-1'yl)carbonyl]-2-(phenylmethylthio)ethyl]2-[[1,1-dimethylethyloxy)carbonyl]amino]-2-methylpropanamide (Example 44, Step C), 72 mg, was dissolved in 0.5 mL methanol and cooled in an ice bath. To this was added, dropwise, with stirring, a solution of 101 mg OXONE (TM) in 0.5 mL water. The reaction was monitored over several hours by TLC on silica gel GF plates, developed with 2:1 EtOAc: hexane; two more polar spots were observed to grow over time at the expense of the starting material. When the starting material was essentially gone, the reaction mixture was taken to near dryness under a nitrogen stream, and the residue extracted with chloroform. The $MgSO_4$ dried extract was subjected to preparative TLC on an 8"×8"×1,000μ silica gel GF plate, developed with EtOAc: hexane; two bands were isolated. The less polar component was dissolved in 0.5 mL of anisole, cooled in an ice-bath, and treated with 0.5 mL of TFA. The reaction was stoppered and removed from the bath. After 30 minutes, the bulk of the TFA was removed under aspirator vacuum, and the bulk of the remaining anisole evaporated under a nitrogen stream. The residue was taken up in chloroform and shaken with 1M $K_2HPO_4$, to which enough NaOH was added to give a pH>9. The chloroform was then removed and the aqueous phase extracted several more times with chloroform, the combined organic phases dried with $MgSO_4$, and concentrated under reduced pressure to a gum. Preparative TLC on a silica gel GF plate with 0.5:5:95 Conc. $NH_4OH:MeOH:CHCl_3$ afforded the free base of the title compound. Calc. for $C_{27}H_{36}N_4O_6S_2$: MW=576.7; found m/e=(m+1) 577.5.

Step B: N-[1(S)-[(1,2-Dihydro-1-methylsulfonylspiro [3H-indole- 3,4'-piperidin]-1'yl)carbonyl]-2-(phenylmethylsulfonyl)ethyl]- 2-amino-2-methylpropanamide hydrochloride The hydrochloride salt of the compound from Step A above was produced using standard procedures described above affording the title compound.

EXAMPLE 54

Preparation of the two N-[1(S)-[(1,2-dihydro-1-methylsulfonylspiro-[3H-indole-3,4'-piperidin]-1'-yl)carbonyl]-2-(phenylmethylsulfinyl) ethyl]- 2-amino-2-methylpropanamide hydrochlorides Step A: N-[1(S)-[(1,2-Dihydro-1-methylsulfonylspiro[3H-indole- 3,4'-piperidin ]-1'yl)carbonyl]-2-(phenylmethylsulfinyl)ethyl]- 2-amino-2-methylpropanamide Subjecting the more polar band from Step A, Example 53, to the TFA/anisole deblocking procedure described there, followed by the same preparative TLC workup, two bands are isolated, corresponding to the two diastereomeric sulfoxides expected. For the less polar diastereomer: Calc. for $C_{27}H_{36}N_4O_5S_2$: MW=560.7; found m/e =(m+1 ) 561.7.

For the more polar diastereomer: Calc. for $C_{27}H_{36}N_4O_5S_2$: MW=560.7; found m/e=(m+1) 561.7.

Step B: N-[1(S)-[(1,2-Dihydro-1-methylsulfonylspiro[3H-indole- 3,4'-piperidin]-1'yl)carbonyl]-2-(phenylmethylsulfinyl)ethyl]- 2-amino-2-methylpropanamide hydrochloride The title compound is obtained by substituting either of the compounds isolated from Step A above for the compound prepared in Step A, Example 53 for Step B, Example 53.

EXAMPLE 55

N-[1(R)-[(1,2-Dihydro-1-methanesulfonylspiro [3H-indole-3,4 '-piperdin]-1'-yl)carbonyl]-2-(phenylmethyloxy) ethyl]-2-amino-2-methylpropanamide mesylate This compound was prepared by the treating the free base obtained in Example 18, Step C, with methane sulfonic acid. The title compound was obtained by recrystallizing it from ethyl acetate-ethanol-water. m.p.=166°–168° C.

EXAMPLE 56

2,3,3a,4,6,6a-hexahydro-2-oxo-1H-thieno[3,4-d]imidazole-4-(S)-pentanoic acid-6-[[[[[1'-[[(29R)-[[2-amino-2-methyl-1-oxopropyl]amino]-3-(phenylmethyloxy)-1-oxopropyl]-2,3-dihydrospiro[3H-indole-3,4'-piperidin]-1'yl] sulfonyl]methyl]carbonyl]amino]hexyl ester trifluoroacetate To a solution of 0.108 g of the intermediate prepared in Example 33 step A in 5 mL of $CH_2Cl_2$ was added 20 mg of 6-amino-hexanol, 28 mg of HOBT, and 42 mg of EDC and stirred for 4 h. the reaction mixture was diluted with 10 mL of $CH_2Cl_2$ and washed with 0.5N HCl (5 mL), satureated aqueous $NaHCO_3$ (5 mL), dried over $MgSO_4$ and concentrated. The residue was purified by flash chromatography (10 g silica gel) with $CH_2Cl_2$-acetone (1:1) as eluent.

To 56.2 mg of the above intermediate in 2 mL of $CH_2Cl_2$ and 2 mL of DMF was added 23 mg of biotin, 14 mg of DMAP, 28 mg of EDC and stirred for 18 h. The reaction was worked up in the ususal manner. Purification of the residue by flash chromatography over 5 g of silica gel with $CH_2Cl_2$-acetone (1:1) as the eluent gave 22 mg of the biotin conjugate. Deprotection of the N-tBOC was carried out in $CH_2Cl_2$-TFA to give 18.9 mg of the title compound as a white solid.

$^1$H NMR (CDCl$_3$, 400 MHz) The compound is a 3:2 mixture of rotamers. d 8.45–8.23 (m, 1H), 7.9 (s, 1H), 7.40–7.28 (m, 4H), 7.25–7.17 (m, 2H), 7.00 (dt, 2/3H), 6.80 (d, 1/3H), 5.21–5.14 (m, 1H), 4.60–4.42 (m, 4H), 4.28 (bt, 1H), 4.15–4.00 (m, 6H), 3.85–3.70 (m, 2H), 3.20–3.10 (m, 3H), 2.90 (dd, 1H), 2.83 (dt, 1H), 2.70 (d, 1H), 2.40–2.25 (m, 2H), 2.00–0.60 (m, 18H), 1.62 (s, 3H), 1.60 (s, 3H).

What is claimed is:

1. A compound of the formula

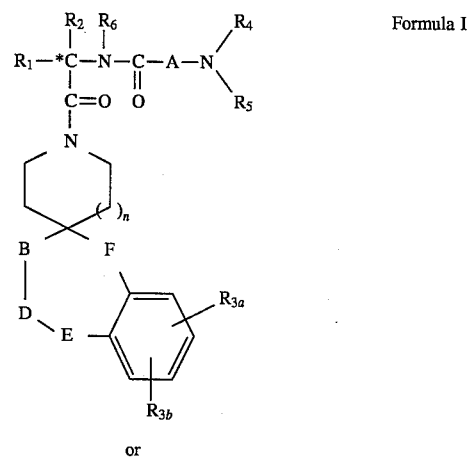

Formula I or

-continued

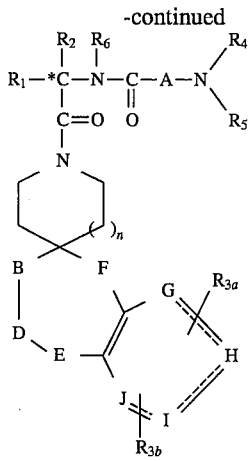

Formula II wherein:

R₁ is selected from the group consisting of:

$C_1$–$C_{10}$ alkyl, -aryl, aryl-($C_1$–$C_6$ alkyl)-, $C_3$–$C_7$ cycloalkyl-($C_1$–$C_6$alkyl)-, $C_1$–$C_5$alkyl-K—$C_1$–$C_5$ alkyl-, aryl($C_0$–$C_5$alkyl)-K—($C_1$–$C_5$ alkyl)-, and $C_3$–$C_7$ cycloalkyl($C_0$–$C_5$ alkyl)-K—($C_1$–$C_5$ alkyl)-, wherein K is —O—, —S(O)$_m$—, —N(R₂)C(O)—, —C(O)N(R₂)—, —OC(O)—, —C(O)O—, or —CR₂=CR₂—, or —C≡C—, where the R₂ and alkyl groups may be futher substituted by 1 to 9 halogen, S(O)mR$_{2a}$, 1 to 3 OR$_{2a}$ or C(O)OR$_{2a}$, and where the aryl groups may be further substituted by phenyl, phenoxy, halophenyl, 1 to 3 $C_1$–$C_6$ alkyl, 1 to 3 halogen, 1 to 2—OR₂, methylenedioxy, —S(O)$_m$R₂, 1 to 2 —CF₃, —OCF₃, nitro, —N(R₂)(R₂), —N(R₂)C(O)R₂, —C(O)OR₂, —C(O)N(R₂)(R₂), —SO₂N(R₂)(R₂), —N(R₂)S(O)₂ aryl, or —N(R₂)SO₂R₂;

R₂ is selected from the group consisting of:

hydrogen, $C_1$–$C_6$ alkyl, $C_3$–$C_7$ cycloalkyl, and, where two $C_1$–$C_6$ alkyl groups are present on one atom, they may be optionally joined to form a $C_3$–$C_8$ cyclic ring optionally including oxygen, sulfur, or NR$_{2a}$;

R$_{2a}$ is hydrogen or $C_1$–$C_6$ alkyl;

R$_{3a}$ and R$_{3b}$ are independently selected from the group consisting of:

hydrogen, halogen, $C_1$–$C_6$ alkyl, —OR₂, cyano, —OCF₃, methylenedioxy, nitro, —S(O)$_m$R₂, —CF₃ and —C(O)OR₂, and when R$_{3a}$ and R$_{3b}$ are in an ortho arrangement, they may be joined to form a $C_5$ to $C_8$ aliphatic or aromatic ring optionally including 1 or 2 heteroatoms selected from oxygen, sulfur, or nitrogen;

R₄ and R₅ are independently selected from the group consisting of:

hydrogen, $C_1$–$C_6$ alkyl, and substituted $C_1$–$C_6$ alkyl where the substituents on alkyl are 1 to 5 halo, 1 to 3 hydroxy, 1 to 3 $C_1$–$C_{10}$ alkanoyloxy, 1 to 3 $C_1$–$C_6$ alkoxy, phenyl, phenoxy, 2-furyl, $C_1$–$C_6$ alkoxycarbonyl, or S(O)$_m$($C_1$–$C_6$ alkyl); or R₄ and R₅ may be taken together to form —(CH₂)$_r$L$_a$(CH₂)$_s$—, where L$_a$ is —C(R₂)₂—, —O—, —S(O)$_m$—, or —N(R₂)—, where r and s are independently 1, 2 or 3;

R₆ is hydrogen or $C_1$–$C_6$ alkyl;

A is:

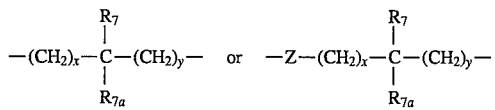

wherein x and y are independently 0, 1, 2, or 3; Z is N—R₂ or O;

R₇ and R$_{7a}$ are independently selected from the group consisting of:

hydrogen, —$C_1$–$C_6$ alkyl, —OR₂, trifluoromethyl, phenyl, substituted $C_1$–$C_6$ alkyl where the substituents are selected from imidazolyl, phenyl, indolyl, p-hydroxyphenyl,—OR₂, 1 to 3 fluoro, —S(O)$_m$R₂, —C(O)OR₂, —$C_3$–$C_7$ cycloalkyl, —N(R₂)(R₂), and —C(O)N(R₂)(R₂); or R₇ and R$_{7a}$ may independently be joined to one or both of the R₄ and R₅ groups to form an alkylene bridge between the terminal nitrogen and the alkyl portion of the R₇ or R$_{7a}$ groups, wherein the bridge contains 1 to 5 carbons atoms;

B, D, E, and F are independently selected from the group consisting of: —C(R₈)(R₁₀)—, —O—, C=O, —S(O)$_m$—, and —NR₉—, wherein one or two of B, D, E, or F may be optionally absent to provide a 5, 6, or 7 membered ring, provided that one of B, D, E or F is —O—,—S(O)$_m$—, or —NR₉—, and at least one of the remaining B, D, E or F is —C(R₈)(R₁₀)— or C=O; or B and D taken together may be —N=CR₁₀— or —CR₁₀=N—, if E or F is —O—,—S(O)$_m$—, or—NR₉—, or D and E taken together may be —N=CR₁₀— or —CR₁₀=N—, if B or F is —O—, —S(O)$_m$—, or —NR₉—, or B and D taken together may be —CR₈=CR₁₀—, if E or F is —O—, —S(O)$_m$—, or —NR₉—, or D and E taken together may be —CR₈=CR₁₀—, if B or F is —O—, —S(O)$_m$—, or —NR₉—;

R₈ and R 10 are independently selected from the group consisting of:

hydrogen, —R₂, —OR₂, —(CH₂)$_q$-aryl, —(CH₂)$_q$—C(O)OR₂, —(CH₂)$_q$—C(O)O(CH₂)$_q$-aryl, and —(CH₂)$_q$-(1H-tetrazol-5-yl), where the aryl is optionally substituted by 1 to 3 halo, 1 to 2 $C_1$–$C_8$ alkyl, 1 to 3 —OR₂, or 1 to 2 —C(O)OR₂;

R₉ is selected from the group consisting of:

—R₂, —(CH₂)$_q$-aryl, —C(O)R₂, —C(O)(CH₂)$_q$-aryl, —SO₂R₂, —SO₂(CH₂)$_q$-aryl, —C(O)N(R₂)(R₂), —C(O)N(R₂)(CH₂)$_q$-aryl,—C(O)OR₂, 1-H-tetrazol-5-yl, —SO₃H,—SO₂NHC≡N, —SO₂N(R₂)aryl, and —SO₂N(R₂)(R₂), where the (CH₂)$_q$ is optionally substituted by 1 to 2 $C_1$–$C_4$ alkyl, and R₂ and aryl are optionally further substituted by 1 to 3 —OR$_{2a}$, —O(CH₂)$_q$ aryl, 1 to 2 —C(O)OR$_{2a}$, 1 to 2 —C(O)O(CH₂)q aryl, 1 to 2 —C(O)N(R$_{2a}$)(R$_{2a}$), 1 to 2 —C(O)N(R$_{2a}$)(CH₂)$_q$aryl, 1 to 5 halogen, 1 to 3 $C_1$–$C_4$ alkyl, 1,2,4-triazolyl, 1H-tetrazol-5-yl, —C(O)NHSO₂R$_{2a}$, —S(O)$_m$R$_{2a}$, —C(O)NHSO₂(CH₂)$_q$-aryl, —SO₂NHC≡N, —SO₂NHC(O)R$_{2a}$, —SO₂NHC(O)(CH₂)$_q$aryl, —N(R₂)C(O)N(R$_{2a}$)(R$_{2a}$), —N(R$_{2a}$)C(O)N(R$_{2a}$)(CH₂)$_q$-aryl, —N(R$_{2a}$)(R$_{2a}$), —N(R$_{2a}$)C(O)R$_{2a}$, —N(R$_{2a}$)C(O)(CH₂)$_q$ aryl,— OC(O)N(R$_{2a}$)(R$_{2a}$), —OC(O)N(R$_{2a}$)(CH₂)$_q$ aryl, or —SO₂(CH₂)$_q$CONH—(CH₂)$_w$NHC(O)R₁₁, where w is 2 to 6 and R 11 is biotin, aryl, or aryl substituted by 1 or 2 —OR₂, 1 to 2 halogen, azido, or nitro;

m is 0, 1 or 2;

n is 1 or 2;

q is 0, 1, 2, 3, or 4; and

G, H, I and J are carbon, nitrogen, sulfur or oxygen atoms, such that one or two is a heteroatom, and where one of G, H, I or J may be optionally absent to afford a 5 or 6 membered heterocyclic aromatic ring;

and the pharmaceutically acceptable salts and individual diastereomers thereof.

2. The compound of claim 1 of the formula:

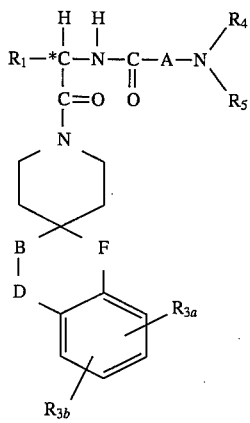

Formula III wherein:

$R_1$ is selected from the group consisting of: $C_1$–$C_{10}$ alkyl, aryl ($C_1$–$C_4$ alkyl)-, $C_3$–$C_6$ cycloalkyl—($C_1$–$C_4$ alkyl)-, ($C_1$–$C_4$ alkyl)-K—($C_1$–$C_4$ alkyl)-, aryl($C_0$–$C_5$alkyl)-K—($C_1$–$C_4$ alkyl)-, and ($C_3$–$C_7$cycloalkyl)($C_0$–$C_5$ alkyl)-K—($C_1$–$C_4$alkyl)-, where K is —O—, —S(O)$_m$—, —CR$_2$=CR$_2$—, —C≡C—, or —N(R$_2$)C(O)—, where $R_2$ and the alkyl groups may be further substituted by 1 to 7 halogen, —S(O)$_m$C$_1$–C$_4$alkyl, —OR$_2$, or —C(O)OR$_2$, and where the aryl groups may be further substituted by $C_1$–$C_4$ alkyl, 1 to 2 halogen, 1 to 2 —OR$_2$, —CF$_3$, —OCF$_3$, methylenedioxy, —S(O)$_m$R$_2$, —SO$_2$N(R$_2$)(R$_2$), —N(R$_2$)SO$_2$R$_2$, or —C(O)OR$_2$;

$R_2$ is selected from the group consisting of:

hydrogen, $C_1$–$C_6$ alkyl, and $C_3$–$C_7$cycloalkyl, and, where two $C_1$–$C_6$ alkyl groups are present on one atom, they may be optionally joined to form a $C_4$–$C_6$ cyclic ring optionally including 1 to 2 heteroatoms selected from oxygen, sulfur, or NR$_{2a}$;

$R_{2a}$ is hydrogen or $C_1$–$C_6$ alkyl;

$R_{3a}$ and $R_{3b}$ are independently selected from the group consisting of:

hydrogen, halogen, $C_1$–$C_4$ alkyl, —OR$_2$, methylenedioxy, nitro, —S(O)$_m$(C$_1$–C$_4$alkyl), —CF$_3$, and —C(O)OR$_2$;

$R_4$ and $R_5$ are independently selected from the group consisting of:

hydrogen, $C_1$–$C_6$ alkyl, and substituted $C_1$–$C_6$ alkyl where the substituents on alkyl are 1 to 5 halo, 1 to 2 hydroxy, 1 to 2 $C_1$–$C_6$ alkanoyloxy, 1 to 2 $C_1$–$C_6$ alkyloxy, or —S(O)$_m$(C$_1$–C$_4$ alkyl);

A is:

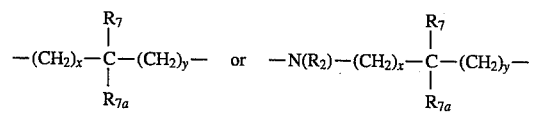

wherein x and y are independently 0, 1, or 2;

$R_7$ and $R_{7a}$ are independently selected from the group consisting of:

hydrogen, $C_1$–$C_4$ alkyl, and substituted $C_1$–$C_4$ alkyl where the substituents are selected from 1 to 3 fluoro, imidazolyl, phenyl, indolyl, —S(O)$_m$C$_1$–C$_4$alkyl, and —C(O)OR$_2$, or $R_7$ and $R_{7a}$ may independently be joined to one or both of the $R_4$ and $R_5$ groups to form an alkylene bridge between the teminal nitrogen and the alkyl portion of the $R_7$ or $R_{7a}$ groups, wherein the bridge contains 1 to 3 carbon atoms;

B, D, and F are independently selected from the group consisting of:

—C(R$_8$)(R$_{10}$)—, C=O, —O—, —S(O)$_m$—, and —NR$_9$—, wherein one of B, D, or F may be optionally absent to provide a 5 or 6 membered ring, provided that one of B, D or F is —O—, —S(O)$_m$—, or —NR$_9$—, and at least one of the remaining B, D or F is —C(R$_8$)(R$_{10}$)— or C=O;

$R_8$ and $R_{10}$ are independently selected from the group consisting of:

hydrogen, —R$_2$, —OR$_2$, —(CH$_2$)$_q$-aryl, —(CH$_2$)$_q$—C(O)OR$_2$, —(CH$_2$)$_q$—C(O)O(CH$_2$)$_q$-aryl, and —(CH$_2$)$_q$—(1H-tetrazol-5-yl), where the aryl is optionally substituted by 1 to 3 halo, 1 to 2 $C_1$–$C_4$ alkyl, 1 to 3 —OR$_2$, or 1 to 2 —C(O)OR$_2$;

$R_9$ is selected from the group consisting of:

—R$_2$, —(CH$_2$)$_q$-aryl, —C(O)R$_2$, —C(O)(CH$_2$)$_q$-aryl, —SO$_2$R$_2$, —SO$_2$(CH$_2$)$_q$-aryl, —C(O)N(R$_2$)(R$_2$), —C(O)N(R$_2$)(CH$_2$)$_q$-aryl, 1H-tetrazolyl-5-yl, —SO$_2$NHC≡N, —SO$_2$N(R$_2$) aryl, and —SO$_2$N(R$_2$)(R$_2$), where the (CH$_2$)$_q$ is optionally substituted by 1 to 2 $C_1$–$C_2$ alkyl, and $R_2$ is optionally substituted by 1 to 2 —OR$_{2a}$, —O(CH$_2$)$_q$ aryl, 1 to 2 —C(O)OR$_{2a}$, —C(O)N(R$_{2a}$)(R$_{2a}$), —S(O)$_m$R$_{2a}$, 1H-tetrazol-5-yl, —C(O)NHSO$_2$R$_{2a}$, —C(O)NHSO$_2$(CH$_2$)$_q$-aryl, —N(R$_{2a}$)C(O)N(R$_{2a}$)(R$_{2a}$), or N(R$_{2a}$)C(O)N(R$_{2a}$)(CH$_2$)$_q$-aryl, where the aryl is optionally substituted by 1 to 2—OR$_{2a}$, 1 to 2 halogen, 1 to 2 $C_1$–$C_4$ alkyl, —C(O)OR$_{2a}$, 1H-tetrazol-5-yl, or —SO$_2$(CH$_2$)$_w$CONH(CH$_2$)$_w$NHC(O)R$_{11}$, where w is 1 to 6 and $R_{11}$ is biotin, aryl, or aryl substituted by 1 or 2 —OR$_2$, 1 to 2 halogen, azido, or nitro;

m is 0, 1, or 2;

q is 0, 1, 2, or 3; and aryl is selected from the group consisting of: phenyl, napthyl, pyridyl, thienyl, indolyl, thiazolyl, and pyrimidinyl;

and the pharmaceutically acceptable salts and individual diastereomers thereof.

3. The compound of claim 2 wherein F is not present.

4. The compound of claim 3 of the formula:

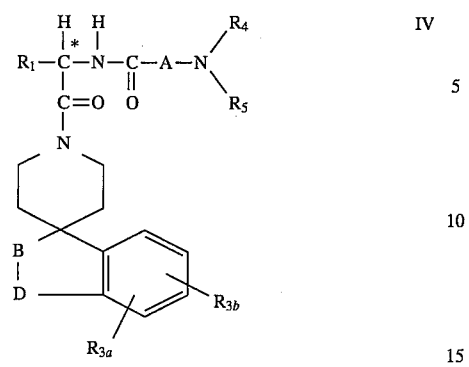

wherein:

$R_1$ is selected from the group consisting of: $C_1$–$C_{10}$ alkyl, aryl ($C_1$–$C_4$ alkyl)-, $C_5$–$C_6$ cycloalkyl-($C_1$–$C_4$ alkyl)-, ($C_1$–$C_4$ alkyl)-K—$C_1$–$C_2$alkyl-, aryl($C_0$–$C_2$alkyl)-K—($C_1$–$C_2$ alkyl)-, and $C_3$–$C_6$ cycloalkyl($C_0$–$C_2$alkyl)-K—($C_1$–$C_2$alkyl)-, wherein K is O or $S(O)_m$, and where the aryl groups may be further substituted by 1 to 2 $C_1$–$C_4$ alkyl, 1 to 2 halogen, —$OR_2$, —$C(O)OR_2$, —$CF_3$, or —$S(O)_mR_2$;

$R_2$ is selected from the group consisting of:

hydrogen, $C_1$–$C_4$ alkyl, and $C_3$–$C_6$ cycloalkyl, and, where two $C_1$–$C_4$ alkyls are present on one atom, they may be optionally joined to form a $C_5$–$C_6$ cyclic ring optionally including the heteroatoms oxygen or $NR_{2a}$;

$R_{2a}$ is hydrogen or $C_1$–$C_4$ alkyl;

$R_{3a}$ and $R_{3b}$ are independently selected from the group consisting of:

hydrogen, halogen, $C_1$–$C_4$ alkyl, —$C(O)OR_2$, hydroxy, $C_1$–$C_4$ alkoxy, —$S(O)_mC_1$–$C_4$ alkyl, and —$CF_3$;

$R_4$ and $R_5$ are independently selected from the group consisting of:

hydrogen, $C_1$–$C_4$ alkyl, and substituted $C_1$–$C_4$ alkyl where the substituents on alkyl are 1 to 2 hydroxy, or —$S(O)_m(C_1$–$C_3$alkyl);

A is:

where x is 0 or 1;

$R_7$ and $R_{7a}$ are independently hydrogen, or $C_1$–$C_3$ alkyl, or $R_7$ and $R_{7a}$ may independently be joined to one or both of the $R_4$ and $R_5$ groups to form an alkylene bridge between the terminal nitrogen and the alkyl portion of the $R_7$ or $R_{7a}$ groups, wherein the bridge forms a 5 or 6 membered ring containing the terminal nitrogen;

B and D are independently selected from the group consisting of:

—$C(R_8)(R_{10})$—, C=O, —O—, —$S(O)_m$—, and —$NR_9$—, provided that one of B and D may be —$C(R_8)(R_{10})$— or C=O only when the remaining of B or D is —O—, —$S(O)_m$—, or —$NR_9$—, and further provided that B and D are not simultaneously —O—;

$R_8$ and $R_{10}$ are independently selected from the group consisting of:

hydrogen, —$R_2$, —$OR_2$, and —$(CH_2)_q$-aryl, where the aryl is optionally substituted by 1 to 2 of halo, 1 to 2 $C_1$–$C_4$ alkyl, $OR_2$, or 1 to 2 $C(O)OR_2$;

$R_9$ is selected from the group consisting of:

—$C(O)R_2$, —$C(O)(CH_2)_q$-aryl, —$SO_2R_2$, —$SO(CH_2)_q$-aryl, —$C(O)N(R_2)(R_2)$, and —$C(O)N(R_2)(CH_2)_q$-aryl, where the $(CH_2)_q$ is optionally substituted by 1 to 2 $C_1$–$C_2$ alkyl, and $R_2$ is optionally substituted by 1 to 2 of —$OR_{2a}$, —$O(CH_2)_q$-aryl, —$C(O)OR_{2a}$, —$C(O)N(R_{2a})(R_{2a})$, —$S(O)_mR_{2a}$, 1H-tetrazol-5-yl, —$C(O)NHSO_2R_{2a}$, or —$N(R_{2a})C(O)N(R_{2a})(R_{2a})$, and aryl is optionally substituted by 1 to 2 —$OR_{2a}$, 1 to 2 halogen, 1 to 2 $C_1$–$C_2$ alkyl, —$C(O)OR_{2a}$, 1H-tetrazol-5-yl, —$S(O)_mR_{2a}$, or —$SO_2(CH_2)_qCONH(CH_2)_wNHC(O)R_{11}$, where w is 2 to 6 and $R_{11}$ is biotin, aryl, or aryl substituted by 1 to 2—$OR_2$, 1–2 halogen, azido, or nitro;

m is 0, 1 or 2;

q is 0, 1, 2 or 3;

aryl is selected from the group consisting of:

phenyl, napthyl, pyridyl, indolyl, thienyl, and tetrazolyl; and the pharmaceutically acceptable salts and individual diastereomers thereof.

5. A compound of the formula:

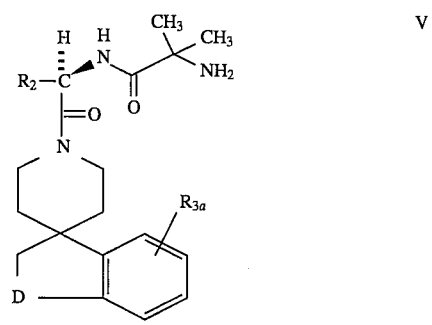

wherein:

$R_1$ is selected from the group consisting of:

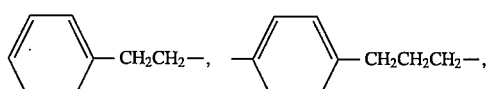

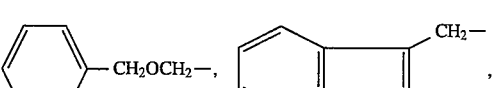

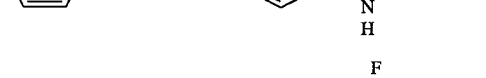

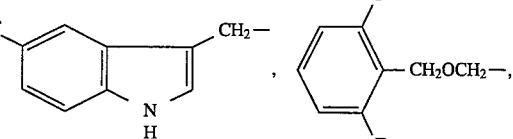

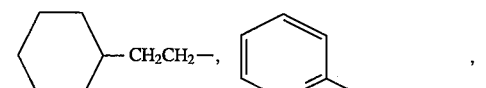

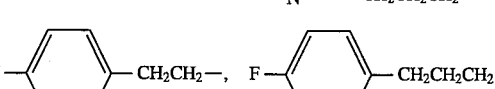

$R_{3a}$ is hydrogen or fluoro;

D is selected from the group consisting of:

—O—, —S—, —$S(O)_m$—, —$N(R_2)$—, $NSO_2(R_2)$, $NSO_2(CH_2)_t$aryl, $NC(O)(R_2)$, $NSO_2(CH_2)_qOH$, NSO₂(CH₂)qCOOR₂, N—SO₂(CH₂)qC(O)—N(R₂)(R₂), N—SO₂(CH₂)qC(O)—N(R₂)(CH₂)wOH,

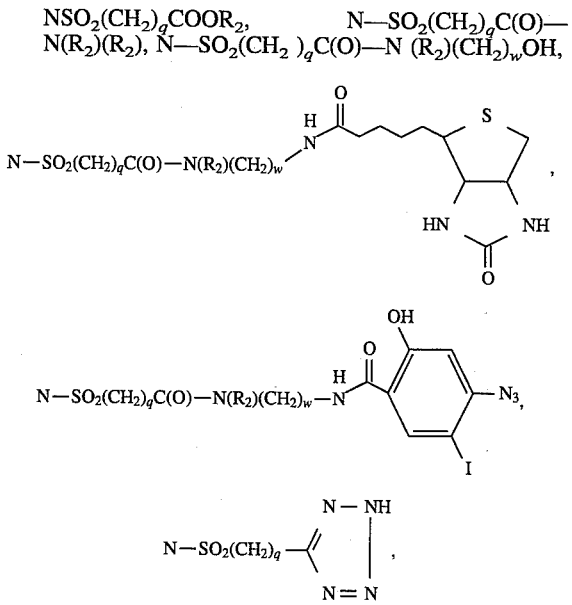

and aryl is phenyl or pyridyl, where phenyl may be substituted by 1 or 2 halogen;

$R_2$ is hydrogen or $C_1$–$C_4$ alkyl;

m is 1 or 2;

t is 0, 1, or 2;

q is 1, 2, or 3;

w is 2, 3, 4, 5, or 6;

and the pharmaceutically acceptable salts and individual diastereomers thereof.

6. A compound which is selected from the group consisting of:

1) N-[1(R)-[(1,2-dihydro-1-methanesulfonylspiro[3H-indole-3,4'-piperidin]-1'-yl)carbonyl]-2-(1H-indol-3-yl)ethyl]-2-amino- 2-methyl-propanamide;

2) N-[1(R)-[(1,2-dihydro-1-methanecarbonylspiro[3H-indole- 3,4'-piperidin]-1'-yl)carbonyl]-2-(1H-indol-3-yl)ethyl]-2-amino- 2-methyl-propanamide;

3) N-[1(R)-[(1,2-dihydro-1-benzenesulfonylspiro[3H-indole- 3,4'-piperidin]-1'-yl)carbonyl]-2-(1H-indol-3-yl)ethyl]-2-amino- 2-methyl-propanamide;

4) N-[1(R)-[(3,4-dihydro-spiro[2H-1-benzopyran- 2,4'-piperidin]-1'-yl)carbonyl]-2-(1H-indol-3-yl)ethyl]-2-amino- 2-methylpropanamide;

5) N-[1(R)-[(2-acetyl-1,2,3,4-tetrahydrospiro[isoquinolin-4,4'-piperidin]-1'-yl)carbonyl]-2-(indol-3-yl)ethyl]-2-amino- 2-methylpropanamide;

6) N-[1(R)-[(1,2-dihydro-1-methanesulfonylspiro[3H-indole-3,4'-piperidin]-1'-yl)carbonyl]-2-(phenylmethyloxy)ethyl]-2-amino- 2-methylpropanamide;

7N-[1(R)-[(1,2-dihydro-1-methanesulfonylspiro[3H-indole-3,4'-piperidin]-1'-yl)carbonyl]-2-(phenylmethyloxy)ethyl]-2-amino- 2-methylpropanamide mesylate salt;

8) N-[1(R)-[(1,2-dihydro-1-methanesulfonylspiro[3H-indole-3,4'-piperidin]-1'-yl)carbonyl]-2-(2',6'-difluorophenylmethyloxy)ethyl]- 2-amino-2-methylpropanamide;

9) N-[1(R)-[(1,2-dihydro-1-methanesulfonyl-5-fluorospiro[3H-indole-3,4'-piperidin]-1'-yl)carbonyl]-2-(phenylmethyloxy)ethyl]- 2-amino-2-methylpropanamide;

10) N-[1(S)-[(1,2-dihydro-1-methanesulfonylspiro[3H-indole-3,4'-piperidin]- 1'-yl)carbonyl]-2-(phenylmethylthio)ethyl]-2-amino- 2-methylpropanamide;

11) N-[1(R)-[(1,2-dihydro-1-methanesulfonylspiro[3H-indole-3,4'-piperidin]- 1'-yl)carbonyl]-3-phenylpropyl]-2-amino-2-methylpropanamide;

12) N-[1(R)-[(1,2-dihydro-1-methanesulfonylspiro[3H-indole- 3,4'-piperidin]-1'-yl)carbonyl]-3-cyclohexylpropyl]-2-amino-2-methylpropanamide;

13) N-[1(R)-[(1,2-dihydro-1-methanesulfonylspiro[3H-indole-3,4'-piperidin]- 1'-yl)carbonyl]-4-phenylbutyl]-2-amino-2-methylpropanamide;

14) N-[1(R)-[(1,2-dihydro-1-methanesulfonylspiro[3H-indole-3,4'-piperidin]- 1'-yl)carbonyl]-2-(5-fluoro-1H-indol-3-yl)ethyl]- 2-amino-2-methylpropanamide;

15) N-[1(R)-[(1,2-dihydro-1-methanesulfonyl-5-fluorospiro[3 H-indole-3,4'-piperidin ]-1'-yl)carbonyl]-2-(5-fluoro-1H-indol- 3-yl)ethyl]-2-amino-2-methylpropanamide;

16) N-[1(R)-[(1,2-dihydro-1-(2-ethoxycarbonyl)methylsulfonylspiro-[3H-indole-3,4'-piperidin]-1'-yl)carbonyl]-2-(1H-indol-3-yl)ethyl]- 2-amino-2-methylpropanamide; and 17) N-[1(R)-[(1,2-dihydro-1,1-dioxospiro[3H-benzothiophene-3,4 '-piperidin]-1-yl)carbonyl]-2-(phenylmethyloxy)ethyl]- 2-amino-2-methylpropanamide;

and pharmaceutically acceptable salts thereof.

7. A compound which is selected from the group consisting of:

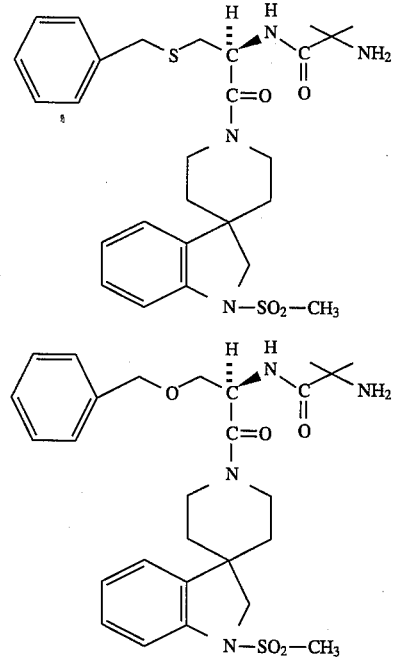

and pharmaceutically acceptable salts thereof.

8. A compound which is

N-[1(R)-[(1,2-dihydro-1-methanesulfonylspiro[3H-indole-3,4'-piperidin]- 1'-yl)carbonyl]-2-(phenylmethyloxy)ethyl]-2-amino-2-methylpropanamide;

or a pharmaceutically acceptable salt thereof.

9. A compound which is

N-[1(R)-[(1,2-dihydro-1-methanesulfonylspiro[3H-indole-3,4'-piperidin]- 1'-yl)carbonyl]-2-(phenylmethyloxy)ethyl]-2-amino-2-methylpropanamide mesylate salt.

10. The compound of claim 1 of the formula:

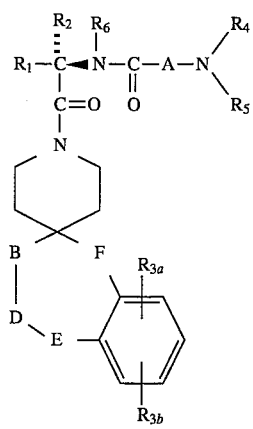

wherein $R_1$, $R_2$, $R_{3a}$, $R_{3b}$, $R_4$, $R_5$, $R_6$, A, B, D, E, F, and n are as defined in claim 1.

11. A process for the preparation of a compound of claim 1 which comprises reacting a compound of the formula:

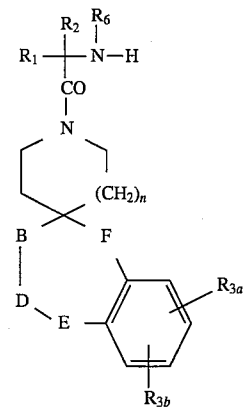

or

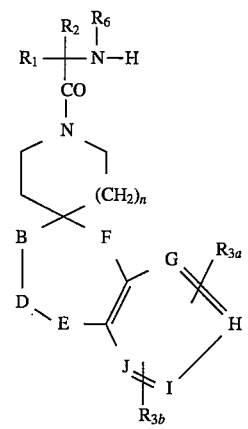

with a compound of the formula:

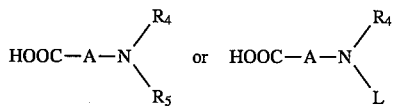

where $R_1$, $R_2$, $R_{3a}$, $R_{3b}$, $R_4$, $R_5$, $R_6$, A, B, D, E, F, G, H, I, J and n are as defined in claim 1 and L is a protecting group which is subsequently removed if present and salts are formed if desired.

12. A process for the preparation of a compound of claim 1 which comprises reacting a compound of the formula:

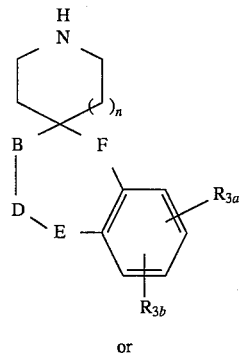

or

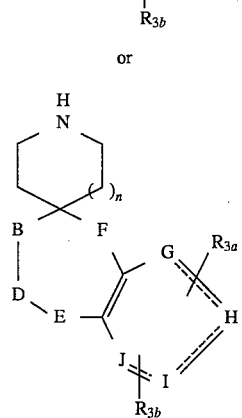

with a compound of the formula:

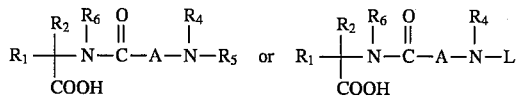

where $R_1$, $R_2$, $R_{3a}$, $R_{3b}$, $R_4$, $R_5$, $R_6$, A, B, D, E, F, G, H, I, J and n are as defined in claim 1 and L is a protecting group which is subsequently removed if present and salts are formed if desired.

13. A pharmaceutical composition which comprises an inert carrier and an effective amount of a compound of claim 1.

14. A compound which is selected from the group consisting of:

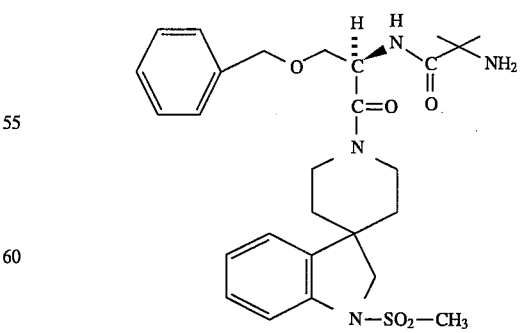

and pharmaceutically acceptable salts thereof.

15. The compound of claim 14 which is present as the mesylate salt.

16. A compound which is:
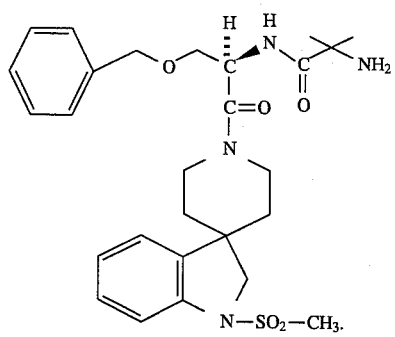
17. A pharmaceutical composition which comprises an inert carrier and an effective amount of a compound of claim 6.
18. A pharmaceutical composition which comprises an inert carrier and an effective amount of a compound of claim 14.
19. A pharmaceutical composition which comprises an inert carrier and an effective amount of a compound of claim 16.
* * * * *